US008592187B2

United States Patent
Bathe et al.

(10) Patent No.: US 8,592,187 B2
(45) Date of Patent: *Nov. 26, 2013

(54) ALLELES OF THE OXYR GENE FROM CORYNEFORM BACTERIA

(75) Inventors: Brigitte Bathe, Salzkotten (DE); Wilfried Claes, Bielefeld (DE); Silke Jerrentrup, Bielefeld (DE); Caroline Kreutzer, Oerlinghausen (DE); Georg Thierbach, Bielefeld (DE)

(73) Assignee: Evonik Degussa GmbH, Essen (DE)

( * ) Notice: Subject to any disclaimer, the term of this patent is extended or adjusted under 35 U.S.C. 154(b) by 523 days.

This patent is subject to a terminal disclaimer.

(21) Appl. No.: 13/027,732

(22) Filed: Feb. 15, 2011

(65) Prior Publication Data

US 2013/0142937 A1    Jun. 6, 2013

Related U.S. Application Data

(62) Division of application No. 11/937,888, filed on Nov. 9, 2007, now Pat. No. 7,910,715.

(30) Foreign Application Priority Data

Nov. 17, 2006   (DE) .......................... 10 2006 054 202

(51) Int. Cl.
*C12P 13/04* (2006.01)
*C12P 13/22* (2006.01)
*C12P 13/08* (2006.01)
*C12P 13/06* (2006.01)

(52) U.S. Cl.
USPC ............ 435/106; 435/108; 435/115; 435/116

(58) Field of Classification Search
None
See application file for complete search history.

(56) References Cited

FOREIGN PATENT DOCUMENTS

WO          02/18431   A1       3/2002

OTHER PUBLICATIONS

Kalinowski et al, The complete *Corynebacterium glutamicum* ATCC 13032 genome sequence and its impact on the production of L-aspartate-derived amino acids and vitamins, Journal of Biotechnology 104 (2003): 5-25. (XP-001184752).

Yukawa et al, Comparative analysis of the *Corynebacterium glutamicum* group and complete genome sequence of strain R, Microbiology 153 (2007): 1042-1058. (XP-002472798).

*Primary Examiner* — Suzanne M Noakes
*Assistant Examiner* — Jae W Lee
(74) *Attorney, Agent, or Firm* — Smith, Gambrell & Russell, LLP

(57) ABSTRACT

The invention relates to mutants and alleles of the oxyR gene of coryneform bacteria coding for variants of the OxyR transcription regulator and processes for producing amino acids using bacteria which comprise these alleles.

17 Claims, 1 Drawing Sheet

Plasmid pK18mobsacB_oxyR_A89V
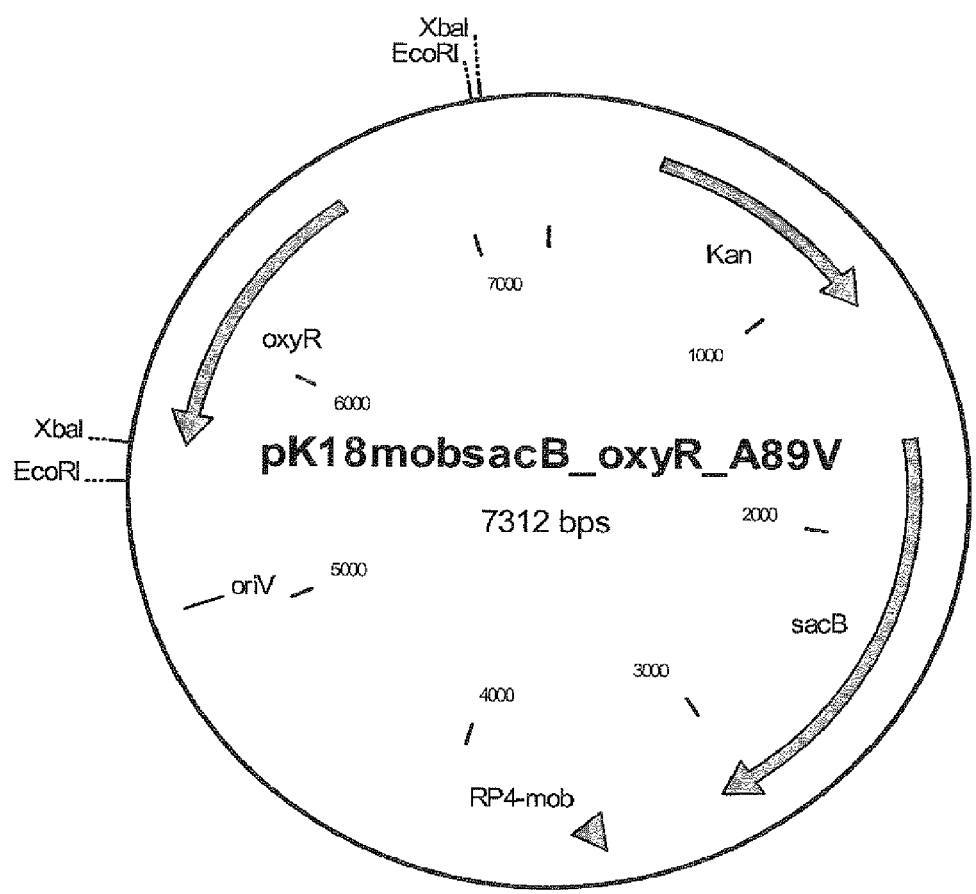

SEQUENCE LISTING

<160> NUMBER OF SEQ ID NOS: 24

<210> SEQ ID NO 1
<211> LENGTH: 984
<212> TYPE: DNA
<213> ORGANISM: Corynebacterium glutamicum
<220> FEATURE:
<221> NAME/KEY: CDS
<222> LOCATION: (1)..(981)
<223> OTHER INFORMATION: oxyR wild type gene
<220> FEATURE:
<221> NAME/KEY: misc_feature
<222> LOCATION: (266)..(266)
<223> OTHER INFORMATION: cytosine
<220> FEATURE:
<221> NAME/KEY: misc_feature
<222> LOCATION: (731)..(731)
<223> OTHER INFORMATION: cytosine

<400> SEQUENCE: 1

```
atg agc aat aaa gag tac cgg ccc aca ctc gcc cag ctt cgc acc ttt      48
Met Ser Asn Lys Glu Tyr Arg Pro Thr Leu Ala Gln Leu Arg Thr Phe
1               5                   10                  15 gtc acc atc gca gaa tgc aag cac ttt ggt act gct gcc acc aag ctg      96
Val Thr Ile Ala Glu Cys Lys His Phe Gly Thr Ala Ala Thr Lys Leu
            20                  25                  30 tcc att tcg cag cca tcc ctc tcc cag gca ctt gtc gca tta gaa aca     144
Ser Ile Ser Gln Pro Ser Leu Ser Gln Ala Leu Val Ala Leu Glu Thr
        35                  40                  45 ggc ctg gga gtt cag ctg att gaa cgc tcc acc cgc aag gtc att gtc     192
Gly Leu Gly Val Gln Leu Ile Glu Arg Ser Thr Arg Lys Val Ile Val
    50                  55                  60 acc cca gcg ggc gag aag ttg ctg cca ttc gcc aaa tcc acc ctt gac     240
Thr Pro Ala Gly Glu Lys Leu Leu Pro Phe Ala Lys Ser Thr Leu Asp
65                  70                  75                  80 gcg gcg gag tct ttc ctc tcc cac gcc aag ggc gcc aac ggt tcg ctc     288
Ala Ala Glu Ser Phe Leu Ser His Ala Lys Gly Ala Asn Gly Ser Leu
                85                  90                  95 act gga ccg ttg acc gta ggc atc atc ccc acg gcg gct cct tac att     336
Thr Gly Pro Leu Thr Val Gly Ile Ile Pro Thr Ala Ala Pro Tyr Ile
            100                 105                 110 ttg ccg tca atg ctg tcc atc gtg gat gaa gaa tat cca gat ctg gaa     384
Leu Pro Ser Met Leu Ser Ile Val Asp Glu Glu Tyr Pro Asp Leu Glu
        115                 120                 125
```

| | | | | | | | | | | | | | | | | |
|---|---|---|---|---|---|---|---|---|---|---|---|---|---|---|---|---|
| cct | cac | atc | gtc | gag | gac | caa | acc | aag | cat | ctt | ctc | gcg | ttg | ctg | cgc | 432 |
| Pro | His | Ile | Val | Glu | Asp | Gln | Thr | Lys | His | Leu | Leu | Ala | Leu | Leu | Arg | |
| | 130 | | | | 135 | | | | 140 | | | | | | | |
| gac | ggc | gcc | atc | gac | gtc | gcc | atg | atg | gcc | ctg | cct | tct | gag | gca | cca | 480 |
| Asp | Gly | Ala | Ile | Asp | Val | Ala | Met | Met | Ala | Leu | Pro | Ser | Glu | Ala | Pro | |
| 145 | | | | | 150 | | | | | 155 | | | | | 160 | |
| ggc | atg | aag | gaa | atc | ccc | ctc | tac | gac | gaa | gac | ttt | atc | gtc | gtt | aca | 528 |
| Gly | Met | Lys | Glu | Ile | Pro | Leu | Tyr | Asp | Glu | Asp | Phe | Ile | Val | Val | Thr | |
| | | | | 165 | | | | | 170 | | | | | 175 | | |
| gct | agc | gat | cac | ccc | ttc | gcc | ggc | cgc | caa | gac | tta | gaa | cta | tcc | gcc | 576 |
| Ala | Ser | Asp | His | Pro | Phe | Ala | Gly | Arg | Gln | Asp | Leu | Glu | Leu | Ser | Ala | |
| | | | 180 | | | | | 185 | | | | | 190 | | | |
| tta | gaa | gac | ctc | gat | ctg | ctg | ctt | ctc | gac | gac | gga | cac | tgc | ctc | cac | 624 |
| Leu | Glu | Asp | Leu | Asp | Leu | Leu | Leu | Leu | Asp | Asp | Gly | His | Cys | Leu | His | |
| | | 195 | | | | | 200 | | | | | 205 | | | | |
| gac | caa | att | gtg | gac | ctg | tgc | cgc | cgc | gga | gac | atc | aac | ccc | att | agc | 672 |
| Asp | Gln | Ile | Val | Asp | Leu | Cys | Arg | Arg | Gly | Asp | Ile | Asn | Pro | Ile | Ser | |
| | 210 | | | | 215 | | | | | 220 | | | | | | |
| tcc | act | act | gct | gtc | acc | cgc | gca | tcc | agc | ctt | acc | acc | gtc | atg | cag | 720 |
| Ser | Thr | Thr | Ala | Val | Thr | Arg | Ala | Ser | Ser | Leu | Thr | Thr | Val | Met | Gln | |
| 225 | | | | | 230 | | | | | 235 | | | | | 240 | |
| ctc | gtc | gtc | gcc | ggc | ctt | gga | tcc | acc | ttg | gtc | cca | atc | agc | gca | atc | 768 |
| Leu | Val | Val | Ala | Gly | Leu | Gly | Ser | Thr | Leu | Val | Pro | Ile | Ser | Ala | Ile | |
| | | | | 245 | | | | | 250 | | | | | 255 | | |
| cca | tgg | gaa | tgc | acc | cga | cca | gga | ctg | gca | aca | gcc | aac | ttc | aac | tct | 816 |
| Pro | Trp | Glu | Cys | Thr | Arg | Pro | Gly | Leu | Ala | Thr | Ala | Asn | Phe | Asn | Ser | |
| | | | 260 | | | | | 265 | | | | | 270 | | | |
| gat | gtc | acc | gca | aac | cgc | cgc | att | gga | ttg | gtg | tac | cgt | tcc | tct | tct | 864 |
| Asp | Val | Thr | Ala | Asn | Arg | Arg | Ile | Gly | Leu | Val | Tyr | Arg | Ser | Ser | Ser | |
| | | 275 | | | | | 280 | | | | | 285 | | | | |
| tct | cgc | gcc | gaa | gag | ttc | gaa | cag | ttt | gca | ctc | att | ttg | cag | cgc | gct | 912 |
| Ser | Arg | Ala | Glu | Glu | Phe | Glu | Gln | Phe | Ala | Leu | Ile | Leu | Gln | Arg | Ala | |
| | 290 | | | | 295 | | | | | 300 | | | | | | |
| ttc | caa | gaa | gcc | gtc | gcg | ctt | gct | gcc | tca | act | ggc | atc | acc | ttg | aag | 960 |
| Phe | Gln | Glu | Ala | Val | Ala | Leu | Ala | Ala | Ser | Thr | Gly | Ile | Thr | Leu | Lys | |
| 305 | | | | | 310 | | | | | 315 | | | | | 320 | |
| caa | aat | gtc | gcg | gta | gcg | cag | taa | | | | | | | | | 984 |
| Gln | Asn | Val | Ala | Val | Ala | Gln | | | | | | | | | | |
| | | | | 325 | | | | | | | | | | | | |

<210> SEQ ID NO 2
<211> LENGTH: 327
<212> TYPE: PRT
<213> ORGANISM: Corynebacterium glutamicum

<400> SEQUENCE: 2

Met Ser Asn Lys Glu Tyr Arg Pro Thr Leu Ala Gln Leu Arg Thr Phe
1               5                   10                  15

Val Thr Ile Ala Glu Cys Lys His Phe Gly Thr Ala Ala Thr Lys Leu
            20                  25                  30

Ser Ile Ser Gln Pro Ser Leu Ser Gln Ala Leu Val Ala Leu Glu Thr
        35                  40                  45

Gly Leu Gly Val Gln Leu Ile Glu Arg Ser Thr Arg Lys Val Ile Val
    50                  55                  60

Thr Pro Ala Gly Glu Lys Leu Leu Pro Phe Ala Lys Ser Thr Leu Asp
65                  70                  75                  80

Ala Ala Glu Ser Phe Leu Ser His Ala Lys Gly Ala Asn Gly Ser Leu
                85                  90                  95

Thr Gly Pro Leu Thr Val Gly Ile Ile Pro Thr Ala Ala Pro Tyr Ile
            100                 105                 110

```
Leu Pro Ser Met Leu Ser Ile Val Asp Glu Glu Tyr Pro Asp Leu Glu
        115                 120                 125

Pro His Ile Val Glu Asp Gln Thr Lys His Leu Leu Ala Leu Leu Arg
    130                 135                 140

Asp Gly Ala Ile Asp Val Ala Met Met Ala Leu Pro Ser Glu Ala Pro
145                 150                 155                 160

Gly Met Lys Glu Ile Pro Leu Tyr Asp Glu Asp Phe Ile Val Val Thr
                165                 170                 175

Ala Ser Asp His Pro Phe Ala Gly Arg Gln Asp Leu Glu Leu Ser Ala
            180                 185                 190

Leu Glu Asp Leu Asp Leu Leu Leu Asp Asp Gly His Cys Leu His
        195                 200                 205

Asp Gln Ile Val Asp Leu Cys Arg Arg Gly Asp Ile Asn Pro Ile Ser
    210                 215                 220

Ser Thr Thr Ala Val Thr Arg Ala Ser Ser Leu Thr Thr Val Met Gln
225                 230                 235                 240

Leu Val Val Ala Gly Leu Gly Ser Thr Leu Val Pro Ile Ser Ala Ile
                245                 250                 255

Pro Trp Glu Cys Thr Arg Pro Gly Leu Ala Thr Ala Asn Phe Asn Ser
                260                 265                 270

Asp Val Thr Ala Asn Arg Arg Ile Gly Leu Val Tyr Arg Ser Ser Ser
            275                 280                 285

Ser Arg Ala Glu Glu Phe Glu Gln Phe Ala Leu Ile Leu Gln Arg Ala
        290                 295                 300

Phe Gln Glu Ala Val Ala Leu Ala Ala Ser Thr Gly Ile Thr Leu Lys
305                 310                 315                 320

Gln Asn Val Ala Val Ala Gln
                325

<210> SEQ ID NO 3
<211> LENGTH: 2484
<212> TYPE: DNA
<213> ORGANISM: Corynebacterium glutamicum
<220> FEATURE:
<221> NAME/KEY: misc_feature
<222> LOCATION: (1)..(750)
<223> OTHER INFORMATION: nucleotide sequence upstream of CDS
<220> FEATURE:
<221> NAME/KEY: CDS
<222> LOCATION: (751)..(1731)
<223> OTHER INFORMATION: oxyR wild type gene
<220> FEATURE:
<221> NAME/KEY: misc_feature
<222> LOCATION: (1016)..(1016)
<223> OTHER INFORMATION: cytosine
<220> FEATURE:
<221> NAME/KEY: misc_feature
<222> LOCATION: (1481)..(1481)
<223> OTHER INFORMATION: cytosine
<220> FEATURE:
<221> NAME/KEY: misc_feature
<222> LOCATION: (1732)..(2484)
<223> OTHER INFORMATION: nucleotide sequence downstream of CDS

<400> SEQUENCE: 3
cctacggtgt ggccaggtca gagggtgttg cgctgcgcta cctcaccgat gcctggcgta      60
ctctccaaca ctcactgcct acggaagctc gcaccgagga acttgatgat gttgtggtgt     120
ggttgggcga actgatcaaa caggtcgact cctccctggt ggatgagtgg gctcagatgg     180
cggatccaga agcaccgatc agcaaggaag cgctggaacg agagctcgcc ttcggcgtgg     240
aagacccaac agcacttacc gccaaccgca gggcatttac catcatggtg cgcaacgcca     300
```

-continued

```
tgttccgcct tgtggagcta tttgcttatg aaaaggaaga tcagcttagt cagatgactg      360
aatacctgga tgaggctcct gatttcggtg ctgcgatgga tgcgtacttt gatgaatatg      420
cggatcttga taccggcccg gcagctcgtg gaccagagtt cttcaaggta gagcacacgg      480
gaagaatgtg ggaggtgcgt caggtggtga aggatccaga aggtgataat tccttcgcgt      540 tgttgccac cattgatctt gatgcctctg atgatgcagg tgaggtgcgt tttggatcgc       600
tgtcgattga ccacaactag gggtttgcgt cgaaaagcaa gcacgcctgg tgcctgattt      660
gagcggtttt acctatggcg ctttggcgcc gtcaaactgt cccagcgatt tcattattat      720
tttcgtgcat tcaccgttat agttataggc atg agc aat aaa gag tac cgg ccc      774
                                 Met Ser Asn Lys Glu Tyr Arg Pro
                                  1               5
```

| | | | | | | | | | | | | | | | | |
|---|---|---|---|---|---|---|---|---|---|---|---|---|---|---|---|---|
| aca | ctc | gcc | cag | ctt | cgc | acc | ttt | gtc | acc | atc | gca | gaa | tgc | aag | cac | 822 |
| Thr | Leu | Ala | Gln | Leu | Arg | Thr | Phe | Val | Thr | Ile | Ala | Glu | Cys | Lys | His | |
| | 10 | | | | 15 | | | | | 20 | | | | | | |

| | | | | | | | | | | | | | | | | |
|---|---|---|---|---|---|---|---|---|---|---|---|---|---|---|---|---|
| ttt | ggt | act | gct | gcc | acc | aag | ctg | tcc | att | tcg | cag | cca | tcc | ctc | tcc | 870 |
| Phe | Gly | Thr | Ala | Ala | Thr | Lys | Leu | Ser | Ile | Ser | Gln | Pro | Ser | Leu | Ser | |
| 25 | | | | | 30 | | | | | 35 | | | | | 40 | |

| | | | | | | | | | | | | | | | | |
|---|---|---|---|---|---|---|---|---|---|---|---|---|---|---|---|---|
| cag | gca | ctt | gtc | gca | tta | gaa | aca | ggc | tg | gga | gtt | cag | ctg | att | gaa | 918 |
| Gln | Ala | Leu | Val | Ala | Leu | Glu | Thr | Gly | Leu | Gly | Val | Gln | Leu | Ile | Glu | |
| | | | | 45 | | | | | 50 | | | | | 55 | | |

| | | | | | | | | | | | | | | | | |
|---|---|---|---|---|---|---|---|---|---|---|---|---|---|---|---|---|
| cgc | tcc | acc | cgc | aag | gtc | att | gtc | acc | cca | gcg | ggc | gag | aag | ttg | ctg | 966 |
| Arg | Ser | Thr | Arg | Lys | Val | Ile | Val | Thr | Pro | Ala | Gly | Glu | Lys | Leu | Leu | |
| | | | 60 | | | | | 65 | | | | | 70 | | | |

| | | | | | | | | | | | | | | | | |
|---|---|---|---|---|---|---|---|---|---|---|---|---|---|---|---|---|
| cca | ttc | gcc | aaa | tcc | acc | ctt | gac | gcg | gcg | gag | tct | ttc | ctc | tcc | cac | 1014 |
| Pro | Phe | Ala | Lys | Ser | Thr | Leu | Asp | Ala | Ala | Glu | Ser | Phe | Leu | Ser | His | |
| | 75 | | | | | 80 | | | | | 85 | | | | | |

| | | | | | | | | | | | | | | | | |
|---|---|---|---|---|---|---|---|---|---|---|---|---|---|---|---|---|
| gcc | aag | ggc | gcc | aac | ggt | tcg | ctc | act | gga | ccg | ttg | acc | gta | ggc | atc | 1062 |
| Ala | Lys | Gly | Ala | Asn | Gly | Ser | Leu | Thr | Gly | Pro | Leu | Thr | Val | Gly | Ile | |
| | 90 | | | | | 95 | | | | | 100 | | | | | |

| | | | | | | | | | | | | | | | | |
|---|---|---|---|---|---|---|---|---|---|---|---|---|---|---|---|---|
| atc | ccc | acg | gcg | gct | cct | tac | att | ttg | ccg | tca | atg | ctg | tcc | atc | gtg | 1110 |
| Ile | Pro | Thr | Ala | Ala | Pro | Tyr | Ile | Leu | Pro | Ser | Met | Leu | Ser | Ile | Val | |
| 105 | | | | | 110 | | | | | 115 | | | | | 120 | |

| | | | | | | | | | | | | | | | | |
|---|---|---|---|---|---|---|---|---|---|---|---|---|---|---|---|---|
| gat | gaa | gaa | tat | cca | gat | ctg | gaa | cct | cac | atc | gtc | gag | gac | caa | acc | 1158 |
| Asp | Glu | Glu | Tyr | Pro | Asp | Leu | Glu | Pro | His | Ile | Val | Glu | Asp | Gln | Thr | |
| | | | | 125 | | | | | 130 | | | | | 135 | | |

| | | | | | | | | | | | | | | | | |
|---|---|---|---|---|---|---|---|---|---|---|---|---|---|---|---|---|
| aag | cat | ctt | ctc | gcg | ttg | ctg | cgc | gac | ggc | gcc | atc | gac | gtc | gcc | atg | 1206 |
| Lys | His | Leu | Leu | Ala | Leu | Leu | Arg | Asp | Gly | Ala | Ile | Asp | Val | Ala | Met | |
| | | | 140 | | | | | 145 | | | | | 150 | | | |

| | | | | | | | | | | | | | | | | |
|---|---|---|---|---|---|---|---|---|---|---|---|---|---|---|---|---|
| atg | gcc | ctg | cct | tct | gag | gca | cca | ggc | atg | aag | gaa | atc | ccc | ctc | tac | 1254 |
| Met | Ala | Leu | Pro | Ser | Glu | Ala | Pro | Gly | Met | Lys | Glu | Ile | Pro | Leu | Tyr | |
| | | 155 | | | | | 160 | | | | | 165 | | | | |

| | | | | | | | | | | | | | | | | |
|---|---|---|---|---|---|---|---|---|---|---|---|---|---|---|---|---|
| gac | gaa | gac | ttt | atc | gtc | gtt | aca | gct | agc | gat | cac | ccc | ttc | gcc | ggc | 1302 |
| Asp | Glu | Asp | Phe | Ile | Val | Val | Thr | Ala | Ser | Asp | His | Pro | Phe | Ala | Gly | |
| | 170 | | | | | 175 | | | | | 180 | | | | | |

| | | | | | | | | | | | | | | | | |
|---|---|---|---|---|---|---|---|---|---|---|---|---|---|---|---|---|
| cgc | caa | gac | tta | gaa | cta | tcc | gcc | tta | gaa | gac | ctc | gat | ctg | ctg | ctt | 1350 |
| Arg | Gln | Asp | Leu | Glu | Leu | Ser | Ala | Leu | Glu | Asp | Leu | Asp | Leu | Leu | Leu | |
| 185 | | | | | 190 | | | | | 195 | | | | | 200 | |

| | | | | | | | | | | | | | | | | |
|---|---|---|---|---|---|---|---|---|---|---|---|---|---|---|---|---|
| ctc | gac | gac | gga | cac | tgc | ctc | cac | gac | caa | att | gtg | gac | ctg | tgc | cgc | 1398 |
| Leu | Asp | Asp | Gly | His | Cys | Leu | His | Asp | Gln | Ile | Val | Asp | Leu | Cys | Arg | |
| | | | | 205 | | | | | 210 | | | | | 215 | | |

| | | | | | | | | | | | | | | | | |
|---|---|---|---|---|---|---|---|---|---|---|---|---|---|---|---|---|
| cgc | gga | gac | atc | aac | ccc | att | agc | tcc | act | act | gct | gtc | acc | cgc | gca | 1446 |
| Arg | Gly | Asp | Ile | Asn | Pro | Ile | Ser | Ser | Thr | Thr | Ala | Val | Thr | Arg | Ala | |
| | | | 220 | | | | | 225 | | | | | 230 | | | |

| | | | | | | | | | | | | | | | | |
|---|---|---|---|---|---|---|---|---|---|---|---|---|---|---|---|---|
| tcc | agc | ctt | acc | acc | gtc | atg | cag | ctc | gtc | gtc | gcc | ggc | ctt | gga | tcc | 1494 |
| Ser | Ser | Leu | Thr | Thr | Val | Met | Gln | Leu | Val | Val | Ala | Gly | Leu | Gly | Ser | |
| | | 235 | | | | | 240 | | | | | 245 | | | | |

| | | | | | | | | | | | | | | | | |
|---|---|---|---|---|---|---|---|---|---|---|---|---|---|---|---|---|
| acc | ttg | gtc | cca | atc | agc | gca | atc | cca | tgg | gaa | tgc | acc | cga | cca | gga | 1542 |

```
Thr Leu Val Pro Ile Ser Ala Ile Pro Trp Glu Cys Thr Arg Pro Gly
    250                 255                 260 ctg gca aca gcc aac ttc aac tct gat gtc acc gca aac cgc cgc att    1590
Leu Ala Thr Ala Asn Phe Asn Ser Asp Val Thr Ala Asn Arg Arg Ile
265                 270                 275                 280 gga ttg gtg tac cgt tcc tct tct cgc gcc gaa gag ttc gaa cag        1638
Gly Leu Val Tyr Arg Ser Ser Ser Arg Ala Glu Glu Phe Glu Gln
                285                 290                 295 ttt gca ctc att ttg cag cgc gct ttc caa gaa gcc gtc gcg ctt gct    1686
Phe Ala Leu Ile Leu Gln Arg Ala Phe Gln Glu Ala Val Ala Leu Ala
                300                 305                 310 gcc tca act ggc atc acc ttg aag caa aat gtc gcg gta gcg cag        1731
Ala Ser Thr Gly Ile Thr Leu Lys Gln Asn Val Ala Val Ala Gln
                315                 320                 325 taagttttc tagaggtttt ccagagtcag ctacaagcaa aaagcccttt ccattgatgc    1791
acaccaacgt gagattcaag ggaaagggct ttattgattg cagaatgcct actgcattag   1851
cggcgctcca ccgaatatt tccaccactg atctggcggt aaatatgaac ggtagacagc    1911
atcattactg gcagcacgat gatcaggccg aaaccgatcg tgaaaatacc gatgatgagt   1971
gtggcaaacc cgccaaccag ggagaacagc aacaacattg gtagttgcg cagcgagtcc    2031 ttgaaaccag tttgaacagc gcttcctgca gtgtggtgac catcagctgt gtagtacacc   2091
cagtaggagt acagaggatt gatgaagaac aacaccaggt agacgatgaa gaacatgcct   2151
aaaccgctgt tattgaccto aacggtaccg gcagcgtcat aaacgacac cagattttga   2211 gtgagaaaag tggtgaaggt gcccaggatg atgccgaaga tacccagccc caccatcaga   2271
atcactgttt gaccaacatt gatgggttta agaaatcac cgaagcgaac tttgtgtcca    2331
tcaacagaaa gcagtgcacc cgcatgacg caaatggtta ttgcgaaggt gatgattccg    2391
atagctacgt tcaacagggt ctcggaaacc gaaaaaccag aagtcgtcgt gcccgcatta   2451
gggtcgatca aaaatgataa gtagccaagc aac                                2484

<210> SEQ ID NO 4
<211> LENGTH: 327
<212> TYPE: PRT
<213> ORGANISM: Corynebacterium glutamicum

<400> SEQUENCE: 4

Met Ser Asn Lys Glu Tyr Arg Pro Thr Leu Ala Gln Leu Arg Thr Phe
1               5                   10                  15

Val Thr Ile Ala Glu Cys Lys His Phe Gly Thr Ala Ala Thr Lys Leu
                20                  25                  30

Ser Ile Ser Gln Pro Ser Leu Ser Gln Ala Leu Val Ala Leu Glu Thr
            35                  40                  45

Gly Leu Gly Val Gln Leu Ile Glu Arg Ser Thr Arg Lys Val Ile Val
        50                  55                  60

Thr Pro Ala Gly Glu Lys Leu Leu Pro Phe Ala Lys Ser Thr Leu Asp
65                  70                  75                  80

Ala Ala Glu Ser Phe Leu Ser His Ala Lys Gly Ala Asn Gly Ser Leu
                85                  90                  95

Thr Gly Pro Leu Thr Val Gly Ile Ile Pro Thr Ala Ala Pro Tyr Ile
            100                 105                 110

Leu Pro Ser Met Leu Ser Ile Val Asp Glu Glu Tyr Pro Asp Leu Glu
        115                 120                 125

Pro His Ile Val Glu Asp Gln Thr Lys His Leu Leu Ala Leu Leu Arg
    130                 135                 140
```

-continued

```
Asp Gly Ala Ile Asp Val Ala Met Met Ala Leu Pro Ser Glu Ala Pro
145                 150                 155                 160

Gly Met Lys Glu Ile Pro Leu Tyr Asp Glu Asp Phe Ile Val Val Thr
            165                 170                 175

Ala Ser Asp His Pro Phe Ala Gly Arg Gln Asp Leu Glu Leu Ser Ala
            180                 185                 190

Leu Glu Asp Leu Asp Leu Leu Leu Asp Asp Gly His Cys Leu His
        195                 200                 205

Asp Gln Ile Val Asp Leu Cys Arg Arg Gly Asp Ile Asn Pro Ile Ser
210                 215                 220

Ser Thr Thr Ala Val Thr Arg Ala Ser Ser Leu Thr Thr Val Met Gln
225                 230                 235                 240

Leu Val Val Ala Gly Leu Gly Ser Thr Leu Val Pro Ile Ser Ala Ile
                245                 250                 255

Pro Trp Glu Cys Thr Arg Pro Gly Leu Ala Thr Ala Asn Phe Asn Ser
                260                 265                 270

Asp Val Thr Ala Asn Arg Arg Ile Gly Leu Val Tyr Arg Ser Ser Ser
            275                 280                 285

Ser Arg Ala Glu Glu Phe Glu Gln Phe Ala Leu Ile Leu Gln Arg Ala
        290                 295                 300

Phe Gln Glu Ala Val Ala Leu Ala Ala Ser Thr Gly Ile Thr Leu Lys
305                 310                 315                 320

Gln Asn Val Ala Val Ala Gln
                325
```

```
<210> SEQ ID NO 5
<211> LENGTH: 984
<212> TYPE: DNA
<213> ORGANISM: Corynebacterium glutamicum
<220> FEATURE:
<221> NAME/KEY: CDS
<222> LOCATION: (1)..(981)
<223> OTHER INFORMATION: oxyR allele
<220> FEATURE:
<221> NAME/KEY: mutation
<222> LOCATION: (266)..(266)
<223> OTHER INFORMATION: C -> T transition
<220> FEATURE:
<221> NAME/KEY: misc_feature
<222> LOCATION: (731)..(731)
<223> OTHER INFORMATION: cytosine

<400> SEQUENCE: 5 atg agc aat aaa gag tac cgg ccc aca ctc gcc cag ctt cgc acc ttt    48
Met Ser Asn Lys Glu Tyr Arg Pro Thr Leu Ala Gln Leu Arg Thr Phe
1               5                   10                  15 gtc acc atc gca gaa tgc aag cac ttt ggt act gct gcc acc aag ctg    96
Val Thr Ile Ala Glu Cys Lys His Phe Gly Thr Ala Ala Thr Lys Leu
            20                  25                  30 tcc att tcg cag cca tcc ctc tcc cag gca ctt gtc gca tta gaa aca   144
Ser Ile Ser Gln Pro Ser Leu Ser Gln Ala Leu Val Ala Leu Glu Thr
        35                  40                  45 ggc ctg gga gtt cag ctg att gaa cgc tcc acc cgc aag gtc att gtc   192
Gly Leu Gly Val Gln Leu Ile Glu Arg Ser Thr Arg Lys Val Ile Val
50                  55                  60 acc cca gcg ggc gag aag ttg ctg cca ttc gcc aaa tcc acc ctt gac   240
Thr Pro Ala Gly Glu Lys Leu Leu Pro Phe Ala Lys Ser Thr Leu Asp
65                  70                  75                  80 gcg gcg gag tct ttc ctc tcc cac gtc aag ggc gcc aac ggt tcg ctc   288
Ala Ala Glu Ser Phe Leu Ser His Val Lys Gly Ala Asn Gly Ser Leu
                85                  90                  95
```

```
act gga ccg ttg acc gta ggc atc atc ccc acg gcg gct cct tac att    336
Thr Gly Pro Leu Thr Val Gly Ile Ile Pro Thr Ala Ala Pro Tyr Ile
        100                 105                 110 ttg ccg tca atg ctg tcc atc gtg gat gaa gaa tat cca gat ctg gaa    384
Leu Pro Ser Met Leu Ser Ile Val Asp Glu Glu Tyr Pro Asp Leu Glu
    115                 120                 125 cct cac atc gtc gag gac caa acc aag cat ctt ctc gcg ttg ctg cgc    432
Pro His Ile Val Glu Asp Gln Thr Lys His Leu Leu Ala Leu Leu Arg
130                 135                 140 gac ggc gcc atc gac gtc gcc atg atg gcc ctg cct tct gag gca cca    480
Asp Gly Ala Ile Asp Val Ala Met Met Ala Leu Pro Ser Glu Ala Pro
145                 150                 155                 160 ggc atg aag gaa atc ccc ctc tac gac gaa gac ttt atc gtc gtt aca    528
Gly Met Lys Glu Ile Pro Leu Tyr Asp Glu Asp Phe Ile Val Val Thr
                165                 170                 175 gct agc gat cac ccc ttc gcc ggc cgc caa gac tta gaa cta tcc gcc    576
Ala Ser Asp His Pro Phe Ala Gly Arg Gln Asp Leu Glu Leu Ser Ala
                180                 185                 190 tta gaa gac ctc gat ctg ctg ctt ctc gac gac gga cac tgc ctc cac    624
Leu Glu Asp Leu Asp Leu Leu Leu Leu Asp Asp Gly His Cys Leu His
            195                 200                 205 gac caa att gtg gac ctg tgc cgc cgc gga gac atc aac ccc att agc    672
Asp Gln Ile Val Asp Leu Cys Arg Arg Gly Asp Ile Asn Pro Ile Ser
210                 215                 220 tcc act act gct gtc acc cgc gca tcc agc ctt acc acc gtc atg cag    720
Ser Thr Thr Ala Val Thr Arg Ala Ser Ser Leu Thr Thr Val Met Gln
225                 230                 235                 240 ctc gtc gtc gcc ggc ctt gga tcc acc ttg gtc cca atc agc gca atc    768
Leu Val Val Ala Gly Leu Gly Ser Thr Leu Val Pro Ile Ser Ala Ile
                245                 250                 255 cca tgg gaa tgc acc cga cca gga ctg gca aca gcc aac ttc aac tct    816
Pro Trp Glu Cys Thr Arg Pro Gly Leu Ala Thr Ala Asn Phe Asn Ser
                260                 265                 270 gat gtc acc gca aac cgc cgc att gga ttg gtg tac cgt tcc tct tct    864
Asp Val Thr Ala Asn Arg Arg Ile Gly Leu Val Tyr Arg Ser Ser Ser
            275                 280                 285 tct cgc gcc gaa gag ttc gaa cag ttt gca ctc att ttg cag cgc gct    912
Ser Arg Ala Glu Glu Phe Glu Gln Phe Ala Leu Ile Leu Gln Arg Ala
290                 295                 300 ttc caa gaa gcc gtc gcg ctt gct gcc tca act ggc atc acc ttg aag    960
Phe Gln Glu Ala Val Ala Leu Ala Ala Ser Thr Gly Ile Thr Leu Lys
305                 310                 315                 320 caa aat gtc gcg gta gcg cag taa                                    984
Gln Asn Val Ala Val Ala Gln
                325

<210> SEQ ID NO 6
<211> LENGTH: 327
<212> TYPE: PRT
<213> ORGANISM: Corynebacterium glutamicum

<400> SEQUENCE: 6

Met Ser Asn Lys Glu Tyr Arg Pro Thr Leu Ala Gln Leu Arg Thr Phe
1               5                   10                  15

Val Thr Ile Ala Glu Cys Lys His Phe Gly Thr Ala Ala Thr Lys Leu
            20                  25                  30

Ser Ile Ser Gln Pro Ser Leu Ser Gln Ala Leu Val Ala Leu Glu Thr
        35                  40                  45

Gly Leu Gly Val Gln Leu Ile Glu Arg Ser Thr Arg Lys Val Ile Val
    50                  55                  60
```

```
Thr Pro Ala Gly Glu Lys Leu Leu Pro Phe Ala Lys Ser Thr Leu Asp
 65                  70                  75                  80

Ala Ala Glu Ser Phe Leu Ser His Val Lys Gly Ala Asn Gly Ser Leu
                 85                  90                  95

Thr Gly Pro Leu Thr Val Gly Ile Ile Pro Thr Ala Ala Pro Tyr Ile
            100                 105                 110

Leu Pro Ser Met Leu Ser Ile Val Asp Glu Glu Tyr Pro Asp Leu Glu
        115                 120                 125

Pro His Ile Val Glu Asp Gln Thr Lys His Leu Leu Ala Leu Leu Arg
    130                 135                 140

Asp Gly Ala Ile Asp Val Ala Met Met Ala Leu Pro Ser Glu Ala Pro
145                 150                 155                 160

Gly Met Lys Glu Ile Pro Leu Tyr Asp Glu Asp Phe Ile Val Val Thr
                165                 170                 175

Ala Ser Asp His Pro Phe Ala Gly Arg Gln Asp Leu Glu Leu Ser Ala
            180                 185                 190

Leu Glu Asp Leu Asp Leu Leu Leu Asp Asp Gly His Cys Leu His
        195                 200                 205

Asp Gln Ile Val Asp Leu Cys Arg Arg Gly Asp Ile Asn Pro Ile Ser
210                 215                 220

Ser Thr Thr Ala Val Thr Arg Ala Ser Ser Leu Thr Thr Val Met Gln
225                 230                 235                 240

Leu Val Val Ala Gly Leu Gly Ser Thr Leu Val Pro Ile Ser Ala Ile
                245                 250                 255

Pro Trp Glu Cys Thr Arg Pro Gly Leu Ala Thr Ala Asn Phe Asn Ser
            260                 265                 270

Asp Val Thr Ala Asn Arg Arg Ile Gly Leu Val Tyr Arg Ser Ser Ser
        275                 280                 285

Ser Arg Ala Glu Glu Phe Glu Gln Phe Ala Leu Ile Leu Gln Arg Ala
    290                 295                 300

Phe Gln Glu Ala Val Ala Leu Ala Ala Ser Thr Gly Ile Thr Leu Lys
305                 310                 315                 320

Gln Asn Val Ala Val Ala Gln
                325

<210> SEQ ID NO 7
<211> LENGTH: 2484
<212> TYPE: DNA
<213> ORGANISM: Corynebacterium glutamicum
<220> FEATURE:
<221> NAME/KEY: misc_feature
<222> LOCATION: (1)..(750)
<223> OTHER INFORMATION: nucleotide sequence upstream of CDS
<220> FEATURE:
<221> NAME/KEY: primer_bind
<222> LOCATION: (271)..(290)
<223> OTHER INFORMATION: bindung site for primer oxyR_XL_A1
<220> FEATURE:
<221> NAME/KEY: CDS
<222> LOCATION: (751)..(1731)
<223> OTHER INFORMATION: oxyR allele
<220> FEATURE:
<221> NAME/KEY: mutation
<222> LOCATION: (1016)..(1016)
<223> OTHER INFORMATION: C -> T transition
<220> FEATURE:
<221> NAME/KEY: misc_feature
<222> LOCATION: (1481)..(1481)
<223> OTHER INFORMATION: cytosine
<220> FEATURE:
<221> NAME/KEY: misc_feature
<222> LOCATION: (1732)..(2484)
<223> OTHER INFORMATION: nucleotide sequence downstream of CDS
```

<220> FEATURE:
<221> NAME/KEY: primer_bind
<222> LOCATION: (1834)..(1853)
<223> OTHER INFORMATION: bindung site for primer oxyR_XL_E1

<400> SEQUENCE: 7

```
cctacggtgt ggccaggtca gagggtgttg cgctgcgcta cctcaccgat gcctggcgta      60
ctctccaaca ctcactgcct acggaagctc gcaccgagga acttgatgat gttgtggtgt     120
ggttgggcga actgatcaaa caggtcgact cctccctggt ggatgagtgg gctcagatgg     180
cggatccaga agcaccgatc agcaaggaag cgctggaacg agagctcgcc ttcggcgtgg     240
aagacccaac agcacttacc gccaaccgca gggcatttac catcatggtg cgcaacgcca     300
tgttccgcct tgtggagcta tttgcttatg aaaaggaaga tcagcttagt cagatgactg     360
aatacctgga tgaggctcct gatttcggtg ctgcgatgga tgcgtacttt gatgaatatg     420
cggatcttga taccggcccg gcagctcgtg gaccagagtt cttcaaggta gagcacacgg     480
gaagaatgtg ggaggtgcgt caggtggtga aggatccaga aggtgataat tccttcgcgt     540 tgttgccac cattgatctt gatgcctctg atgatgcagg tgaggtgcgt tttggatcgc     600
tgtcgattga ccacaactag gggtttgcgt cgaaaagcaa gcacgcctgg tgcctgattt     660
gagcggtttt acctatggcg ctttggcgcc gtcaaactgt cccagcgatt tcattattat     720
tttcgtgcat tcaccgttat agttataggc atg agc aat aaa gag tac cgg ccc     774
                                Met Ser Asn Lys Glu Tyr Arg Pro
                                 1               5 aca ctc gcc cag ctt cgc acc ttt gtc acc atc gca gaa tgc aag cac      822
Thr Leu Ala Gln Leu Arg Thr Phe Val Thr Ile Ala Glu Cys Lys His
     10                  15                  20 ttt ggt act gct gcc acc aag ctg tcc att tcg cag cca tcc ctc tcc      870
Phe Gly Thr Ala Ala Thr Lys Leu Ser Ile Ser Gln Pro Ser Leu Ser
 25                  30                  35                  40 cag gca ctt gtc gca tta gaa aca ggc ctg gga gtt cag ctg att gaa      918
Gln Ala Leu Val Ala Leu Glu Thr Gly Leu Gly Val Gln Leu Ile Glu
                 45                  50                  55 cgc tcc acc cgc aag gtc att gtc acc cca gcg ggc gag aag ttg ctg      966
Arg Ser Thr Arg Lys Val Ile Val Thr Pro Ala Gly Glu Lys Leu Leu
             60                  65                  70 cca ttc gcc aaa tcc acc ctt gac gcg gcg gag tct ttc ctc tcc cac     1014
Pro Phe Ala Lys Ser Thr Leu Asp Ala Ala Glu Ser Phe Leu Ser His
         75                  80                  85 gtc aag ggc gcc aac ggt tcg ctc act gga ccg ttg acc gta ggc atc     1062
Val Lys Gly Ala Asn Gly Ser Leu Thr Gly Pro Leu Thr Val Gly Ile
     90                  95                 100 atc ccc acg gcg gct cct tac att ttg ccg tca atg ctg tcc atc gtg     1110
Ile Pro Thr Ala Ala Pro Tyr Ile Leu Pro Ser Met Leu Ser Ile Val
105                 110                 115                 120 gat gaa gaa tat cca gat ctg gaa cct cac atc gtc gag gac caa acc     1158
Asp Glu Glu Tyr Pro Asp Leu Glu Pro His Ile Val Glu Asp Gln Thr
                125                 130                 135 aag cat ctt ctc gcg ttg ctg cgc gac ggc gcc atc gac gtc gcc atg     1206
Lys His Leu Leu Ala Leu Leu Arg Asp Gly Ala Ile Asp Val Ala Met
            140                 145                 150 atg gcc ctg cct tct gag gca cca ggc atg aag gaa atc ccc ctc tac     1254
Met Ala Leu Pro Ser Glu Ala Pro Gly Met Lys Glu Ile Pro Leu Tyr
        155                 160                 165 gac gaa gac ttt atc gtc gtt aca gct agc gat cac ccc ttc gcc ggc     1302
Asp Glu Asp Phe Ile Val Val Thr Ala Ser Asp His Pro Phe Ala Gly
    170                 175                 180 cgc caa gac tta gaa cta tcc gcc tta gaa gac ctc gat ctg ctg ctt     1350
```

```
Arg Gln Asp Leu Glu Leu Ser Ala Leu Glu Asp Leu Asp Leu Leu Leu
185                 190                 195                 200 ctc gac gac gga cac tgc ctc cac gac caa att gtg gac ctg tgc cgc       1398
Leu Asp Asp Gly His Cys Leu His Asp Gln Ile Val Asp Leu Cys Arg
                205                 210                 215 cgc gga gac atc aac ccc att agc tcc act act gct gtc acc cgc gca       1446
Arg Gly Asp Ile Asn Pro Ile Ser Ser Thr Thr Ala Val Thr Arg Ala
            220                 225                 230 tcc agc ctt acc acc gtc atg cag ctc gtc gtc gcc ggc ctt gga tcc       1494
Ser Ser Leu Thr Thr Val Met Gln Leu Val Val Ala Gly Leu Gly Ser
        235                 240                 245 acc ttg gtc cca atc agc gca atc cca tgg gaa tgc acc cga cca gga       1542
Thr Leu Val Pro Ile Ser Ala Ile Pro Trp Glu Cys Thr Arg Pro Gly
    250                 255                 260 ctg gca aca gcc aac ttc aac tct gat gtc acc gca aac cgc cgc att       1590
Leu Ala Thr Ala Asn Phe Asn Ser Asp Val Thr Ala Asn Arg Arg Ile
265                 270                 275                 280 gga ttg gtg tac cgt tcc tct tct tct cgc gcc gaa gag ttc gaa cag       1638
Gly Leu Val Tyr Arg Ser Ser Ser Ser Arg Ala Glu Glu Phe Glu Gln
                285                 290                 295 ttt gca ctc att ttg cag cgc gct ttc caa gaa gcc gtc gcg ctt gct       1686
Phe Ala Leu Ile Leu Gln Arg Ala Phe Gln Glu Ala Val Ala Leu Ala
                300                 305                 310 gcc tca act ggc atc acc ttg aag caa aat gtc gcg gta gcg cag           1731
Ala Ser Thr Gly Ile Thr Leu Lys Gln Asn Val Ala Val Ala Gln
        315                 320                 325 taagttttc tagaggtttt ccagagtcag ctacaagcaa aaagcccttt ccattgatgc      1791
acaccaacgt gagattcaag ggaaagggct ttattgattg cagaatgcct actgcattag     1851
cggcgctcca ccggaatatt tccaccactg atctggcggt aaatatgaac ggtagacagc     1911
atcattactg gcagcacgat gatcaggccg aaaccgatcg tgaaaatacc gatgatgagt     1971
gtggcaaacc cgccaaccag ggagaacagc aacaacattg gtagttgcg cagcgagtcc      2031 ttgaaaccag tttgaacagc gcttcctgca gtgtggtgac catcagctgt gtagtacacc     2091
cagtaggagt acagaggatt gatgaagaac aacaccaggt agacgatgaa gaacatgcct     2151
aaaccgctgt tattgacctc aacggtaccg gcagcgtcat taaacgacac cagattttga     2211
gtgagaaaag tggtgaaggt gcccaggatg atgccgaaga tacccagccc accatcaga     2271 atcactgttt gaccaacatt gatgggttta agaaatcac cgaagcgaac tttgtgtcca     2331
tcaacagaaa gcagtgcacc gcgcatgacg caaatggtta ttgcgaaggt gatgattccg     2391
atagctacgt tcaacagggt ctcggaaacc gaaaaaccag aagtcgtcgt gcccgcatta     2451
gggtcgatca aaaatgataa gtagccaagc aac                                 2484

<210> SEQ ID NO 8
<211> LENGTH: 327
<212> TYPE: PRT
<213> ORGANISM: Corynebacterium glutamicum

<400> SEQUENCE: 8

Met Ser Asn Lys Glu Tyr Arg Pro Thr Leu Ala Gln Leu Arg Thr Phe
1               5                   10                  15

Val Thr Ile Ala Glu Cys Lys His Phe Gly Thr Ala Ala Thr Lys Leu
            20                  25                  30

Ser Ile Ser Gln Pro Ser Leu Ser Gln Ala Leu Val Ala Leu Glu Thr
        35                  40                  45

Gly Leu Gly Val Gln Leu Ile Glu Arg Ser Thr Arg Lys Val Ile Val
    50                  55                  60
```

Thr Pro Ala Gly Glu Lys Leu Leu Pro Phe Ala Lys Ser Thr Leu Asp
 65                  70                  75                  80

Ala Ala Glu Ser Phe Leu Ser His Val Lys Gly Ala Asn Gly Ser Leu
             85                  90                  95

Thr Gly Pro Leu Thr Val Gly Ile Ile Pro Thr Ala Ala Pro Tyr Ile
        100                 105                 110

Leu Pro Ser Met Leu Ser Ile Val Asp Glu Glu Tyr Pro Asp Leu Glu
    115                 120                 125

Pro His Ile Val Glu Asp Gln Thr Lys His Leu Leu Ala Leu Leu Arg
130                 135                 140

Asp Gly Ala Ile Asp Val Ala Met Met Ala Leu Pro Ser Glu Ala Pro
145                 150                 155                 160

Gly Met Lys Glu Ile Pro Leu Tyr Asp Glu Asp Phe Ile Val Val Thr
                165                 170                 175

Ala Ser Asp His Pro Phe Ala Gly Arg Gln Asp Leu Glu Leu Ser Ala
            180                 185                 190

Leu Glu Asp Leu Asp Leu Leu Leu Asp Asp Gly His Cys Leu His
        195                 200                 205

Asp Gln Ile Val Asp Leu Cys Arg Arg Gly Asp Ile Asn Pro Ile Ser
    210                 215                 220

Ser Thr Thr Ala Val Thr Arg Ala Ser Ser Leu Thr Thr Val Met Gln
225                 230                 235                 240

Leu Val Val Ala Gly Leu Gly Ser Thr Leu Val Pro Ile Ser Ala Ile
                245                 250                 255

Pro Trp Glu Cys Thr Arg Pro Gly Leu Ala Thr Ala Asn Phe Asn Ser
            260                 265                 270

Asp Val Thr Ala Asn Arg Arg Ile Gly Leu Val Tyr Arg Ser Ser Ser
        275                 280                 285

Ser Arg Ala Glu Glu Phe Glu Gln Phe Ala Leu Ile Leu Gln Arg Ala
    290                 295                 300

Phe Gln Glu Ala Val Ala Leu Ala Ala Ser Thr Gly Ile Thr Leu Lys
305                 310                 315                 320

Gln Asn Val Ala Val Ala Gln
                325

<210> SEQ ID NO 9
<211> LENGTH: 28
<212> TYPE: DNA
<213> ORGANISM: artificial sequence based on Corynebacterium glutamicum
<220> FEATURE:
<223> OTHER INFORMATION: Primer oxyR_XL_A1
<220> FEATURE:
<221> NAME/KEY: misc_feature
<222> LOCATION: (1)..(2)
<220> FEATURE:
<221> NAME/KEY: misc_structure
<222> LOCATION: (3)..(8)
<223> OTHER INFORMATION: EcoRI restriction site

<400> SEQUENCE: 9
gcgaattcgg gcatttacca tcatggtg                                      28

<210> SEQ ID NO 10
<211> LENGTH: 28
<212> TYPE: DNA
<213> ORGANISM: artificial sequence based on Corynebacterium glutamicum
<220> FEATURE:
<223> OTHER INFORMATION: Primer oxyR_XL_E1
<220> FEATURE:
<221> NAME/KEY: misc_feature

```
<222> LOCATION: (1)..(2)
<220> FEATURE:
<221> NAME/KEY: misc_structure
<222> LOCATION: (3)..(8)
<223> OTHER INFORMATION: EcoRI restriction site

<400> SEQUENCE: 10
gcgaattccg ctaatgcagt aggcattc                                          28

<210> SEQ ID NO 11
<211> LENGTH: 1263
<212> TYPE: DNA
<213> ORGANISM: Corynebacterium glutamicum
<220> FEATURE:
<221> NAME/KEY: CDS
<222> LOCATION: (1)..(1263)
<223> OTHER INFORMATION: lysC wild type gene

<400> SEQUENCE: 11
```

| | | | | | | | | | | | | | | | | |
|---|---|---|---|---|---|---|---|---|---|---|---|---|---|---|---|---|
| gtg | gcc | ctg | gtc | gta | cag | aaa | tat | ggc | ggt | tcc | tcg | ctt | gag | agt | gcg | 48 |
| Val | Ala | Leu | Val | Val | Gln | Lys | Tyr | Gly | Gly | Ser | Ser | Leu | Glu | Ser | Ala | |
| 1 | | | | 5 | | | | | 10 | | | | | 15 | | |
| gaa | cgc | att | aga | aac | gtc | gct | gaa | cgg | atc | gtt | gcc | acc | aag | aag | gct | 96 |
| Glu | Arg | Ile | Arg | Asn | Val | Ala | Glu | Arg | Ile | Val | Ala | Thr | Lys | Lys | Ala | |
| | | | 20 | | | | | 25 | | | | | 30 | | | |
| gga | aat | gat | gtc | gtg | gtt | gtc | tgc | tcc | gca | atg | gga | gac | acc | acg | gat | 144 |
| Gly | Asn | Asp | Val | Val | Val | Val | Cys | Ser | Ala | Met | Gly | Asp | Thr | Thr | Asp | |
| | 35 | | | | | 40 | | | | | 45 | | | | | |
| gaa | ctt | cta | gaa | ctt | gca | gcg | gca | gtg | aat | ccc | gtt | ccg | cca | gct | cgt | 192 |
| Glu | Leu | Leu | Glu | Leu | Ala | Ala | Ala | Val | Asn | Pro | Val | Pro | Pro | Ala | Arg | |
| 50 | | | | | 55 | | | | | 60 | | | | | | |
| gaa | atg | gat | atg | ctc | ctg | act | gct | ggt | gag | cgt | att | tct | aac | gct | ctc | 240 |
| Glu | Met | Asp | Met | Leu | Leu | Thr | Ala | Gly | Glu | Arg | Ile | Ser | Asn | Ala | Leu | |
| 65 | | | | | 70 | | | | | 75 | | | | | 80 | |
| gtc | gcc | atg | gct | att | gag | tcc | ctt | ggc | gca | gaa | gcc | caa | tct | ttc | acg | 288 |
| Val | Ala | Met | Ala | Ile | Glu | Ser | Leu | Gly | Ala | Glu | Ala | Gln | Ser | Phe | Thr | |
| | | | | 85 | | | | | 90 | | | | | 95 | | |
| ggc | tct | cag | gct | ggt | gtg | ctc | acc | acc | gag | cgc | cac | gga | aac | gca | cgc | 336 |
| Gly | Ser | Gln | Ala | Gly | Val | Leu | Thr | Thr | Glu | Arg | His | Gly | Asn | Ala | Arg | |
| | | | 100 | | | | | 105 | | | | | 110 | | | |
| att | gtt | gat | gtc | act | cca | ggt | cgt | gtg | cgt | gaa | gca | ctc | gat | gag | ggc | 384 |
| Ile | Val | Asp | Val | Thr | Pro | Gly | Arg | Val | Arg | Glu | Ala | Leu | Asp | Glu | Gly | |
| | 115 | | | | | 120 | | | | | 125 | | | | | |
| aag | atc | tgc | att | gtt | gct | ggt | ttc | cag | ggt | gtt | aat | aaa | gaa | acc | cgc | 432 |
| Lys | Ile | Cys | Ile | Val | Ala | Gly | Phe | Gln | Gly | Val | Asn | Lys | Glu | Thr | Arg | |
| 130 | | | | | 135 | | | | | 140 | | | | | | |
| gat | gtc | acc | acg | ttg | ggt | cgt | ggt | ggt | tct | gac | acc | act | gca | gtt | gcg | 480 |
| Asp | Val | Thr | Thr | Leu | Gly | Arg | Gly | Gly | Ser | Asp | Thr | Thr | Ala | Val | Ala | |
| 145 | | | | | 150 | | | | | 155 | | | | | 160 | |
| ttg | gca | gct | gct | ttg | aac | gct | gat | gtg | tgt | gag | att | tac | tcg | gac | gtt | 528 |
| Leu | Ala | Ala | Ala | Leu | Asn | Ala | Asp | Val | Cys | Glu | Ile | Tyr | Ser | Asp | Val | |
| | | | | 165 | | | | | 170 | | | | | 175 | | |
| gac | ggt | gtg | tat | acc | gct | gac | ccg | cgc | atc | gtt | cct | aat | gca | cag | aag | 576 |
| Asp | Gly | Val | Tyr | Thr | Ala | Asp | Pro | Arg | Ile | Val | Pro | Asn | Ala | Gln | Lys | |
| | | | 180 | | | | | 185 | | | | | 190 | | | |
| ctg | gaa | aag | ctc | agc | ttc | gaa | gaa | atg | ctg | gaa | ctt | gct | gct | gtt | ggc | 624 |
| Leu | Glu | Lys | Leu | Ser | Phe | Glu | Glu | Met | Leu | Glu | Leu | Ala | Ala | Val | Gly | |
| | 195 | | | | | 200 | | | | | 205 | | | | | |
| tcc | aag | att | ttg | gtg | ctg | cgc | agt | gtt | gaa | tac | gct | cgt | gca | ttc | aat | 672 |
| Ser | Lys | Ile | Leu | Val | Leu | Arg | Ser | Val | Glu | Tyr | Ala | Arg | Ala | Phe | Asn | |
| 210 | | | | | 215 | | | | | 220 | | | | | | |
| gtg | cca | ctt | cgc | gta | cgc | tcg | tct | tat | agt | aat | gat | ccc | ggc | act | ttg | 720 |
| Val | Pro | Leu | Arg | Val | Arg | Ser | Ser | Tyr | Ser | Asn | Asp | Pro | Gly | Thr | Leu | |

```
                     225                 230                 235                 240
att gcc ggc tct atg gag gat att cct gtg gaa gaa gca gtc ctt acc            768
Ile Ala Gly Ser Met Glu Asp Ile Pro Val Glu Glu Ala Val Leu Thr
                    245                 250                 255 ggt gtc gca acc gac aag tcc gaa gcc aaa gta acc gtt ctg ggt att            816
Gly Val Ala Thr Asp Lys Ser Glu Ala Lys Val Thr Val Leu Gly Ile
                260                 265                 270 tcc gat aag cca ggc gag gct gcg aag gtt ttc cgt gcg ttg gct gat            864
Ser Asp Lys Pro Gly Glu Ala Ala Lys Val Phe Arg Ala Leu Ala Asp
            275                 280                 285 gca gaa atc aac att gac atg gtt ctg cag aac gtc tct tct gta gaa            912
Ala Glu Ile Asn Ile Asp Met Val Leu Gln Asn Val Ser Ser Val Glu
        290                 295                 300 gac ggc acc acc gac atc acc ttc acc tgc cct cgt tcc gac ggc cgc            960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc           1008
Arg Ala Met Glu Ile Leu Lys Lys Leu Gln Val Gln Gly Asn Trp Thr
                    325                 330                 335 aat gtg ctt tac gac gac cag gtc ggc aaa gtc tcc ctc gtg ggt gct           1056
Asn Val Leu Tyr Asp Asp Gln Val Gly Lys Val Ser Leu Val Gly Ala
                340                 345                 350 ggc atg aag tct cac cca ggt gtt acc gca gag ttc atg gaa gct ctg           1104
Gly Met Lys Ser His Pro Gly Val Thr Ala Glu Phe Met Glu Ala Leu
            355                 360                 365 cgc gat gtc aac gtg aac atc gaa ttg att tcc acc tct gag att cgt           1152
Arg Asp Val Asn Val Asn Ile Glu Leu Ile Ser Thr Ser Glu Ile Arg
        370                 375                 380 att tcc gtg ctg atc cgt gaa gat gat ctg gat gct gct gca cgt gca           1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat           1248
Leu His Glu Gln Phe Gln Leu Gly Gly Glu Asp Glu Ala Val Val Tyr
                    405                 410                 415 gca ggc acc gga cgc                                                       1263
Ala Gly Thr Gly Arg
                420

<210> SEQ ID NO 12
<211> LENGTH: 421
<212> TYPE: PRT
<213> ORGANISM: Corynebacterium glutamicum

<400> SEQUENCE: 12

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
```

```
                115                 120                 125
Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 13
<211> LENGTH: 1311
<212> TYPE: DNA
<213> ORGANISM: Corynebacterium glutamicum
<220> FEATURE:
<221> NAME/KEY: CDS
<222> LOCATION: (1)..(1308)
<223> OTHER INFORMATION: ilvA wild type gene

<400> SEQUENCE: 13 atg agt gaa aca tac gtg tct gag aaa agt cca gga gtg atg gct agc      48
Met Ser Glu Thr Tyr Val Ser Glu Lys Ser Pro Gly Val Met Ala Ser
1               5                   10                  15 gga gcg gag ctg att cgt gcc gcc gac att caa acg gcg cag gca cga      96
Gly Ala Glu Leu Ile Arg Ala Ala Asp Ile Gln Thr Ala Gln Ala Arg
                20                  25                  30 att tcc tcc gtc att gca cca act cca ttg cag tat tgc cct cgt ctt     144
```

```
        Ile Ser Ser Val Ile Ala Pro Thr Pro Leu Gln Tyr Cys Pro Arg Leu
                 35                  40                  45 tct gag gaa acc gga gcg gaa atc tac ctt aag cgt gag gat ctg cag         192
Ser Glu Glu Thr Gly Ala Glu Ile Tyr Leu Lys Arg Glu Asp Leu Gln
 50                  55                  60 gat gtt cgt tcc tac aag atc cgc ggt gcg ctg aac tct gga gcg cag         240
Asp Val Arg Ser Tyr Lys Ile Arg Gly Ala Leu Asn Ser Gly Ala Gln
 65                  70                  75                  80 ctc acc caa gag cag cgc gat gca ggt atc gtt gcc gca tct gca ggt         288
Leu Thr Gln Glu Gln Arg Asp Ala Gly Ile Val Ala Ala Ser Ala Gly
                 85                  90                  95 aac cat gcc cag ggc gtg gcc tat gtg tgc aag tcc ttg ggc gtt cag         336
Asn His Ala Gln Gly Val Ala Tyr Val Cys Lys Ser Leu Gly Val Gln
                100                 105                 110 gga cgc atc tat gtt cct gtg cag act cca aag caa aag cgt gac cgc         384
Gly Arg Ile Tyr Val Pro Val Gln Thr Pro Lys Gln Lys Arg Asp Arg
            115                 120                 125 atc atg gtt cac ggc gga gag ttt gtc tcc ttg gtg gtc act ggc aat         432
Ile Met Val His Gly Gly Glu Phe Val Ser Leu Val Val Thr Gly Asn
130                 135                 140 aac ttc gac gaa gca tcg gct gca gcg cat gaa gat gca gag cgc acc         480
Asn Phe Asp Glu Ala Ser Ala Ala Ala His Glu Asp Ala Glu Arg Thr
145                 150                 155                 160 ggc gca acg ctg atc gag cct ttc gat gct cgc aac acc gtc atc ggt         528
Gly Ala Thr Leu Ile Glu Pro Phe Asp Ala Arg Asn Thr Val Ile Gly
                165                 170                 175 cag ggc acc gtg gct gct gag atc ttg tcg cag ctg act tcc atg ggc         576
Gln Gly Thr Val Ala Ala Glu Ile Leu Ser Gln Leu Thr Ser Met Gly
            180                 185                 190 aag agt gca gat cac gtg atg gtt cca gtc ggc ggt ggc gga ctt ctt         624
Lys Ser Ala Asp His Val Met Val Pro Val Gly Gly Gly Gly Leu Leu
        195                 200                 205 gca ggt gtg gtc agc tac atg gct gat atg gca cct cgc act gcg atc         672
Ala Gly Val Val Ser Tyr Met Ala Asp Met Ala Pro Arg Thr Ala Ile
    210                 215                 220 gtt ggt atc gaa cca gcg gga gca gca tcc atg cag gct gca ttg cac         720
Val Gly Ile Glu Pro Ala Gly Ala Ala Ser Met Gln Ala Ala Leu His
225                 230                 235                 240 aat ggt gga cca atc act ttg gag act gtt gat ccc ttt gtg gac ggc         768
Asn Gly Gly Pro Ile Thr Leu Glu Thr Val Asp Pro Phe Val Asp Gly
                245                 250                 255 gca gca gtc aaa cgt gtc gga gat ctc aac tac acc atc gtg gag aag         816
Ala Ala Val Lys Arg Val Gly Asp Leu Asn Tyr Thr Ile Val Glu Lys
            260                 265                 270 aac cag ggt cgc gtg cac atg atg agc gcg acc gag ggc gct gtg tgt         864
Asn Gln Gly Arg Val His Met Met Ser Ala Thr Glu Gly Ala Val Cys
        275                 280                 285 act gag atg ctc gat ctt tac caa aac gaa ggc atc atc gcg gag cct         912
Thr Glu Met Leu Asp Leu Tyr Gln Asn Glu Gly Ile Ile Ala Glu Pro
    290                 295                 300 gct ggc gcg ctg tct atc gct ggg ttg aag gaa atg tcc ttt gca cct         960
Ala Gly Ala Leu Ser Ile Ala Gly Leu Lys Glu Met Ser Phe Ala Pro
305                 310                 315                 320 ggt tct gtc gtg gtg tgc atc atc tct ggt ggc aac aac gat gtg ctg         1008
Gly Ser Val Val Val Cys Ile Ile Ser Gly Gly Asn Asn Asp Val Leu
                325                 330                 335 cgt tat gcg gaa atc gct gag cgc tcc ttg gtg cac cgc ggt ttg aag         1056
Arg Tyr Ala Glu Ile Ala Glu Arg Ser Leu Val His Arg Gly Leu Lys
            340                 345                 350 cac tac ttc ttg gtg aac ttc ccg caa aag cct ggt cag ttg cgt cac         1104
```

```
                His Tyr Phe Leu Val Asn Phe Pro Gln Lys Pro Gly Gln Leu Arg His
                    355                 360                 365 ttc ctg gaa gat atc ctg gga ccg gat gat gac atc acg ctg ttt gag         1152
Phe Leu Glu Asp Ile Leu Gly Pro Asp Asp Asp Ile Thr Leu Phe Glu
370                 375                 380 tac ctc aag cgc aac aac cgt gag acc ggt act gcg ttg gtg ggt att         1200
Tyr Leu Lys Arg Asn Asn Arg Glu Thr Gly Thr Ala Leu Val Gly Ile
385                 390                 395                 400 cac ttg agt gaa gca tca gga ttg gat tct ttg ctg gaa cgt atg gag         1248
His Leu Ser Glu Ala Ser Gly Leu Asp Ser Leu Leu Glu Arg Met Glu
                405                 410                 415 gaa tcg gca att gat tcc cgt cgc ctc gag ccg ggc acc cct gag tac         1296
Glu Ser Ala Ile Asp Ser Arg Arg Leu Glu Pro Gly Thr Pro Glu Tyr
            420                 425                 430 gaa tac ttg acc taa                                                      1311
Glu Tyr Leu Thr
            435

<210> SEQ ID NO 14
<211> LENGTH: 436
<212> TYPE: PRT
<213> ORGANISM: Corynebacterium glutamicum

<400> SEQUENCE: 14

Met Ser Glu Thr Tyr Val Ser Glu Lys Ser Pro Gly Val Met Ala Ser
1               5                   10                  15

Gly Ala Glu Leu Ile Arg Ala Ala Asp Ile Gln Thr Ala Gln Ala Arg
            20                  25                  30

Ile Ser Ser Val Ile Ala Pro Thr Pro Leu Gln Tyr Cys Pro Arg Leu
        35                  40                  45

Ser Glu Glu Thr Gly Ala Glu Ile Tyr Leu Lys Arg Glu Asp Leu Gln
    50                  55                  60

Asp Val Arg Ser Tyr Lys Ile Arg Gly Ala Leu Asn Ser Gly Ala Gln
65                  70                  75                  80

Leu Thr Gln Glu Gln Arg Asp Ala Gly Ile Val Ala Ala Ser Ala Gly
                85                  90                  95

Asn His Ala Gln Gly Val Ala Tyr Val Cys Lys Ser Leu Gly Val Gln
            100                 105                 110

Gly Arg Ile Tyr Val Pro Val Gln Thr Pro Lys Gln Lys Arg Asp Arg
        115                 120                 125

Ile Met Val His Gly Gly Glu Phe Val Ser Leu Val Val Thr Gly Asn
    130                 135                 140

Asn Phe Asp Glu Ala Ser Ala Ala His Glu Asp Ala Glu Arg Thr
145                 150                 155                 160

Gly Ala Thr Leu Ile Glu Pro Phe Asp Ala Arg Asn Thr Val Ile Gly
                165                 170                 175

Gln Gly Thr Val Ala Ala Glu Ile Leu Ser Gln Leu Thr Ser Met Gly
            180                 185                 190

Lys Ser Ala Asp His Val Met Val Pro Val Gly Gly Gly Gly Leu Leu
        195                 200                 205

Ala Gly Val Val Ser Tyr Met Ala Asp Met Ala Pro Arg Thr Ala Ile
    210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Ala Val Lys Arg Val Gly Asp Leu Asn Tyr Thr Ile Val Glu Lys
```

-continued

```
                    260                 265                 270
Asn Gln Gly Arg Val His Met Met Ser Ala Thr Glu Gly Ala Val Cys
                275                 280                 285

Thr Glu Met Leu Asp Leu Tyr Gln Asn Glu Gly Ile Ile Ala Glu Pro
            290                 295                 300

Ala Gly Ala Leu Ser Ile Ala Gly Leu Lys Glu Met Ser Phe Ala Pro
305                 310                 315                 320

Gly Ser Val Val Cys Ile Ile Ser Gly Asn Asn Asp Val Leu
                325                 330                 335

Arg Tyr Ala Glu Ile Ala Glu Arg Ser Leu Val His Arg Gly Leu Lys
            340                 345                 350

His Tyr Phe Leu Val Asn Phe Pro Gln Lys Pro Gly Gln Leu Arg His
        355                 360                 365

Phe Leu Glu Asp Ile Leu Gly Pro Asp Asp Asp Ile Thr Leu Phe Glu
            370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
                405                 410                 415

Glu Ser Ala Ile Asp Ser Arg Arg Leu Glu Pro Gly Thr Pro Glu Tyr
            420                 425                 430

Glu Tyr Leu Thr
        435

<210> SEQ ID NO 15
<211> LENGTH: 1599
<212> TYPE: DNA
<213> ORGANISM: Corynebacterium glutamicum
<220> FEATURE:
<221> NAME/KEY: misc_feature
<222> LOCATION: (1)..(1599)
<223> OTHER INFORMATION: PCR product
<220> FEATURE:
<221> NAME/KEY: misc_feature
<222> LOCATION: (1)..(2)
<220> FEATURE:
<221> NAME/KEY: misc_structure
<222> LOCATION: (3)..(8)
<223> OTHER INFORMATION: EcoRI restriction site
<220> FEATURE:
<221> NAME/KEY: CDS
<222> LOCATION: (489)..(1469)
<223> OTHER INFORMATION: oxyR allele
<220> FEATURE:
<221> NAME/KEY: mutation
<222> LOCATION: (754)..(754)
<223> OTHER INFORMATION: C -> T transition
<220> FEATURE:
<221> NAME/KEY: misc_feature
<222> LOCATION: (1219)..(1219)
<223> OTHER INFORMATION: cytosine
<220> FEATURE:
<221> NAME/KEY: misc_structure
<222> LOCATION: (1592)..(1597)
<223> OTHER INFORMATION: EcoRI restriction site
<220> FEATURE:
<221> NAME/KEY: misc_feature
<222> LOCATION: (1598)..(1599)

<400> SEQUENCE: 15
gcgaattcgg gcatttacca tcatggtgcg caacgccatg ttccgccttg tggagctatt      60
tgcttatgaa aaggaagatc agcttagtca gatgactgaa tacctggatg aggctcctga     120
tttcggtgct gcgatggatg cgtactttga tgaatatgcg gatcttgata ccggcccggc     180
agctcgtgga ccagagttct tcaaggtaga gcacacggga agaatgtggg aggtgcgtca     240
```

```
ggtggtgaag gatccagaag gtgataattc cttcgcgttt gttgccacca ttgatcttga    300
tgcctctgat gatgcaggtg aggtgcgttt tggatcgctg tcgattgacc acaactaggg    360
gtttgcgtcg aaaagcaagc acgcctggtg cctgatttga gcggttttac ctatggcgct    420
ttggcgccgt caaactgtcc cagcgatttc attattattt tcgtgcattc accgttatag    480 ttataggc atg agc aat aaa gag tac cgg ccc aca ctc gcc cag ctt cgc     530
         Met Ser Asn Lys Glu Tyr Arg Pro Thr Leu Ala Gln Leu Arg
          1               5                  10 acc ttt gtc acc atc gca gaa tgc aag cac ttt ggt act gct gcc acc      578
Thr Phe Val Thr Ile Ala Glu Cys Lys His Phe Gly Thr Ala Ala Thr
15              20                  25                  30 aag ctg tcc att tcg cag cca tcc ctc tcc cag gca ctt gtc gca tta      626
Lys Leu Ser Ile Ser Gln Pro Ser Leu Ser Gln Ala Leu Val Ala Leu
                35                  40                  45 gaa aca ggc ctg gga gtt cag ctg att gaa cgc tcc acc cgc aag gtc      674
Glu Thr Gly Leu Gly Val Gln Leu Ile Glu Arg Ser Thr Arg Lys Val
            50                  55                  60 att gtc acc cca gcg ggc gag aag ttg ctg cca ttc gcc aaa tcc acc      722
Ile Val Thr Pro Ala Gly Glu Lys Leu Leu Pro Phe Ala Lys Ser Thr
        65                  70                  75 ctt gac gcg gcg gag tct ttc ctc tcc cac gtc aag ggc gcc aac ggt      770
Leu Asp Ala Ala Glu Ser Phe Leu Ser His Val Lys Gly Ala Asn Gly
80                  85                  90 tcg ctc act gga ccg ttg acc gta ggc atc atc ccc acg gcg gct cct      818
Ser Leu Thr Gly Pro Leu Thr Val Gly Ile Ile Pro Thr Ala Ala Pro
95              100                 105                 110 tac att ttg ccg tca atg ctg tcc atc gtg gat gaa gaa tat cca gat      866
Tyr Ile Leu Pro Ser Met Leu Ser Ile Val Asp Glu Glu Tyr Pro Asp
                115                 120                 125 ctg gaa cct cac atc gtc gag gac caa acc aag cat ctc ctc gcg ttg      914
Leu Glu Pro His Ile Val Glu Asp Gln Thr Lys His Leu Leu Ala Leu
            130                 135                 140 ctg cgc gac ggc gcc atc gac gtc gcc atg atg gcc ctg cct tct gag      962
Leu Arg Asp Gly Ala Ile Asp Val Ala Met Met Ala Leu Pro Ser Glu
        145                 150                 155 gca cca ggc atg aag gaa atc ccc ctc tac gac gaa gac ttt atc gtc     1010
Ala Pro Gly Met Lys Glu Ile Pro Leu Tyr Asp Glu Asp Phe Ile Val
160                 165                 170 gtt aca gct agc gat cac ccc ttc gcc ggc cgc caa gac tta gaa cta     1058
Val Thr Ala Ser Asp His Pro Phe Ala Gly Arg Gln Asp Leu Glu Leu
175                 180                 185                 190 tcc gcc tta gaa gac ctc gat ctg ctg ctt ctc gac gac gga cac tgc     1106
Ser Ala Leu Glu Asp Leu Asp Leu Leu Leu Leu Asp Asp Gly His Cys
                195                 200                 205 ctc cac gac caa att gtg gac ctg tgc cgc cgc gga gac atc aac ccc     1154
Leu His Asp Gln Ile Val Asp Leu Cys Arg Arg Gly Asp Ile Asn Pro
            210                 215                 220 att agc tcc act act gct gtc acc cgc gca tcc agc ctt acc acc gtc     1202
Ile Ser Ser Thr Thr Ala Val Thr Arg Ala Ser Ser Leu Thr Thr Val
        225                 230                 235 atg cag ctc gtc gtc gcc ggc ctt gga tcc acc ttg gtc cca atc agc     1250
Met Gln Leu Val Val Ala Gly Leu Gly Ser Thr Leu Val Pro Ile Ser
240                 245                 250 gca atc cca tgg gaa tgc acc cga cca gga ctg gca aca gcc aac ttc     1298
Ala Ile Pro Trp Glu Cys Thr Arg Pro Gly Leu Ala Thr Ala Asn Phe
255                 260                 265                 270 aac tct gat gtc acc gca aac cgc cgc att gga ttg gtg tac cgt tcc     1346
Asn Ser Asp Val Thr Ala Asn Arg Arg Ile Gly Leu Val Tyr Arg Ser
                275                 280                 285
```

```
tct tct tct cgc gcc gaa gag ttc gaa cag ttt gca ctc att ttg cag    1394
Ser Ser Ser Arg Ala Glu Glu Phe Glu Gln Phe Ala Leu Ile Leu Gln
            290                 295                 300 cgc gct ttc caa gaa gcc gtc gcg ctt gct gcc tca act ggc atc acc    1442
Arg Ala Phe Gln Glu Ala Val Ala Leu Ala Ala Ser Thr Gly Ile Thr
        305                 310                 315 ttg aag caa aat gtc gcg gta gcg cag taagttttc tagaggtttt           1489
Leu Lys Gln Asn Val Ala Val Ala Gln
    320                 325 ccagagtcag ctacaagcaa aaagcccttt ccattgatgc acaccaacgt gagattcaag  1549
ggaaagggct ttattgattg cagaatgcct actgcattag cggaattcgc             1599

<210> SEQ ID NO 16
<211> LENGTH: 327
<212> TYPE: PRT
<213> ORGANISM: Corynebacterium glutamicum

<400> SEQUENCE: 16

Met Ser Asn Lys Glu Tyr Arg Pro Thr Leu Ala Gln Leu Arg Thr Phe
1               5                   10                  15

Val Thr Ile Ala Glu Cys Lys His Phe Gly Thr Ala Ala Lys Leu
            20                  25                  30

Ser Ile Ser Gln Pro Ser Leu Ser Gln Ala Leu Val Ala Leu Glu Thr
        35                  40                  45

Gly Leu Gly Val Gln Leu Ile Glu Arg Ser Thr Arg Lys Val Ile Val
    50                  55                  60

Thr Pro Ala Gly Glu Lys Leu Leu Pro Phe Ala Lys Ser Thr Leu Asp
65                  70                  75                  80

Ala Ala Glu Ser Phe Leu Ser His Val Lys Gly Ala Asn Gly Ser Leu
                85                  90                  95

Thr Gly Pro Leu Thr Val Gly Ile Ile Pro Thr Ala Ala Pro Tyr Ile
            100                 105                 110

Leu Pro Ser Met Leu Ser Ile Val Asp Glu Glu Tyr Pro Asp Leu Glu
        115                 120                 125

Pro His Ile Val Glu Asp Gln Thr Lys His Leu Leu Ala Leu Leu Arg
    130                 135                 140

Asp Gly Ala Ile Asp Val Ala Met Met Ala Leu Pro Ser Glu Ala Pro
145                 150                 155                 160

Gly Met Lys Glu Ile Pro Leu Tyr Asp Glu Asp Phe Ile Val Val Thr
                165                 170                 175

Ala Ser Asp His Pro Phe Ala Gly Arg Gln Asp Leu Glu Leu Ser Ala
            180                 185                 190

Leu Glu Asp Leu Asp Leu Leu Leu Asp Asp Gly His Cys Leu His
        195                 200                 205

Asp Gln Ile Val Asp Leu Cys Arg Arg Gly Asp Ile Asn Pro Ile Ser
    210                 215                 220

Ser Thr Thr Ala Val Thr Arg Ala Ser Ser Leu Thr Thr Val Met Gln
225                 230                 235                 240

Leu Val Val Ala Gly Leu Gly Ser Thr Leu Val Pro Ile Ser Ala Ile
                245                 250                 255

Pro Trp Glu Cys Thr Arg Pro Gly Leu Ala Thr Ala Asn Phe Asn Ser
            260                 265                 270

Asp Val Thr Ala Asn Arg Arg Ile Gly Leu Val Tyr Arg Ser Ser Ser
        275                 280                 285

Ser Arg Ala Glu Glu Phe Glu Gln Phe Ala Leu Ile Leu Gln Arg Ala
```

```
                290             295             300
Phe Gln Glu Ala Val Ala Leu Ala Ala Ser Thr Gly Ile Thr Leu Lys
305                 310                 315                 320

Gln Asn Val Ala Val Ala Gln
                325

<210> SEQ ID NO 17
<211> LENGTH: 117
<212> TYPE: DNA
<213> ORGANISM: Corynebacterium glutamicum
<220> FEATURE:
<221> NAME/KEY: CDS
<222> LOCATION: (1)..(117)
<223> OTHER INFORMATION: part of the coding region of the oxyR allele
<220> FEATURE:
<221> NAME/KEY: misc_feature
<222> LOCATION: (58)..(60)
<223> OTHER INFORMATION: n is a, c, g, or t

<400> SEQUENCE: 17 aag ttg ctg cca ttc gcc aaa tcc acc ctt gac gcg gcg gag tct ttc      48
Lys Leu Leu Pro Phe Ala Lys Ser Thr Leu Asp Ala Ala Glu Ser Phe
1               5                   10                  15 ctc tcc cac nnn aag ggc gcc aac ggt tcg ctc act gga ccg ttg acc      96
Leu Ser His Xaa Lys Gly Ala Asn Gly Ser Leu Thr Gly Pro Leu Thr
            20                  25                  30 gta ggc atc atc ccc acg gcg                                         117
Val Gly Ile Ile Pro Thr Ala
        35

<210> SEQ ID NO 18
<211> LENGTH: 39
<212> TYPE: PRT
<213> ORGANISM: Corynebacterium glutamicum
<220> FEATURE:
<221> NAME/KEY: misc_feature
<222> LOCATION: (20)..(20)
<223> OTHER INFORMATION: The 'Xaa' at location 20 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 18

Lys Leu Leu Pro Phe Ala Lys Ser Thr Leu Asp Ala Ala Glu Ser Phe
1               5                   10                  15

Leu Ser His Xaa Lys Gly Ala Asn Gly Ser Leu Thr Gly Pro Leu Thr
            20                  25                  30

Val Gly Ile Ile Pro Thr Ala
        35

<210> SEQ ID NO 19
<211> LENGTH: 117
<212> TYPE: DNA
<213> ORGANISM: Corynebacterium glutamicum
<220> FEATURE:
<221> NAME/KEY: CDS
<222> LOCATION: (1)..(117)
<223> OTHER INFORMATION: part of the coding region of the oxyR allele

<400> SEQUENCE: 19 aag ttg ctg cca ttc gcc aaa tcc acc ctt gac gcg gcg gag tct ttc      48
Lys Leu Leu Pro Phe Ala Lys Ser Thr Leu Asp Ala Ala Glu Ser Phe
1               5                   10                  15 ctc tcc cac gtc aag ggc gcc aac ggt tcg ctc act gga ccg ttg acc      96
Leu Ser His Val Lys Gly Ala Asn Gly Ser Leu Thr Gly Pro Leu Thr
            20                  25                  30 gta ggc atc atc ccc acg gcg                                         117
```

Val Gly Ile Ile Pro Thr Ala
        35

<210> SEQ ID NO 20
<211> LENGTH: 39
<212> TYPE: PRT
<213> ORGANISM: Corynebacterium glutamicum

<400> SEQUENCE: 20

Lys Leu Leu Pro Phe Ala Lys Ser Thr Leu Asp Ala Ala Glu Ser Phe
1               5                   10                  15

Leu Ser His Val Lys Gly Ala Asn Gly Ser Leu Thr Gly Pro Leu Thr
            20                  25                  30

Val Gly Ile Ile Pro Thr Ala
        35

<210> SEQ ID NO 21
<211> LENGTH: 984
<212> TYPE: DNA
<213> ORGANISM: Corynebacterium glutamicum
<220> FEATURE:
<221> NAME/KEY: CDS
<222> LOCATION: (1)..(981)
<223> OTHER INFORMATION: oxyR allele
<220> FEATURE:
<221> NAME/KEY: mutation
<222> LOCATION: (266)..(266)
<223> OTHER INFORMATION: C -> T transition
<220> FEATURE:
<221> NAME/KEY: mutation
<222> LOCATION: (731)..(731)
<223> OTHER INFORMATION: C -> T transition

<400> SEQUENCE: 21 atg agc aat aaa gag tac cgg ccc aca ctc gcc cag ctt cgc acc ttt      48
Met Ser Asn Lys Glu Tyr Arg Pro Thr Leu Ala Gln Leu Arg Thr Phe
1               5                   10                  15 gtc acc atc gca gaa tgc aag cac ttt ggt act gct gcc acc aag ctg      96
Val Thr Ile Ala Glu Cys Lys His Phe Gly Thr Ala Ala Thr Lys Leu
            20                  25                  30 tcc att tcg cag cca tcc ctc tcc cag gca ctt gtc gca tta gaa aca     144
Ser Ile Ser Gln Pro Ser Leu Ser Gln Ala Leu Val Ala Leu Glu Thr
        35                  40                  45 ggc ctg gga gtt cag ctg att gaa cgc tcc acc cgc aag gtc att gtc     192
Gly Leu Gly Val Gln Leu Ile Glu Arg Ser Thr Arg Lys Val Ile Val
    50                  55                  60 acc cca gcg ggc gag aag ttg ctg cca ttc gcc aaa tcc acc ctt gac     240
Thr Pro Ala Gly Glu Lys Leu Leu Pro Phe Ala Lys Ser Thr Leu Asp
65                  70                  75                  80 gcg gcg gag tct ttc ctc tcc cac gtc aag ggc gcc aac ggt tcg ctc     288
Ala Ala Glu Ser Phe Leu Ser His Val Lys Gly Ala Asn Gly Ser Leu
                85                  90                  95 act gga ccg ttg acc gta ggc atc atc ccc acg gcg gct cct tac att     336
Thr Gly Pro Leu Thr Val Gly Ile Ile Pro Thr Ala Ala Pro Tyr Ile
            100                 105                 110 ttg ccg tca atg ctg tcc atc gtg gat gaa gaa tat cca gat ctg gaa     384
Leu Pro Ser Met Leu Ser Ile Val Asp Glu Glu Tyr Pro Asp Leu Glu
        115                 120                 125 cct cac atc gtc gag gac caa acc aag cat ctt ctc gcg ttg ctg cgc     432
Pro His Ile Val Glu Asp Gln Thr Lys His Leu Leu Ala Leu Leu Arg
    130                 135                 140 gac ggc gcc atc gac gtc gcc atg atg gcc ctg cct tct gag gca cca     480
Asp Gly Ala Ile Asp Val Ala Met Met Ala Leu Pro Ser Glu Ala Pro
145                 150                 155                 160

```
ggc atg aag gaa atc ccc ctc tac gac gaa gac ttt atc gtc gtt aca    528
Gly Met Lys Glu Ile Pro Leu Tyr Asp Glu Asp Phe Ile Val Val Thr
            165                 170                 175 gct agc gat cac ccc ttc gcc ggc cgc caa gac tta gaa cta tcc gcc    576
Ala Ser Asp His Pro Phe Ala Gly Arg Gln Asp Leu Glu Leu Ser Ala
        180                 185                 190 tta gaa gac ctc gat ctg ctt ctc gac gac gga cac tgc ctc cac        624
Leu Glu Asp Leu Asp Leu Leu Leu Asp Asp Gly His Cys Leu His
    195                 200                 205 gac caa att gtg gac ctg tgc cgc cgc gga gac atc aac ccc att agc    672
Asp Gln Ile Val Asp Leu Cys Arg Arg Gly Asp Ile Asn Pro Ile Ser
210                 215                 220 tcc act act gct gtc acc cgc gca tcc agc ctt acc acc gtc atg cag    720
Ser Thr Thr Ala Val Thr Arg Ala Ser Ser Leu Thr Thr Val Met Gln
225                 230                 235                 240 ctc gtc gtc gtc ggc ctt gga tcc acc ttg gtc cca atc agc gca atc    768
Leu Val Val Val Gly Leu Gly Ser Thr Leu Val Pro Ile Ser Ala Ile
                245                 250                 255 cca tgg gaa tgc acc cga cca gga ctg gca aca gcc aac ttc aac tct    816
Pro Trp Glu Cys Thr Arg Pro Gly Leu Ala Thr Ala Asn Phe Asn Ser
            260                 265                 270 gat gtc acc gca aac cgc cgc att gga ttg gtg tac cgt tcc tct tct    864
Asp Val Thr Ala Asn Arg Arg Ile Gly Leu Val Tyr Arg Ser Ser Ser
        275                 280                 285 tct cgc gcc gaa gag ttc gaa cag ttt gca ctc att ttg cag cgc gct    912
Ser Arg Ala Glu Glu Phe Glu Gln Phe Ala Leu Ile Leu Gln Arg Ala
    290                 295                 300 ttc caa gaa gcc gtc gcg ctt gct gcc tca act ggc atc acc ttg aag    960
Phe Gln Glu Ala Val Ala Leu Ala Ala Ser Thr Gly Ile Thr Leu Lys
305                 310                 315                 320 caa aat gtc gcg gta gcg cag taa                                    984
Gln Asn Val Ala Val Ala Gln
                325

<210> SEQ ID NO 22
<211> LENGTH: 327
<212> TYPE: PRT
<213> ORGANISM: Corynebacterium glutamicum

<400> SEQUENCE: 22

Met Ser Asn Lys Glu Tyr Arg Pro Thr Leu Ala Gln Leu Arg Thr Phe
1               5                   10                  15

Val Thr Ile Ala Glu Cys Lys His Phe Gly Thr Ala Ala Thr Lys Leu
            20                  25                  30

Ser Ile Ser Gln Pro Ser Leu Ser Gln Ala Leu Val Ala Leu Glu Thr
        35                  40                  45

Gly Leu Gly Val Gln Leu Ile Glu Arg Ser Thr Arg Lys Val Ile Val
    50                  55                  60

Thr Pro Ala Gly Glu Lys Leu Leu Pro Phe Ala Lys Ser Thr Leu Asp
65                  70                  75                  80

Ala Ala Glu Ser Phe Leu Ser His Val Lys Gly Ala Asn Gly Ser Leu
                85                  90                  95

Thr Gly Pro Leu Thr Val Gly Ile Ile Pro Thr Ala Ala Pro Tyr Ile
            100                 105                 110

Leu Pro Ser Met Leu Ser Ile Val Asp Glu Glu Tyr Pro Asp Leu Glu
        115                 120                 125

Pro His Ile Val Glu Asp Gln Thr Lys His Leu Leu Ala Leu Leu Arg
    130                 135                 140

Asp Gly Ala Ile Asp Val Ala Met Met Ala Leu Pro Ser Glu Ala Pro
```

```
145                 150                 155                 160
Gly Met Lys Glu Ile Pro Leu Tyr Asp Glu Asp Phe Ile Val Val Thr
                165                 170                 175

Ala Ser Asp His Pro Phe Ala Gly Arg Gln Asp Leu Glu Leu Ser Ala
            180                 185                 190

Leu Glu Asp Leu Asp Leu Leu Leu Asp Asp Gly His Cys Leu His
        195                 200                 205

Asp Gln Ile Val Asp Leu Cys Arg Arg Gly Asp Ile Asn Pro Ile Ser
    210                 215                 220

Ser Thr Thr Ala Val Thr Arg Ala Ser Ser Leu Thr Thr Val Met Gln
225                 230                 235                 240

Leu Val Val Val Gly Leu Gly Ser Thr Leu Val Pro Ile Ser Ala Ile
                245                 250                 255

Pro Trp Glu Cys Thr Arg Pro Gly Leu Ala Thr Ala Asn Phe Asn Ser
            260                 265                 270

Asp Val Thr Ala Asn Arg Arg Ile Gly Leu Val Tyr Arg Ser Ser
        275                 280                 285

Ser Arg Ala Glu Glu Phe Glu Gln Phe Ala Leu Ile Leu Gln Arg Ala
    290                 295                 300

Phe Gln Glu Ala Val Ala Leu Ala Ala Ser Thr Gly Ile Thr Leu Lys
305                 310                 315                 320

Gln Asn Val Ala Val Ala Gln
                325

<210> SEQ ID NO 23
<211> LENGTH: 698
<212> TYPE: DNA
<213> ORGANISM: Corynebacterium glutamicum
<220> FEATURE:
<221> NAME/KEY: misc_feature
<222> LOCATION: (167)..(179)
<220> FEATURE:
<221> NAME/KEY: CDS
<222> LOCATION: (201)..(695)
<223> OTHER INFORMATION: dps wild type gene

<400> SEQUENCE: 23
tcttggtgag ttccccagct agtcgatgaa tcacgtgtcc ttcaggcata atcaccaacc      60
ttagtagccg gtgtgccgat tgataaaaaa actaagcgtg gcctgcggga atcggcactt     120
tcaggatagg acaacctaat ataaataagc ttaggctaag ggccggtgac aatttatcaa     180
gcagtgctat aataggggtc atg gca aac tac aca gtc cct gga atc aac gag    233
                        Met Ala Asn Tyr Thr Val Pro Gly Ile Asn Glu
                         1               5                  10 aat gac gca aag cag ctt att gat gga ctg cag gag cgt ctc acc gac     281
Asn Asp Ala Lys Gln Leu Ile Asp Gly Leu Gln Glu Arg Leu Thr Asp
            15                  20                  25 tac aac gat ctt cac ctc atc ttg aag cac gtg cac tgg aac gtc act     329
Tyr Asn Asp Leu His Leu Ile Leu Lys His Val His Trp Asn Val Thr
        30                  35                  40 ggc ccc aac ttc att gct gtt cac gaa atg ctc gac cca cag gtt gac     377
Gly Pro Asn Phe Ile Ala Val His Glu Met Leu Asp Pro Gln Val Asp
    45                  50                  55 ctt gtt cgt ggc tat gct gac gaa gtt gca gag cgc att tcc acc ctc     425
Leu Val Arg Gly Tyr Ala Asp Glu Val Ala Glu Arg Ile Ser Thr Leu
60                  65                  70                  75 gga ggc gca cca gtt gga acc cca gaa ggc cac gtt gct gac cgc acc     473
Gly Gly Ala Pro Val Gly Thr Pro Glu Gly His Val Ala Asp Arg Thr
                80                  85                  90
```

```
cca ctg caa tat gag cgc aat gcc gga aat gtc caa gca cac ctc act    521
Pro Leu Gln Tyr Glu Arg Asn Ala Gly Asn Val Gln Ala His Leu Thr
        95                  100                 105 gac ctc aat cgc gtg tac acc caa gtg ctg acc gga gtt cgc gag tcc    569
Asp Leu Asn Arg Val Tyr Thr Gln Val Leu Thr Gly Val Arg Glu Ser
        110                 115                 120 atg gca tca gcc ggc cca gtg gat cca gta act gaa gac atc tac atc    617
Met Ala Ser Ala Gly Pro Val Asp Pro Val Thr Glu Asp Ile Tyr Ile
        125                 130                 135 agc cag gcc gcg gag ctg gag aaa ttc cag tgg ttc atc cgc gca cac    665
Ser Gln Ala Ala Glu Leu Glu Lys Phe Gln Trp Phe Ile Arg Ala His
140                 145                 150                 155 att gtt gat gta gac gga aac atc caa gag taa                        698
Ile Val Asp Val Asp Gly Asn Ile Gln Glu
                160                 165

<210> SEQ ID NO 24
<211> LENGTH: 165
<212> TYPE: PRT
<213> ORGANISM: Corynebacterium glutamicum

<400> SEQUENCE: 24

Met Ala Asn Tyr Thr Val Pro Gly Ile Asn Glu Asn Asp Ala Lys Gln
1               5                   10                  15

Leu Ile Asp Gly Leu Gln Glu Arg Leu Thr Asp Tyr Asn Asp Leu His
            20                  25                  30

Leu Ile Leu Lys His Val His Trp Asn Val Thr Gly Pro Asn Phe Ile
        35                  40                  45

Ala Val His Glu Met Leu Asp Pro Gln Val Asp Leu Val Arg Gly Tyr
    50                  55                  60

Ala Asp Glu Val Ala Glu Arg Ile Ser Thr Leu Gly Gly Ala Pro Val
65                  70                  75                  80

Gly Thr Pro Glu Gly His Val Ala Asp Arg Thr Pro Leu Gln Tyr Glu
                85                  90                  95

Arg Asn Ala Gly Asn Val Gln Ala His Leu Thr Asp Leu Asn Arg Val
            100                 105                 110

Tyr Thr Gln Val Leu Thr Gly Val Arg Glu Ser Met Ala Ser Ala Gly
        115                 120                 125

Pro Val Asp Pro Val Thr Glu Asp Ile Tyr Ile Ser Gln Ala Ala Glu
    130                 135                 140

Leu Glu Lys Phe Gln Trp Phe Ile Arg Ala His Ile Val Asp Val Asp
145                 150                 155                 160

Gly Asn Ile Gln Glu
                165
```

ALLELES OF THE OXYR GENE FROM CORYNEFORM BACTERIA

CROSS-REFERENCE TO RELATED APPLICATIONS

This application is a divisional of U.S. patent application Ser. No. 11/937,888, filed 9 Nov. 2007 now U.S. Pat. No. 7,910,715, allowed, and claims the benefit of DE 102006054202.9, filed 17 Nov. 2006, both of which are herein incorporated by reference in their entirety.

SEQUENCE LISTING REFERENCE

The sequence listing for this application has been submitted in U.S. patent application Ser. No. 11/937,888 via EFS-Web as a text file entitled "Sequence_listing.txt" created 8 Nov. 2007, 78.9 kb, which is herein incorporated by reference in its entirety, and is replaced with the sequence listing submitted in U.S. patent application Ser. No. 11/937,888 via EFS-Web as a text file entitled "20080609_032301_520 seq_ST25.txt" created 9 Jun. 2008, 80.3 kb, which is herein incorporated by reference in its entirety.

BACKGROUND OF THE INVENTION

1. Field of the Invention

The invention relates to mutants and alleles of the oxyR gene of coryneform bacteria coding for variants of the OxyR transcription regulator and methods for producing amino acids, especially selected from the group consisting of L-lysine, L-tryptophan, L-proline, L-valine, L-isoleucine and L-homoserine using bacteria which comprise these alleles.

2. Description of the Prior Art

Amino acids are used in human medicine, in the pharmaceutical industry, in the food product industry and very especially in livestock nutrition.

It is known that amino acids are produced by fermentation of strains of coryneform bacteria, especially *Corynebacterium glutamicum*. Because of the great importance, work on improving the production methods is continually being done. Improvements in the methods may be fermentation technology measures such as, for example, stirring and supplying oxygen, or relate to the composition of the nutrient media, such as, for example, the sugar concentration during the fermentation, or the working up to the product form by for example ion exchange chromatography or the intrinsic output properties of the microorganism itself.

The methods used for improving the output properties of these microorganisms are ones of mutagenesis, selection and choice of mutants. The strains obtained in this way are resistant to antimetabolites or are auxotrophic for metabolites of regulatory importance, and produce the amino acids. A known antimetabolite is the lysine analogue S-(2-aminoethyl)-L-cysteine (AEC).

Methods of recombinant DNA technology have likewise been used for some years for strain improvement of L-amino acid-producing strains of *Corynebacterium* by amplifying individual amino acid biosynthesis genes and investigating the effect on amino acid production.

The chromosome of *Corynebacterium glutamicum* was completely sequenced some time ago (Kalinowski et al., Journal of Biotechnology 104, 5-25 (2003)). The chromosome of *Corynebacterium efficiens* has likewise been sequenced (Nishio et al., Genome Res. 13 (7), 1572-1579 (2003)).

Corresponding sequence data can be taken from the public databases. Suitable databases are for example the database of the European Molecular Biologies Laboratories (EMBL, Heidelberg, Germany and Cambridge, UK), the database of the National Center for Biotechnology Information (NCBI, Bethesda, Md., USA), that of the Swiss Institute of Bioinformatics (Swissprot, Geneva, Switzerland), the Protein Information Resource Database (PIR, Washington, D.C., USA) and the DNA Data Bank of Japan (DDBJ, 1111 Yata, Mishima, 411-8540, Japan).

Summarizing descriptions of the genetics, the metabolism and the industrial importance of *Corynebacterium* are to be found in the articles by Ikeda, by Pfefferle et al. and by Mueller and Huebner in the book "Microbial Production of L-Amino Acids" (Advances in Biochemical Engineering 79, (2003), Springer Verlag, Berlin, Germany, editor: T. Scheper), in the special edition "A New Era in *Corynebacterium glutamicum* Biotechnology" of the Journal of Biotechnology (volume 104 (1-3), 2003, editors: A. Puhler and T. Tauch) and in the "Handbook of *Corynebacterium glutamicum*" (editors: L. Eggeling and M. Bott, CRC Press, Taylor & Francis Group, Boca Raton, Fla., USA, 2005).

The nucleotide sequence of the oxyR gene coding for the OxyR transcription regulator of *Corynebacterium glutamicum* is generally available inter alia in the database of the National Center for Biotechnology Information (NCBI) of the National Library of Medicine (Bethesda, Md., USA) under the access number AF697215. It can furthermore be found in the Patent Application EP1108790 as sequence No. 2114.

U.S. Pat. No. 6,916,636 reports the effect of overexpression of the OxyR transcription regulator on amino acid production.

For improved clarity, the nucleotide sequence of the oxyR gene coding for the OxyR transcription regulator from the wild type of *Corynebacterium glutamicum* ("wild-type gene") according to the data of the NCBI database is depicted in SEQ ID NO:1, and the amino acid sequence of the encoded OxyR transcription regulator resulting therefrom is depicted in SEQ ID NO:2 and 4. Nucleotide sequences located upstream and downstream are additionally indicated in SEQ ID NO:3.

SUMMARY OF THE INVENTION

The present invention provides novel measures for the improved production of amino acids, especially selected from the group consisting of L-lysine, L-tryptophan, L-proline, L-valine, L-isoleucine and L-homoserine.

DESCRIPTION OF THE INVENTION

The invention relates to generated and isolated mutants of coryneform bacteria which preferentially secrete amino acids and which comprise a gene or allele which codes for a polypeptide having OxyR transcription regulator activity, characterized in that the polypeptide includes an amino acid sequence in which one of the proteinogenic amino acids except L-alanine is present at position 89 or a corresponding or comparable position of the amino acid sequence. Exchange of L-alanine for L-valine is preferred.

Among the coryneform bacteria, the genus *Corynebacterium* is preferred. In the genus *Corynebacterium*, the following species are preferred as starting strains:

*Corynebacterium efficiens* (type strain DSM44549),
*Corynebacterium glutamicum* (type strain ATCC13032).

*Corynebacterium thermoaminogenes* (for example the strain FERM BP-1539), and

*Corynebacterium ammoniagenes* (type strain ATCC6871), with very particular preference for the species *Corynebacterium glutamicum*.

Some representatives of the species *Corynebacterium glutamicum* are known in the state of the art also under other species designations. These include for example:

*Corynebacterium acetoacidophilum* ATCC13870,
*Corynebacterium lilium* DSM20137,
*Corynebacterium melassecola* ATCC17965.
*Brevibacterium flavum* ATCC14067,
*Brevibacterium lactofermentum* ATCC13869,
*Brevibacterium divaricatum* ATCC14020, and
*Microbacterium ammoniaphilum* ATCC15354.

The term "*Micrococcus glutamicus*" for *Corynebacterium glutamicum* has likewise been in use.

The strains of coryneform bacteria employed for the measures of the invention (starting strains) preferably already have the ability to enrich the desired amino acid in the cell or secrete it into the nutrient medium surrounding it and accumulate it. The term "produce" is also used for this hereinafter. In particular, the strains of coryneform bacteria employed for the measures of the invention have the ability to enrich or to accumulate ≥(at least) 0.25 g/l, ≥0.5 g/l, ≥1.0 g/l, ≥1.5 g/l, ≥2.0 g/l, ≥4 g/l or ≥10 g/l of the desired amino acid in ≤ (at most) 120 hours, ≤96 hours, ≤48 hours, ≤36 hours, ≤24 hours or ≤12 hours in the cell or in the nutrient medium. In this connection, the strains may have been produced by mutagenesis and selection, by recombinant DNA techniques or by a combination of the two methods.

Known representatives of L-lysine-producing or secreting strains of coryneforme bacteria are for example:

*Corynebacterium glutamicum* DM58-1/pDM6 (=DSM4697) described in EP 0 358 940,
*Corynebacterium glutamicum* MH20-22B (=DSM16835) described in Menkel et al. (Applied and Environmental Microbiology 55(3), 684-688 (1989)),
*Corynebacterium glutamicum* AHP-3 (=Ferm BP-7382) described in EP 1 108 790,
*Corynebacterium glutamicum* NRRL B-11474 described in U.S. Pat. No. 4,275,157, and
*Corynebacterium thermoaminogenes* AJ12521 (=FERM BP-3304) described in U.S. Pat. No. 5,250,423.

Known representatives of L-tryptophan-producing or secreting strains of coryneform bacteria are for example:

*Corynebacterium glutamicum* K76 (=Ferm BP-1847) described in U.S. Pat. No. 5,563,052,
*Corynebacterium glutamicum* BPS13 (=Ferm BP-1777) described in U.S. Pat. No. 5,605,818, and
*Corynebacterium glutamicum* Ferm BP-3055 described in U.S. Pat. No. 5,235,940.

Known representatives of L-proline-producing or -secreting strains of coryneform bacteria are for example:

*Brevibacterium lactofermentum* NRRL B-11421 described in U.S. Pat. No. 4,224,409,
*Brevibacterium flavum* NRRL B-11422 described in U.S. Pat. No. 4,224,409,
*Brevibacterium flavum* FERM BP-2214 described in U.S. Pat. No. 5,294,547,
*Corynebacterium glutamicum* NRRL B-11423 described in U.S. Pat. No. 4,224,409,
*Corynebacterium glutamicum* ATCC 21157 described in U.S. Pat. No. 4,444,885,
*Corynebacterium glutamicum* ATCC 21158 described in U.S. Pat. No. 4,444,885,
*Corynebacterium glutamicum* ATCC 21159 described in U.S. Pat. No. 4,444,885,
*Corynebacterium glutamicum* ATCC 21355 described in U.S. Pat. No. 4,444,885, and
*Microbacterium ammoniaphilum* NRRL B-11424 described in U.S. Pat. No. 4,224,409.

Known representatives of L-valine-producing or secreting strains of coryneform bacteria are for example:

*Brevibacterium lactofermentum* FERM BP-1763 described in U.S. Pat. No. 5,188,948,
*Brevibacterium lactofermentum* FERM BP-3007 described in U.S. Pat. No. 5,521,074,
*Corynebacterium glutamicum* FERM BP-3006 described in U.S. Pat. No. 5,521,074, and
*Corynebacterium glutamicum* FERM BP-1764 described in U.S. Pat. No. 5,188,948.

Known representatives of L-isoleucine-producing or secreting strains of coryneform bacteria are for example:

*Brevibacterium flavum* FERM BP-759 described in U.S. Pat. No. 4,656,135,
*Brevibacterium flavum* FERM BP-2215 described in U.S. Pat. No. 5,294,547, and
*Corynebacterium glutamicum* FERM BP-758 described in U.S. Pat. No. 4,656,135.

Known representatives of L-homoserine-producing or secreting strains of coryneform bacteria are for example:

*Micrococcus glutamicus* ATCC 14296 described in U.S. Pat. No. 3,189,526 and
*Micrococcus glutamicus* ATCC 14297 described in U.S. Pat. No. 3,189,526.

Data on the taxonomic classification of strains of this group of bacteria are to be found inter alia in Seiler (Journal of General Microbiology 129, 1433-1477 (1983)), Kinoshita (1985, Glutamic Acid Bacteria, pp 115-142. In: Demain and Solomon (ed), Biology of Industrial Microorganisms. The Benjamin/Cummins Publishing Co., London, UK), Kampfer and Kroppenstedt (Canadian Journal of Microbiology 42, 989-1005 (1996)), Liebl et al. (International Journal of Systematic Bacteriology 41, 255-260 (1991)) and in U.S. Pat. No. 5,250,434.

Strains with the designation "ATCC" can be purchased from the American Type Culture Collection (Manassas, Va., USA). Strains with the designation "DSM" can be purchased from the Deutsche Sammlung von Mikroorganismen und Zellkulturen (DSMZ, Brunswick, Germany). Strains with the designation "NRRL" can be purchased from the Agricultural Research Service Patent Culture Collection (ARS, Peoria, Ill., US). Strains with the designation "FERM" can be purchased from National Institute of Advanced Industrial Science and Technology (AIST Tsukuba Central 6, 1-1-1 Higashi, Tsukuba Ibaraki, Japan).

Chemically, a gene or allele is a polynucleotide. Another term for this is nucleic acid.

The polypeptide which is encoded by the oxyR gene of *Corynebacterium glutamicum* and has OxyR transcription regulator activity belongs to the group of so-called LysR-type transcription regulators (LTTR). A review of LTTRs is to be found in Schell (Annual Reviews in Microbiology 47, 597-626 (1993)).

The OxyR transcription regulator may also be referred to as OxyR polypeptide, OxyR protein or OxyR regulator protein. It has the activity of a DNA binding protein and binds in the promoter region of the dps gene which codes for the starvation-induced DNA protecting protein (Dps). The nucleotide sequence of the dps gene of *Corynebacterium glutamicum* is depicted in SEQ ID NO: 23. The OxyR polypeptide preferably binds to the nucleotide sequence between position 80 and 210, particularly preferably between 110 and 210 and very particularly preferably to the nucleotide sequence between position 167 and 179 of SEQ ID NO: 23.

The binding is detected with the aid of an assay which is known to experts as the electrophoretic mobility shift analysis assay (EMSA) and is described for example by Kerr (Methods in Enzymology, 254: 619-32 (1995)). This entails the DNA fragment to be investigated being amplified by PCR and labeled through the use of modified primers which have a fluorophore at the 5' end of the primer. An example of a fluorophore used is the indocarbocyanine (Cy3). The labeled DNA is mixed with purified OxyR regulator protein, and the effect of the presence of the protein on the mobility of the DNA fragment in the electric field is analyzed by agarose gel electrophoresis followed by fluorescence detection. Further details of the method for the EMSA assay can be consulted inter alia in Rey et al. (Molecular Microbiology 56(4), 871-887 (2005).

Proteinogenic amino acids generally mean the amino acids which occur in natural proteins, that is to say in proteins of microorganisms, plants, animals and humans. In connection with the present invention, proteinogenic amino acids means the group of L-amino acids consisting of L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine and, where appropriate, L-selenocysteine. The L-amino acids likewise include L-homoserine.

The mutants according to the invention preferably secrete the stated proteinogenic amino acids selected from the group consisting of L-lysine, L-tryptophan, L-proline, L-valine, L-isoleucine or L-homoserine. The term amino acid also includes salts thereof such as, for example, lysine monohydrochloride or lysine sulphate in the case of the amino acid L-lysine.

The invention further relates to mutants of coryneform bacteria which comprise an oxyR allele which codes for a polypeptide having OxyR transcription regulator activity which includes the amino acid sequence of SEQ ID NO: 2, with one of the stated proteinogenic amino acids except L-alanine being present at position 89. The exchange of L-alanine for L-valine is preferred.

The invention further relates to mutants of coryneform bacteria which comprise an oxyR allele which codes for a polypeptide having OxyR transcription regulator activity, which comprises one of the proteinogenic amino acids except L-alanine, but preferably L-valine, at the position corresponding to position 89 of the amino acid sequence of SEQ ID NO:2, where the gene includes a nucleotide sequence which is identical to the nucleotide sequence of a polynucleotide which is obtainable by a polymerase chain reaction (PCR) using a primer pair whose nucleotide sequences in each case include at least 15 consecutive nucleotides which are selected from the nucleotide sequence between position 1 and 750 of SEQ ID NO:3 or SEQ ID NO:7 and from the complementary nucleotide sequence between position 2484 and 1732 of SEQ ID NO:3 or SEQ ID NO:7. An example of a suitable primer pair is depicted in SEQ ID NO:9 and SEQ ID NO:10. Preferred starting material ("template" DNA) is chromosomal DNA of coryneform bacteria which have been treated in particular with a mutagen. The chromosomal DNA is particularly preferably of the genus *Corynebacterium* and very particularly preferably that of the species *Corynebacterium glutamicum*.

The invention further relates to mutants of coryneform bacteria which comprise an oxyR allele which codes for a polypeptide having OxyR transcription regulator activity, which includes an amino acid sequence with a length corresponding to 327 L-amino acids, with one of the proteinogenic amino acids except L-alanine, preferably L-valine, being present at position 89.

The invention further relates to mutants of coryneform bacteria which comprise an oxyR allele which codes for a polypeptide having OxyR transcription regulator activity, which comprises at position 70 to 108 of the amino acid sequence the amino acid sequence corresponding to position 70 to 108 of SEQ ID NO:6 or 8. The amino acid sequence of the encoded polypeptide preferably comprises an amino acid sequence corresponding to position 30 to 148 of SEQ ID NO:6 or 8 or position 2 to 188 of SEQ ID NO:6 or 8 or position 2 to 228 of SEQ ID NO:6 or 8 or position 2 to 268 of SEQ ID NO:6 or 8 or position 2 to 308 of SEQ ID NO:6 or 8 or position 2 to 324 of SEQ ID NO:6 or 8 or position 2 to 325 of SEQ ID NO:6 or 8 or position 2 to 326 of SEQ ID NO: 6 or 8, with L-valine being present at position 244 instead of L-alanine where appropriate. The length of the encoded polypeptide very particularly preferably includes 327 amino acids.

The invention further relates to mutants of coryneform bacteria which comprise an oxyR allele which codes for a polypeptide having OxyR transcription regulator activity, which comprises at position 89 or at the corresponding position of the amino acid sequence one of the proteinogenic amino acids except L-alanine, with preference for exchange for L-valine, and whose amino acid sequence is additionally at least 90%, preferably at least 92% or at least 94% or at least 96%, and very particularly preferably at least 97% or at least 98% or at least 99% identical to the amino acid sequence of SEQ ID NO:6 or SEQ ID NO:8, with L-valine being present at position 244 where appropriate.

The invention further relates to mutants of coryneform bacteria which comprise an oxyR allele which codes for a polypeptide having OxyR transcription regulator activity, which comprises at position 89 or at the corresponding position of the amino acid sequence one of the proteinogenic amino acids except L-alanine, with preference for exchange for L-valine, and whose nucleotide sequence is additionally at least 90%, preferably at least 92% or at least 94% or at least 96%, and very particularly preferably at least 97% or at least 98% or at least 99% identical to the nucleotide sequence of SEQ ID NO:5, with thymine being present at position 731 instead of cytosine where appropriate.

It is known that conservative amino acid exchanges alter the activity only insubstantially. Accordingly, the oxyR allele which is present in the mutants according to the invention and which codes for a polypeptide having OxyR transcription regulator activity may, in addition to the amino acid sequence shown in SEQ ID NO:6 or SEQ ID NO:8, comprise one (1) or more conservative amino acid exchange(s). The polypeptide preferably comprises not more than two (2), not more than three (3), not more than four (4) or not more than five (5) conservative amino acid exchanges. Where appropriate, L-valine is present at position 244 of SEQ ID NO:6 or 8 as shown in SEQ ID NO:21.

In the case of aromatic amino acids, mutual exchanges of phenylalanine, tryptophan and tyrosine are referred to as conservative exchanges. In the case of hydrophobic amino acids, mutual exchanges of leucine, isoleucine and valine are referred to as conservative exchanges. In the case of polar amino acids, mutual exchanges of glutamine and asparagine are referred to as conservative exchanges. In the case of basic amino acids, mutual exchanges of arginine, lysine and histidine are referred to as conservative exchanges. In the case of acidic amino acids, mutual exchanges of aspartic acid and glutamic acid are referred to as conservative exchanges. In the case of amino acids comprising hydroxyl groups, mutual exchanges of serine and threonine are referred to as conservative exchanges.

When working on the present invention, it was found by comparing the amino acid sequence using the Clustal program (Thompson et al., Nucleic Acids Research 22, 4637-4680 (1994)) that the amino acid sequences of the OxyR transcription regulators of different bacteria such as, for example, *Escherichia coli*, *Streptomyces coelicolor*, *Streptomyces avermitilis*, *Corynebacterium efficiens* and *Corynebacterium glutamicum* comprise a sequence motif consisting of the sequence Leu-Gly-Val-Met/Thr/Gln-Leu-Ile/Leu-Glu-Arg-Thr/Ser-Thr/Ser-Arg-Lys-Val-Ile/Leu, a sequence motif consisting of the sequence Ile-Pro-Thr-Val/Ala-Ala/Gly-Pro-Tyr-Ile/Leu-Leu-Pro and also a sequence motif consisting of the sequence Leu-Leu-Leu/Met-Leu-Glu/Asp-Glu/Asp-Gly-His-Cys-Leu-Arg/His-Asp-Gln. The designations "Met/Thr/Gln", "Ile/Leu", "Thr/Ser", "Val/Ala", "Ala/Gly", "Leu/Met", "Glu/Asp" and "Arg/His" mean that "Met or Thr or Gln", "Ile or Leu", "Thr or Ser", "Val or Ala", "Ala or Gly", "Leu or Met", "Glu or Asp" or "Arg or His" are present at the corresponding position.

Accordingly, preferred mutants of coryneform bacteria are those comprising an oxyR allele which codes for a polypeptide having OxyR transcription regulator activity, which includes at least one amino acid sequence selected from the group of Leu-Gly-Val-Met/Thr/Gln-Leu-Ile/Leu-Glu-Arg-Thr/Ser-Thr/Ser-Arg-Lys-Val-Ile/Leu, Ile-Pro-Thr-Val/Ala-Ala/Gly-Pro-Tyr-Ile/Leu-Leu-Pro and Leu-Leu-Leu/Met-Leu-Glu/Asp-Glu/Asp-Gly-His-Cys-Leu-Arg/His-Asp-Gln, and comprises at position 89 or at the corresponding or comparable position of the amino acid sequence one of the proteinogenic amino acids except L-alanine, preferably L-valine and, where appropriate, at position 244 L-valine.

The amino acid sequence motif Leu-Gly-Val-Met/Thr/Gln-Leu-Ile/Leu-Glu-Arg-Thr/Ser-Thr/Ser-Arg-Lys-Val-Ile/Leu is present for example in SEQ ID NO:2 and 4 or 6 and 8 from position 50 to 63. The amino acid sequence motif Ile-Pro-Thr-Val/Ala-Ala/Gly-Pro-Tyr-Ile/Leu-Leu-Pro is present for example in SEQ ID NO:2 and 4 or 6 and 8 from position 105 to 114. The amino acid sequence motif Leu-Leu-Leu/Met-Leu-Glu/Asp-Glu/Asp-Gly-His-Cys-Leu-Arg/His-Asp-Gln is present for example in SEQ ID NO: 2 and 4 or 6 and 8 from position 198 to 210.

The invention finally relates to mutants of coryneform bacteria which comprise an oxyR allele which codes for a polypeptide having OxyR transcription regulator activity, which includes the amino acid sequence of SEQ ID NO:6 or SEQ ID NO:8, with L-valine being present at position 244, where appropriate.

It is known that the host's own enzymes called aminopeptidases delete the terminal methionine during the protein synthesis.

The expression "a position corresponding to position 89 of the amino acid sequence" or "a position comparable to position 89 of the amino acid sequence" signifies the fact that through insertion or deletion of a codon coding for an amino acid in the N-terminal region (relative to position 89 of SEQ ID NO:6 or 8) of the encoded polypeptide the stated position and stated length is formally increased by one unit in the case of an insertion or is reduced by one unit in the case of a deletion. For example, deletion of the GAG codon coding for the amino acid L-glutamic acid at position 5 of SEQ ID NO:6 or 8 shifts the L-valine from position 89 to position 88. The stated length would then be: 326 amino acids. In the same way, insertion or deletion of a codon coding for an amino acid in the C-terminal region (relative to position 89) of the encoded polypeptide formally increases the stated length by one unit in the case of an insertion or reduces it by one unit in the case of a deletion. Such comparable positions can easily be identified by comparing the amino acid sequences in the form of an alignment for example with the aid of the Clustal programme or of the MAFFT programme.

The activity is substantially unaffected by such insertions and deletions. "Substantially unaffected" means that the activity of said variants differs by not more than 10%, not more than 7.5%, not more than 5%, not more than 2.5% or not more than 1% from the activity of the polypeptide having the amino acid sequence of SEQ ID NO:6 or 8, with L-valine being present at position 244 where appropriate.

The invention accordingly also relates to oxyR alleles which code for polypeptide variants of SEQ ID NO:6 or 8 which comprise one or more insertion(s) or deletion(s), with L-valine being present at position 244 where appropriate. The polypeptide preferably comprises not more than 5, not more than 4, not more than 3 or not more than 2 insertions or deletions of amino acids.

The sequence motifs mentioned above Leu-Gly-Val-Met/Thr/Gln-Leu-Ile/Leu-Glu-Arg-Thr/Ser-Thr/Ser-Arg-Lys-Val-Ile/Leu, Ile-Pro-Thr-Val/Ala-Ala/Gly-Pro-Tyr-Ile/Leu-Leu-Pro and Leu-Leu-Leu/Met-Leu-Glu/Asp-Glu/Asp-Gly-His-Cys-Leu-Arg/His-Asp-Gln are preferably not disrupted by such insertions/deletions.

The mutants according to the invention can be produced by using conventional in-vivo mutagenesis methods with cell populations of coryneform bacteria using mutagenic substances such as, for example, N-methyl-N'-nitro-N-nitrosoguanidine (MNNG), ethyl methanesulphonate (EMS), 5-bromouracil or ultraviolet light. Mutagenesis methods are described for example in the Manual of Methods for General Bacteriology (Gerhard et al. (Eds.), American Society for Microbiology, Washington, D.C., USA, 1981) or in Tosaka et al. (Agricultural and Biological Chemistry 42(4), 745-752 (1978)) or in Konicek et al. (Folia Microbiologica 33, 337-343 (1988)). Typical mutageneses using MNNG include concentrations of from 50 to 500 mg/l or even higher concentrations up to a maximum of 1 g/l, an incubation time of from 1 to 30 minutes at a pH of from 5.5 to 7.5. Under these conditions, the number of viable cells is reduced by a proportion of approximately 50% to 90% or approximately 50% to 99% or approximately 50% to 99.9% or more.

Mutants or cells are removed from the mutagenized cell population and are propagated. In a further step, their ability to secrete amino acids, preferably L-lysine, L-tryptophan, L-proline, L-valine, L-isoleucine or L-homoserine, in a batch culture using a suitable nutrient medium is preferably investigated. Suitable nutrient media and test conditions are described inter alia in U.S. Pat. No. 6,221,636, in U.S. Pat. No. 5,840,551, in U.S. Pat. No. 5,770,409, in U.S. Pat. No. 5,605,818, in U.S. Pat. No. 5,275,940 and in U.S. Pat. No. 4,224,409. In the case of uses of suitable robotic systems as described for example in Zimmermann et al. (VDI Berichte No. 1841, VDI-Verlag, Dusseldorf, Germany 2004, 439-443) or Zimmermann (Chemie Ingenenieur Technik 77 (4), 426-428 (2005)), numerous mutants can be investigated in a short time. In general, a maximum of 3000, a maximum of 10 000, a maximum of 30 000 or also a maximum of 60 000 mutants, where appropriate also more, are investigated. Mutants which, compared with the parent strain or unmutagenized starting strain, secrete increased amino acids into the nutrient medium or into the interior of the cell are identified in this way. These include for example mutants whose amino acid secretion is increased by at least 0.5%.

DNA is then prepared or isolated from the mutants, and the corresponding polynucleotide is synthesized with the aid of the polymerase chain reaction using primer pairs which permit amplification of the oxyR gene or of the oxyR allele according to the invention or of the mutation according to the invention at position 89. The DNA is preferably isolated from mutants which secrete amino acids to an increased extent.

It is possible to select for this purpose any primer pairs from the nucleotide sequence located upstream and downstream of the mutation according to the invention, and the nucleotide sequence complementary thereto. One primer of a primer pair in this case preferably includes at least 15, at least 18, at least 20, at least 21 or at least 24 consecutive nucleotides selected from the nucleotide sequence between position 1 and 1014 of SEQ ID NO:3 or SEQ ID NO:7. The second primer belonging to a primer pair includes at least 15, at least 18, at least 20, at least 21 or at least 24 consecutive nucleotides selected from the complementary nucleotide sequence from position 2484 and 1018 of SEQ ID NO:3 or SEQ ID NO:7.

If amplification of the coding region is desired, the primer pair is preferably selected from the nucleotide sequence between position 1 and 750 of SEQ ID NO:3 or SEQ ID NO:7 and from the complementary nucleotide sequence between position 2484 and 1732 of SEQ ID NO:3 or SEQ ID NO:7. A suitable primer pair is for example the primer pair oxyR_XL_A1 and oxyR_XL_E1 represented by SEQ ID NO:9 and SEQ ID NO:10.

If amplification of part of the coding region, as depicted for example in SEQ ID NO:17 and 19, is desired, the primer pair is preferably selected from the nucleotide sequence between position 751 and 1014 or between position 1 and 1014 of SEQ ID NO:3 or SEQ ID NO:7 and from the complementary nucleotide sequence between position 1731 and 1018 or 2484 and 1018 of SEQ ID NO:3 or SEQ ID NO:7. The primer can moreover be equipped with recognition sites for restriction enzymes, with a biotin group or further accessories, as described in the prior art. The total length of the primer generally does not exceed 30, 40, 50 or 60 nucleotides.

Polynucleotides are prepared by amplification of selected sequences, such as the oxyR allele according to the invention, from provided, for example chromosomal, DNA ("template DNA") by PCR amplification generally employing thermostable DNA polymerases. Examples of such DNA polymerases are the Taq polymerase from *Thermus aquaticus*, which is marketed inter alia by Qiagen (Hilden, Germany), the Vent polymerase from *Thermococcus litoralis*, which is marketed inter alia by New England Biolabs (Frankfurt, Germany) or the Pfu polymerase from *Pyrococcus furiosus*, which is marketed inter alia by Stratagene (La Jolla, USA). Polymerases having proof-reading activity are preferred. Proof-reading activity means that these polymerases are able to recognize incorrectly incorporated nucleotides and to eliminate the error by renewed polymerization (Lottspeich and Zorbas, Bioanalytik, Spektrum Akademischer Verlag, Heidelberg, Germany (1998)). Examples of polymerases having proof-reading activity are the Vent polymerase and the Pfu polymerase.

The conditions in the reaction mixture are set according to the manufacturer's information. The polymerases are generally supplied by the manufacturer together with the usual buffer which normally has concentrations of 10-100 mM Tris/HCl and 6-55 mM KCl at pH 7.5-9.3. Magnesium chloride is added in a concentration of 0.5-10 mM unless it is present in the buffer supplied by the manufacturer. In addition, deoxynucleoside triphosphates are added in a concentration of 0.1-16.6 mM to the reaction mixture. The primers are introduced into the reaction mixture in a final concentration of 0.1-3 μM, and the template DNA in the optimal case with $10^2$ to $10^5$ copies. It is also possible to employ $10^6$ to $10^7$ copies. The appropriate polymerase is added to the reaction mixture in an amount of 2-5 units. A typical reaction mixture has a volume of 20-100 μl.

Further additions which can be included in the reaction are bovine serum albumin, Tween 20, gelatin, glycerol, formamide or DMSO (Dieffenbach and Dveksler, PCR Primer—A Laboratory Manual, Cold Spring Harbor Laboratory Press, USA 1995).

A typical PCR run consists of three different, consecutively repeating temperature steps. At the outset, the reaction is started by raising the temperature to 92° C.-98° C. for 4 to 10 minutes in order to denature the introduced DNA. This is followed by repetitions firstly of a step for denaturation of the introduced DNA at approximately 92-98° C. for 10-60 seconds, then a step to bind the primers to the introduced DNA at a particular temperature which depends on the primers ("annealing temperature") and which, from experience, is 50° C. to 60° C. and can be calculated individually for each primer pair, for 10-60 seconds. Detailed information concerning this is to be found by the skilled person in Rychlik et al. (Nucleic Acids Research 18 (21): 6409-6412). This is subsequently followed by a synthesis step to extend the introduced primers ("extension") at the activity optimum indicated in each case for the polymerase, normally in the range from 73° C. to 67° C., preferably 72° C. to 68° C., depending on the polymerase. The duration of this extension step depends on the efficiency of the polymerase and length of the PCR product to be amplified. In a typical PCR, this step takes 0.5-8 minutes, preferably 2-4 minutes. These three steps are repeated 30 to 35 times, where appropriate up to 50 times. A final "extension" step of 4-10 minutes terminates the reaction. The polynucleotides prepared in this way are also referred to as amplicons; the term nucleic acid fragment is likewise in use.

Further instructions and information on PCR are to be found by the skilled person for example in the handbook "PCR-Strategies" (Innis, Felfand and Sninsky, Academic Press, Inc., 1995), in the handbook by Diefenbach and Dveksler "PCR Primer—a laboratory manual" (Cold Spring Harbor Laboratory Press, 1995), in the handbook by Gait "Oligonucleotide synthesis: A Practical Approach" (IRL Press, Oxford, UK, 1984) and in Newton and Graham "PCR" (Spektrum Akademischer Verlag, Heidelberg, Germany, 1994).

The nucleotide sequence is subsequently determined for example by the chain termination method of Sanger et al. (Proceedings of the National Academies of Sciences, U.S.A., 74, 5463-5467 (1977)) with the modifications indicated by Zimmermann et al. (Nucleic Acids Research 18, 1067 pp (1990)), and the polypeptide encoded by this nucleotide sequence is analysed in particular in relation to the amino acid sequence. For this purpose, the nucleotide sequence is entered into a program for translating DNA sequence into an amino acid sequence. Suitable programs are for example the "Patentin" program which is obtainable from patent offices, for example the US Patent Office (USPTO), or the "Translate Tool" which is available on the ExPASy Proteomics Server in the World Wide Web (Gasteiger et al., Nucleic Acids Research 31, 3784-3788 (2003)).

Mutants whose oxyR alleles code for polypeptides having OxyR transcription regulator enzymic activity, which comprise at position 89 of the amino acid sequence, or the corre sponding or comparable position, one of the proteinogenic amino acids except L-alanine, are identified in this way. Exchange for L-valine is preferred.

The complete chromosome of the mutant is determined where appropriate. It is possible in this connection to employ the method described by Margulies et al. (Nature, 437(7057): 376-380 (2005)) and Velicer et al. (Proceedings of the National Academy of Sciences, U.S.A., 103(21), 8107-8112 (2006)) which is known to those skilled in the art by the phrase "pyro-sequencing" and enables complete genomes to be sequenced rapidly.

The invention accordingly relates to a mutant of a coryneform bacterium, characterized in that it is obtainable by the following steps:
a) treatment of a coryneform bacterium which has the ability to secrete amino acids with a mutagenic agent,
b) isolation and propagation of the mutant generated in a),
c) preferably determination of the ability of the mutant to secrete in a medium, or enrich in the interior of the cell, at least 0.5% more amino acid than the coryneform bacterium employed in a) (starting strain),
d) preparation of nucleic acid from the mutant obtained in b),
e) preparation of a nucleic acid molecule (or amplicon or nucleic acid fragment) using the polymerase chain reaction, of the nucleic acid from d), and of a primer pair consisting of a first primer including at least 15 consecutive nucleotides selected from the nucleotide sequence between position 1 and 1014, preferably 1 to 750 of SEQ ID NO:3 or SEQ ID NO:7 and a second primer including at least 15 consecutive nucleotides selected from the complementary nucleotide sequence between position 2484 and 1018, preferably 2484 and 1732 of SEQ ID NO:3 or 7,
f) determination of the nucleotide sequence of the nucleic acid molecule obtained in e), and determination of the encoded amino acid sequence,
g) where appropriate comparison of the amino acid sequence determined in f) with SEQ ID NO:6 or 8, with L-valine being present at position 244 where appropriate, and
h) identification of a mutant which comprises a polynucleotide which codes for a polypeptide which comprises at position 89 or at comparable position one of the proteinogenic amino acids except L-alanine, preferably L-valine and, where appropriate, L-valine at position 244.

The mutants generated in this way typically comprise one (1) copy of the described oxyR allele.

SEQ ID NO:5 represents by way of example the coding region of the oxyR allele of a mutant according to the invention. The coding region of the wild-type gene is represented as SEQ ID NO:1. SEQ ID NO:1 comprises at position 265 the nucleobase guanine, at position 266 the nucleobase cytosine and at position 267 the nucleobase cytosine. SEQ ID NO:1 thus comprises from position 265 to 267 the GCC codon coding for the amino acid L-alanine. SEQ ID NO:5 comprises at position 266 the nucleobase thymine. This cytosine-to-thymine transition results at position 265 to 267 in the GTC codon coding for the amino acid L-valine.

In addition, the nucleotide sequences depicted in SEQ ID NO: 5 and 7 or SEQ ID NO: 21 may comprise further base exchanges which have resulted from the mutagenesis treatment but are not expressed by an altered amino acid sequence. Mutations of this type are also referred to by those skilled in the art as silent or neutral mutations. These silent mutations may likewise already be present in the coryneform bacterium employed for the metagenesis treatment.

The coryneform bacteria used for the mutagenesis preferably already have the ability to secrete the desired amino acid into the nutrient medium or fermentation broth surrounding them, or enrich it in the interior of the cells.

L-Lysine-producing coryneform bacteria typically have a feedback-resistant or desensitized aspartate kinase. Feedback-resistant aspartate kinases mean aspartate kinases (LysC) which by comparison with the wild form exhibit less sensitivity to inhibition by mixtures of lysine and threonine or mixtures of AEC (aminoethylcysteine) and threonine or lysine alone or AEC alone. The genes or alleles coding for these desensitized aspartate kinases are also referred to as $lysC^{FBR}$ alleles. Numerous $lysC^{FBR}$ alleles are described in the state of the art and code for aspartate kinase variants which have amino acid exchanges by comparison with the wild-type protein. The coding region of the wild-type lysC gene of *Corynebacterium glutamicum* corresponding to the access number AX756575 of the NCBI database is depicted in SEQ ID NO:11, and the polypeptide encoded by this gene is depicted in SEQ ID NO:12.

The L-lysine-producing coryneform bacteria employed for the measures of the invention preferably have a lysC allele which codes for an aspartate kinase variant which has the amino acid sequence of SEQ ID NO:12, the latter including one or more of the amino acid exchanges selected from the group:
LysC A279T (L-alanine at position 279 of the encoded aspartate kinase protein according to SEQ ID NO: 12 exchanged for L-threonine; see U.S. Pat. No. 5,688,671 and access numbers E06825, E06826, E08178 and 174588 to 174597),
LysC A279V (L-alanine at position 279 of the encoded aspartate kinase protein according to SEQ ID NO: 12 exchanged for L-valine, see JP 6-261766 and access number E08179),
LysC L297Q (L-leucine at position 297 of the encoded aspartate kinase protein according to SEQ ID NO: 12 exchanged for L-glutamine; see DE 102006026328,
LysC S301F (L-serine at position 301 of the encoded aspartate kinase protein according to SEQ ID NO: 12 exchanged for L-phenylalanine; see U.S. Pat. No. 6,844,176 and access number E08180),
LysC S301Y (L-serine at position 301 of the encoded aspartate kinase protein according to SEQ ID NO: 12 exchanged for L-tyrosine, see Kalinowski et al. (Molecular and General Genetics 224, 317-324 (1990)) and access number X57226),
LysC T308I (L-threonine at position 308 of the encoded aspartate kinase protein according to SEQ ID NO: 12 exchanged for L-isoleucine; see JP 6-261766 and access number E08181)
LysC T311I (L-threonine at position 311 of the encoded aspartate kinase protein according to SEQ ID NO: 12 exchanged for L-isoleucine; see WO 00/63388 and U.S. Pat. No. 6,893,848),
LysC S317A (L-serine at position 317 of the encoded aspartate kinase protein according to SEQ ID NO: 12 exchanged for L-alanine; see U.S. Pat. No. 5,688,671 and access number 174589),
LysC R320G (L-arginine at position 320 of the encoded aspartate kinase protein according to SEQ ID NO: 12 exchanged for glycine; see Jetten et al. (Applied Microbiology and Biotechnology 43, 76-82 (995)) and access number L27125),
LysC G345D (glycine at position 345 of the encoded aspartate kinase protein according to SEQ ID NO: 12 exchanged for L-aspartic acid; see Jetten et al. (Applied Microbiology and Biotechnology 43, 76-82 (995)) and access number L16848),
LysC T380I (L-threonine at position 380 of the encoded aspartate kinase protein according to SEQ ID NO: 12 exchanged for L-isoleucine; see WO 01/49854 and access number AX192358), and

LysC S381F (L-serine at position 3811 of the encoded aspartate kinase protein according to SEQ ID NO: 12 exchanged for L-phenylalanine; see EP 0435132).

Particular preference is given to the lysC$^{FBR}$ allele lysC T311I (threonine at position 311 of the encoded aspartate kinase protein according to SEQ ID NO: 12 exchanged for isoleucine) and a lysC$^{FBR}$ allele comprising at least one exchange selected from the group of a A279T (alanine at position 279 of the encoded aspartate kinase protein according to SEQ ID NO: 12 exchanged for threonine), S381F (serine at position 381 of the encoded aspartate kinase protein according to SEQ ID NO: 12 exchanged for phenylalanine) and S317A (serine at position 317 of the encoded aspartate kinase protein according to SEQ ID NO: 12 exchanged for alanine).

The lysC$^{FBR}$ allele lysC T311I (threonine at position 311 of the encoded aspartate kinase protein according to SEQ ID NO: 12 exchanged for isoleucine) is very particularly preferred.

The strain DSM 16833 (WO 06/063660) has a lysC$^{FBR}$ allele which codes for an aspartate kinase protein which comprises the amino acid exchange T311I.

The strain NRRL B-11474 (U.S. Pat. No. 4,275,157) has a lysC$^{FBR}$ allele which codes for an aspartate kinase protein which comprises the amino acid exchanges A279T and S381F.

In the manner described above, starting from the strain ATCC 16833, a mutant designated DM1914 which comprises an oxyR allele which codes for a polypeptide in which L-valine is present at position 89 of the amino acid sequence was isolated. The nucleotide sequence of the coding region of the oxyR allele of the mutant DM1914 is depicted as SEQ ID NO:5 and the amino acid sequence of the encoded polypeptide is depicted as SEQ ID NO:6 or 8.

Also in the manner described above, a mutant which comprises L-valine instead of L-alanine at position 89 of SEQ ID NO:2 and additionally comprises L-valine instead of L-alanine at position 244 of SEQ ID NO:2 was isolated. The nucleotide sequence of the oxyR allele of this mutant is depicted as SEQ ID NO:21 and the amino acid sequence of the encoded polypeptide is depicted as SEQ ID NO:22.

It is additionally possible to use L-lysine-secreting coryneform bacteria which have properties known in the state of the art.

L-Tryptophan-producing coryneform bacteria typically have a feedback-resistant or desensitized anthranilate synthase. Feedback-resistant anthranilate synthase (TrpE) means anthranilate synthases which, by comparison with the wild form, have a sensitivity to inhibition by tryptophan or 5-fluorotryptophan (Matsui et al., Journal of Bacteriology 169 (11): 5330-5332 (1987)) or similar analogues which is less by at least 5 to 10%, or at least 10% to 15% or at least 10% to 20%. The genes or alleles coding for these desensitized anthranilate synthases are also referred to as trpE$^{FBR}$ alleles. Examples of such mutants and alleles are for example described in U.S. Pat. No. 6,180,373 and EP0338474.

L-Proline-producing coryneform bacteria possess inter alia a γ-glutamyl kinase (ProB) which has at amino acid position 149 or comparable position a proteinogenic amino acid other than glycine, preferably L-aspartic acid (WO06066758).

L-Valine-producing coryneform bacteria typically have a feedback-resistant or desensitized acetolactate synthase (acetohydroxyacid synthase; EC No. 2.2.1.6).

Feedback-resistant acetolactate synthase means an acetolactate synthase which, by comparison with the wild form, shows a lower sensitivity to inhibition by one or more of the amino acids selected from the group of L-valine, L-isoleucine and L-leucine, preferably L-valine.

The acetolactate synthase (IlvB, IlvN) of Corynebacterium consists of a so-called large subunit encoded by the ilvB gene and of a so-called small subunit encoded by the ilvN gene (Keilhauer et al., Journal of Bacteriology 175(17), 5595-5603 (1993)). WO 05/003357 and Elisakova et al. (Applied and Environmental Microbiology 71(1):207-13 (2005)) report on variants of the IlvN subunit which confer resistance to L-valine, L-isoleucine and L-leucine on the acetolactate synthase. One variant comprises at position 21 of the amino acid sequence L-aspartic acid instead of L-isoleucine (IlvN I21D) and at position 22 L-phenylalanine instead of L-isoleucine (IlvN I22F). The second variant comprises at position 20 of the amino acid sequence L-aspartic acid instead of glycine (IlvN G20D), at position 21 of the amino acid sequence L-aspartic acid instead of L-isoleucine (IlvN I21D) and at position 22 L-phenylalanine instead of L-isoleucine (IlvN I22F).

L-Isoleucine-producing coryneform bacteria typically have a feedback-resistant or desensitized threonine dehydratase (=threonine deaminase).

Feedback-resistant threonine dehydratase means a threonine dehydratase (EC No. 4.3.1.19) which, by comparison with the wild form, shows a lower sensitivity to inhibition by L-isoleucine. The genes or alleles coding for this desensitized threonine dehydratase are also referred to as ilvA$^{FBR}$ alleles.

The coding region of the wild-type ilvA gene of Corynebacterium glutamicum corresponding to access numbers L01508 and NC_006958 of the NCBI database is depicted in SEQ ID NO:13 and the polypeptide encoded by this gene is depicted in SEQ ID NO:14.

The threonine dehydratase variants described in U.S. Pat. No. 6,107,063 and in Morbach et al. (Applied and Environmental Microbiology 61 (12), 4315-4320 (1995)) comprise one or more of the amino acid exchanges selected from the group:

IlvA M199V (L-methionine at position 199 of the encoded threonine dehydratase protein according to SEQ ID NO: 14 exchanged for L-valine; see U.S. Pat. No. 6,107,063), IlvA A257G (L-alanine at position 257 of the encoded threonine dehydratase protein according to SEQ ID NO: 14 exchanged for L-arginine; see U.S. Pat. No. 6,107,063), IlvA H278R (L-histidine at position 278 of the encoded threonine dehydratase protein according to SEQ ID NO: 14 exchanged for L-arginine; see U.S. Pat. No. 6,107,063), IlvA V323A (L-valine at position 323 of the encoded threonine dehydratase protein according to SEQ ID NO: 14 exchanged for L-alanine; see Morbach et al.), IlvA L351S (L-leucine at position 351 of the encoded threonine dehydratase protein according to SEQ ID NO: 14 exchanged for L-serine; see U.S. Pat. No. 6,107,063)

IlvA D378G (L-aspartic acid at position 378 of the encoded threonine dehydratase protein according to SEQ ID NO: 14 exchanged for glycine; see Morbach et al.)

The resulting mutants show, by comparison with the starting strain or parent strain employed, increased excretion or production of the desired amino acid in a fermentation process.

The invention likewise relates to an isolated polynucleotide which codes for a polypeptide having OxyR transcription regulator activity, which comprises at position 89 or at a corresponding or comparable position of the amino acid sequence one of the proteinogenic amino acids except L-alanine, with exchange for L-valine being preferred.

The polynucleotide according to the invention can be isolated from a mutant according to the invention.

It is additionally possible to employ in vitro methods for the mutagenesis of the oxyR gene. On use of in vitro methods, isolated polynucleotides which comprise an oxyR gene of a coryneform bacterium, preferably the wild-type gene of *Corynebacterium glutamicum* described in the prior art, are subjected to a mutagenic treatment.

The isolated polynucleotides may be for example isolated total DNA or chromosomal DNA or else amplicons of the oxyR gene which have been prepared with the aid of the polymerase chain reaction (PCR). Amplicons of this type are also referred to as PCR products. Instructions for amplifying DNA sequences with the aid of the polymerase chain reaction are to be found by the skilled person inter alia in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994). It is likewise possible for the oxyR gene which is to be mutagenized firstly to be incorporated into a vector, for example into a bacteriophage or into a plasmid.

Suitable methods for in vitro mutagenesis are inter alia treatment with hydroxylamine according to Miller (Miller, J. H.: A Short Course in Bacterial Genetics. A Laboratory Manual and Handbook for *Escherichia coli* and OxyRated Bacteria, Cold Spring Harbor Laboratory Press, Cold Spring Harbor, 1992), the use of mutagenic oligonucleotides (T. A. Brown: Gentechnologie für Einsteiger, Spektrum Akademischer Verlag, Heidelberg, 1993 and R. M. Horton: PCR-Mediated Recombination and Mutagenesis, Molecular Biotechnology 3, 93-99 (1995)) and the use of a polymerase chain reaction utilizing a DNA polymerase which shows a high error rate. A DNA polymerase of this type is for example the Mutazyme DNA polymerase (GeneMorph PCR Mutagenesis Kit, No. 600550) from Stratagene (LaJolla, Calif., USA).

Further instructions and reviews on the generation of mutations in vivo or in vitro can be found in the prior art and known textbooks of genetics and molecular biology such as, for example, the textbook of Knippers ("Molekulare Genetik", 6th edition, Georg Thieme Verlag, Stuttgart, Germany, 1995), that of Winnacker ("Gene and Klone", VCH Verlagsgesellschaft, Weinheim, Germany, 1990) or that of Hagemann ("Allgemeine Genetik", Gustav Fischer Verlag, Stuttgart, 1986).

The invention further relates to an isolated polynucleotide which codes for a polypeptide having OxyR transcription regulator activity, which includes the amino acid sequence of SEQ ID NO:2, with one of the proteinogenic amino acids except L-alanine being present at position 89 of the amino acid sequence. Exchange for L-valine is preferred. Where appropriate, L-valine is present at position 244.

The invention further relates to an isolated polynucleotide that codes for a polypeptide having OxyR transcription regulator activity, which includes an amino acid sequence with a length of 327 amino acids, and where one of the proteinogenic L-amino acids except L-alanine, preferably L-valine, is present at position 89.

The invention further relates to an isolated polynucleotide which codes for a polypeptide having OxyR transcription regulator enzymic activity, which comprises at position 70 to 108 of the amino acid sequence the amino acid sequence corresponding to position 70 to 108 of SEQ ID NO:6 or 8. The amino acid sequence of the encoded polypeptide preferably comprises an amino acid sequence corresponding to position 30 to 148 of SEQ ID NO:6 or 8 or position 2 to 188 of SEQ ID NO:6 or 8 or position 2 to 228 of SEQ ID NO:6 or 8 or position 2 to 268 of SEQ ID NO:6 or 8 or position 2 to 308 of SEQ ID NO:6 or 8 or position 2 to 324 of SEQ ID NO:6 or 8 or position 2 to 325 of SEQ ID NO:6 or 8 or position 2 to 326 of SEQ ID NO:6 or 8, with L-valine being present at position 244 instead of L-alanine where appropriate. The length of the encoded polypeptide very particularly preferably includes 327 amino acids.

The invention further relates to an isolated polynucleotide that codes for a polypeptide having OxyR transcription regulator activity, which comprises at position 89 of the amino acid sequence or a corresponding or comparable position one of the proteinogenic amino acids except L-alanine, preferably L-valine, and which includes a nucleotide sequence which is identical to the nucleotide sequence of a polynucleotide which is obtainable by polymerase chain reaction (PCR) using the primer pair whose nucleotide sequences in each case include at least 15 consecutive nucleotides which are selected from the nucleotide sequence between position 1 and 1014, preferably between position 1 and 750, of SEQ ID NO:3 or SEQ ID NO:7 and from the complementary nucleotide sequence between position 2484 and 1018, preferably between position 2484 and 1732, of SEQ ID NO:3 or SEQ ID NO:7. One example of such a primer pair is depicted in SEQ ID NO:9 and SEQ ID NO:10. Preferred starting material ("template" DNA) is chromosomal DNA of coryneform bacteria which have been treated in particular with a mutagen. The chromosomal DNA is particularly preferably of the genus *Corynebacterium* and very particularly preferably that of the species *Corynebacterium glutamicum*.

The invention further relates to an isolated polynucleotide which hybridizes with the nucleotide sequence complementary to SEQ ID NO:5 under stringent conditions and codes for a polypeptide having OxyR transcription regulator activity, which comprises at position 89 of the amino acid sequence or a corresponding or comparable position one of the proteinogenic amino acids except L-alanine, preferably L-valine and, where appropriate, L-valine at position 244.

Instructions for hybridizing nucleic acids or polynucleotides are to be found by the skilled person inter alia in the handbook "The DIG System Users Guide for Filter Hybridization" from Boehringer Mannheim GmbH (Mannheim, Germany, 1993) and in Liebl et al. (International Journal of Systematic Bacteriology 41: 255-260 (1991)). The hybridization takes place under stringent conditions, meaning that the only hybrids formed are those in which the probe, i.e. a polynucleotide including the nucleotide sequence complementary to SEQ ID NO:5, and the target sequence, i.e. the polynucleotides treated or identified with the probe, are at least 90% identical. It is known that the stringency of hybridization including the washing steps is influenced or determined by varying the buffer composition, the temperature and the salt concentration. The hybridization reaction is generally carried out at relatively low stringency compared with the washing steps (Hybaid Hybridisation Guide, Hybaid Limited, Teddington, UK, 1996).

It is possible to employ for the hybridization reaction for example a buffer corresponding to 5×SSC buffer at a temperature of approx. 50° C.-68° C. In this case, probes may also hybridize with polynucleotides which show less than 90% identity to the nucleotide sequence of the probe employed. Such hybrids are less stable and are removed by washing under stringent conditions. This can be achieved for example by reducing the salt concentration to 2×SSC and, where appropriate, subsequently 0.5×SSC (The DIG System User's Guide for Filter Hybridisation, Boehringer Mannheim, Mannheim, Germany, 1995), setting a temperature of approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. Temperature ranges of approx. 64° C.-68° C. or approx. 66° C.-68° C. are preferred. It is possible where appropriate to reduce the salt concentration to a concentration corresponding to 0.2×SSC or 0.1×SSC. The SSC buffer comprises where appropriate sodium dodecyl sulphate (SDS) in a concentration of 0.1%. It is possible by increasing the hybridization temperature stepwise in steps of approx. 1-2° C. from 50° C. to 68° C. to isolate polynucleotide fragments which have at least 90% or at least 91%, preferably at least 92% or at least 93% or at least 94% or at least 95 or at least 96% and very particularly preferably at least 97% or at least 98% or at least 99% identity to the sequence or complementary sequence of the probe employed, and code for a polypeptide having OxyR transcription regulator activity, which comprises the amino acid exchange according to the invention. The nucleotide sequence of the polynucleotide obtained in this way is determined by known methods. Further instructions for hybridization are obtainable in the form of so-called kits on the market (e.g. DIG Easy Hyb from Roche Diagnostics GmbH, Mannheim, Germany, catalogue No. 1603558). The nucleotide sequences obtained in this way code for polypeptides having OxyR transcription regulator activity, which are at least 90%, preferably at least 92% or at least 94% or at least 96%, and very particularly preferably at least 97% or at least 98% or at least 99% identical to the amino acid sequence of SEQ ID NO:6 or SEQ ID NO:8 and comprise the amino acid exchange according to the invention and with L-valine being present at position 244 where appropriate.

The invention further relates to an isolated polynucleotide which codes for a polypeptide having OxyR transcription regulator activity, which comprises at position 89 or a corresponding or comparable position of the amino acid sequence one of the proteinogenic amino acids except L-alanine, with preference for exchange for L-valine, and which includes an amino acid sequence which is additionally at least 90%, preferably at least 92% or at least 94% or at least 96%, and very particularly preferably at least 97% or at least 98% or at least 99% identical to the amino acid sequence of SEQ ID NO:6 or SEQ ID NO:8, with L-valine being present at position 244 where appropriate.

The invention further relates to an isolated polynucleotide which codes for a polypeptide having OxyR transcription regulator activity, which comprises at position 89 or a corresponding or comparable position of the amino acid sequence one of the proteinogenic amino acids except L-alanine, with preference for exchange for L-valine and which includes a nucleotide sequence which is additionally at least 90%, preferably at least 92% or at least 94% or at least 96%, and very particularly preferably at least 97% or at least 98% or at least 99% identical to the nucleotide sequence of SEQ ID NO:5, with thymine being present at position 731 where appropriate.

In addition, preferred isolated polynucleotides code for a polypeptide having OxyR transcription regulator activity, which comprises at position 89 of the amino acid sequence or a corresponding or comparable position one of the proteinogenic amino acids except L-alanine, preferably L-valine, and which comprise at least one sequence motif or an amino acid sequence selected from the group of Leu-Gly-Val-Met/Thr/Gln-Leu-Ile/Leu-Glu-Arg-Thr/Ser-Thr/Ser-Arg-Lys-Val-Ile/Leu, Ile-Pro-Thr-Val/Ala-Ala/Gly-Pro-Tyr-Ile/Leu-Leu-Pro and Leu-Leu-Leu/Met-Leu-Glu/Asp-Glu/Asp-Gly-His-Cys-Leu-Arg/His-Asp-Gln.

The designations "Met/Thr/Gln", "Ile/Leu", "Thr/Ser", "Val/Ala", "Ala/Gly", "Leu/Met", "Glu/Asp" and "Arg/His" mean that "Met or Thr or Gln", "Ile or Leu", "Thr or Ser", "Val or Ala", "Ala or Gly", "Leu or Met", "Glu or Asp" or "Arg or His" are present at the corresponding position.

The invention further relates to an isolated polynucleotide that codes for a polypeptide having OxyR transcription regulator enzymic activity, which includes the amino acid sequence of SEQ ID NO:6 or 8, with L-valine being present at position 244 where appropriate. The encoded polypeptide comprises where appropriate one (1) or more conservative amino acid exchange(s). The polypeptide preferably comprises not more than two (2), not more than three (3), not more than four (4) or not more than five (5) conservative amino acid exchanges.

The invention further relates to an isolated polynucleotide that codes for a polypeptide having OxyR transcription regulator activity, which includes the amino acid sequence of SEQ ID NO:6 or 8 including an extension at the N or C terminus by at least one (1) amino acid. This extension comprises not more than 50, 40, 30, 20, 10, 5, 3 or 2 amino acids or amino acid residues. L-valine is present, where appropriate, at position 244 of SEQ ID NO:6 or 8.

The invention finally relates also to oxyR alleles which code for polypeptide variants of SEQ ID NO:6 or 8, with L-glutamic acid being present, where appropriate, at position 244, which comprise one or more insertions or deletions. These preferably comprise a maximum of 5, a maximum of 4, a maximum of 3 or a maximum of 2 insertions or deletions of amino acids. The sequence motifs Leu-Gly-Val-Met/Thr/Gln-Leu-Ile/Leu-Glu-Arg-Thr/Ser-Thr/Ser-Arg-Lys-Val-Ile/Leu, Ile-Pro-Thr-Val/Ala-Ala/Gly-Pro-Tyr-Ile/Leu-Leu-Pro and Leu-Leu-Leu/Met-Leu-Glu/Asp-Glu/Asp-Gly-His-Cys-Leu-Arg/His-Asp-Gln is/are preferably not disrupted by such insertions/deletions.

The invention further relates to an isolated polynucleotide which includes the nucleotide sequence shown in SEQ ID NO:5 or SEQ ID NO:7 or SEQ ID NO:21.

The invention finally relates to an isolated polynucleotide comprising the oxyR allele of the mutant DM1914.

The invention additionally relates to an isolated polynucleotide which includes part of the coding region of an oxyR allele according to the invention, where the isolated polynucleotide includes in every case the part of the coding region which comprises the amino acid exchange at position 89 of the amino acid sequence of the encoded polypeptide.

Included in particular is a nucleic acid molecule or DNA fragment which codes for at least one amino acid sequence corresponding to position 70 to 108 of SEQ ID NO:2, or which codes for at least one amino acid sequence corresponding to position 30 to 148 of SEQ ID NO:2, or which codes for at least one amino acid sequence corresponding to position 2 to 188 of SEQ ID NO:2, or which codes for at least one amino acid sequence corresponding to position 2 to 228 of SEQ ID NO:2, or which codes for at least one amino acid sequence corresponding to position 2 to 268 of SEQ ID NO:2, or which codes for at least one amino acid sequence corresponding to position 2 to 308 of SEQ ID NO:2, or which codes for at least one amino acid sequence corresponding to position 2 to 324 of SEQ ID NO:2, or which codes for at least one amino acid sequence corresponding to position 2 to 325 of SEQ ID NO:2, or which codes for at least one amino acid sequence corresponding to position 2 to 326, where one of the proteinogenic amine acids except L-alanine, preferably L-valine, is present at the position corresponding to 89 of SEQ ID NO:2, and with L-valine being present at position 244 where appropriate.

One example of a reading frame according to the invention including a polynucleotide which codes for at least the amino acid sequence from position 70 to 108 corresponding to SEQ ID NO:2, where one of the proteinogenic amino acids (Xaa) except L-alanine is present at the position corresponding to 89 of the amino acid sequence, is detailed below:

```
aag ttg ctg cca ttc gcc aaa tcc acc ctt gac gcg gcg gag tct ttc ctc

Lys Leu Leu Pro Phe Ala Lys Ser Thr Leu Asp Ala Ala Glu Ser Phe Leu
70              75                  80              85 tcc cac nnn aag ggc gcc aac ggt tcg ctc act gga ccg ttg acc gta ggc

Ser His Xaa Lys Gly Ala Asn Gly Ser Leu Thr Gly Pro Leu Thr Val Gly
            90              95                  100 atc atc ccc acg gcg

Ile Ile Pro Thr Ala
    105         108
```

It is likewise depicted as SEQ ID NO:17. The amino acid sequence encoded by this reading frame is depicted as SEQ ID NO:18. Position 20 in SEQ ID NO:18 corresponds to position 89 of SEQ ID NO:2, 4, 6 or 8.

Preferred nucleic acid molecules code for at least one amino acid sequence corresponding to position 70 to 108 of SEQ ID NO:6 or 8, or at least corresponding to position 30 to 148 of SEQ ID NO: 6 or 8, or at least corresponding to position 2 to 188 of SEQ ID NO: 6 or 8, or at least corresponding to position 2 to 228 of SEQ ID NO: 6 or 8, or at least corresponding to position 2 to 268 of SEQ ID NO: 6 or 8, or at least corresponding to position 2 to 308 of SEQ ID NO: 6 or 8, or at least corresponding to position 2 to 324 of SEQ ID NO: 6 or 8, or at least corresponding to position 2 to 325 of SEQ ID NO: 6 or 8, or at least corresponding to position 2 to 326 of SEQ ID NO:6 or 8, with L-valine being present at position 244 where appropriate.

One example of a reading frame according to the invention including a polynucleotide which codes for at least the amino acid sequence corresponding to position 70 to 108 of SEQ ID NO:6 or 8, is detailed below:

```
aag ttg ctg cca ttc gcc aaa tcc acc ctt gac gcg gcg gag tct ttc ctc

Lys Leu Leu Pro Phe Ala Lys Ser Thr Leu Asp Ala Ala Glu Ser Phe Leu
70              75                  80              85 tcc cac gtc aag ggc gcc aac ggt tcg ctc act gga ccg ttg acc gta ggc

Ser His Val Lys Gly Ala Asn Gly Ser Leu Thr Gly Pro Leu Thr Val Gly
            90              95                  100 atc atc ccc acg gcg

Ile Ile Pro Thr Ala
    105         108
```

The reading frame is likewise depicted as SEQ ID NO:19. SEQ ID NO:20 shows the amino acid sequence encoded by this reading frame. Position 20 in SEQ ID NO:20 corresponds to position 89 of SEQ ID NO:2, 4, 6 or 8.

Very particularly preferred nucleic acid molecules include at least a nucleotide sequence corresponding to position 958 to 1074 of SEQ ID NO:7, or at least a nucleotide sequence corresponding to position 838 to 1194 of SEQ ID NO: 7, or at least a nucleotide sequence corresponding to position 718 to 1314 of SEQ ID NO:7, or at least a nucleotide sequence corresponding to position 598 to 1434 of SEQ ID NO:7, or at least a nucleotide sequence corresponding to position 478 to 1554 of SEQ ID NO:7, or at least a nucleotide sequence corresponding to position 358 to 1674 of SEQ ID NO:7, or at least a nucleotide sequence corresponding to position 310 to 1722 of SEQ ID NO:7, or at least a nucleotide sequence corresponding to position 307 to 1725 of SEQ ID NO:7 or at least a nucleotide sequence corresponding to position 303 to 1728 of SEQ ID NO:7, with thymine being present at position 731 where appropriate.

The reading frames according to the invention, as shown by way of example in SEQ ID NO:17 and 19 as nucleotide sequence and in SEQ ID NO:18 and SEQ ID NO:20 in the form of the encoded amino acid sequence, may additionally comprise one or more mutations which lead to one or more conservative amino acid exchanges. The mutations preferably lead to a maximum of 4%, to a maximum of 2% or to a maximum of 1% conservative amino acid exchanges. The reading frames according to the invention may further comprise one or more silent mutations. The reading frames according to the invention preferably comprise not more than 4% and particularly preferably not more than 2% to not more than 1% silent mutations.

The isolated polynucleotides according to the invention can be used to produce recombinant strains of microorganisms which, in an improved manner compared with the initial or parent strain, release amino acids into the medium surrounding them or accumulate them in the interior of cells.

A widespread method for incorporating mutations into genes of coryneform bacteria is that of allele exchange, which is also known under the name "gene replacement". In this method, a DNA fragment which comprises the mutation of interest is transferred into the desired strain of a coryneform bacterium, and the mutation is incorporated by at least two recombination events or crossover events into the chromosome of the desired strain, or the sequence of a gene present in the relevant strain is exchanged for the mutated sequence.

Schwarzer and Pühler (Bio/Technology 9, 84-87 (1991)) used this method in order to incorporate a lysA allele which harboured a deletion, and in order to incorporate a lysA allele which harboured an insertion, into the chromosome of *C. glutamicum* instead of the wild-type gene. Schafer et al. (Gene 145, 69-73 (1994)) employed this method to incorporate a deletion into the hom-thrB operon of *C. glutamicum*. Nakagawa et al. (EP 1108790) and Ohnishi et al. (Applied Microbiology and Biotechnology 58(2), 217-223 (2002)) employed this method to incorporate various mutations starting from the isolated alleles into the chromosome of *C. glutamicum*. Nakagawa et al. were able in this way to incorporate a mutation referred to as Val59Ala into the homoserine dehydrogenase gene (hom), a mutation referred to as Thr311Ile into the aspartate kinase gene (lysC or ask), a mutation referred to as Pro458Ser into the pyruvate carboxylase gene (pyc) and a mutation referred to as Ala213Thr into the glucose-6-phosphate dehydrogenase gene (zwf) of *C. glutamicum* strains.

A polynucleotide according to the invention which can be used for a method according to the invention includes the complete region as shown for example in SEQ ID NO:5, or includes part of the coding region such as, for example, the nucleotide sequence which codes for at least the amino acid sequence corresponding to position 70 to 108 of SEQ ID NO:6 or 8 and which are depicted as SEQ ID NO:17 and 18. The part of the coding region corresponding to SEQ ID NO:17 and 18 includes a length of ≥117 nucleobases. The parts of SEQ ID NO:7 which are preferred are those including at least the sequence between position 1194 and 838, and correspondingly having a length of ≥357 nucleobases. The parts of SEQ ID NO:7 which are particularly preferred are those including at least the sequence between position 1314 and 718, and correspondingly having a length of ≥597 nucleobases. The parts of SEQ ID NO:7 which are very particularly preferred are those including at least the sequence between position 1434 and 598, and correspondingly having a length of ≥837 nucleobases.

The DNA fragment comprising the mutation of interest is in this method typically present in a vector, in particular a plasmid, which preferably undergoes only limited or no replication by the strain to be provided with the mutation. In general, a bacterium of the genus *Escherichia*, preferably of the species *Escherichia coli*, is used as auxiliary or intermediate host in which the vector can be replicated.

Examples of such plasmid vectors are the pK*mob and pK*mobsacB vectors described by Schäfer et al. (Gene 145, 69-73 (1994)), such as, for example, pK18mobsacB, and the vectors described in WO 02/070685 and WO 03/014362. These are replicative in *Escherichia coli*, but not in coryneform bacteria. Particularly suitable vectors are those comprising a gene with a conditionally negatively dominant effect such as, for example, the sacB gene (laevan sucrase gene) of, for example, *Bacillus* or the galK gene (galactose kinase gene) of, for example, *Escherichia coli*. (A gene with a conditionally negatively dominant effect means a gene which under certain conditions is disadvantageous, for example toxic, for the host but, under other conditions, has no negative effects on the host harbouring the gene.) These make it possible to select for recombination events in which the vector is eliminated from the chromosome. In addition, Nakamura et al. (U.S. Pat. No. 6,303,383) described a temperature-sensitive plasmid for coryneform bacteria which is able to replicate only at temperatures below 31° C.

The vector is then transferred into the coryneform bacterium by conjugation, for example by the method of Schafer (Journal of Bacteriology 172, 1663-1666 (1990)) or transformation for example by the method of Dunican and Shivnan (Bio/Technology 7, 1067-1070 (1989)) or the method of Thierbach et al. (Applied Microbiology and Biotechnology 29, 356-362 (1988)). The transfer of the DNA can where appropriate also be achieved by particle bombardment.

Homologous recombination by means of a first crossover event which brings about integration, and of a suitable second crossover event which brings about an excision in the target gene or in the target sequence achieves incorporation of the mutation and results in a recombinant bacterium.

Methods which can be employed for identifying and characterizing the resulting strains are inter alia those of Southern blotting hybridization, of the polymerase chain reaction, of sequence determination, the method of fluorescence resonance energy transfer (FRET) (Lay et al. Clinical Chemistry 43, 2262-2267 (1997)) or methods of enzymology.

The invention accordingly further relates to a method for producing a coryneform bacterium, in which
  a) a polynucleotide according to the invention is transferred into a coryneform bacterium,
  b) the oxyR gene which is present in the chromosome of the coryneform bacterium and which codes for an amino acid sequence with L-alanine at position 89 or at a comparable position of the amino acid sequence is exchanged for the polynucleotide from a) which codes for an amino acid sequence which has at position 89 or at a comparable position of the amino acid sequence another proteinogenic L-amino acid, preferably L-valine, and
  c) the coryneform bacterium obtained as in step a) and b) is propagated.

A recombinant coryneform bacterium which comprises instead of the wild-type oxyR gene one (1) oxyR allele according to the invention is obtained in this way.

A further method according to the invention for producing a microorganism consists of
  a) transferring a polynucleotide according to the invention which codes a polypeptide having OxyR transcription regulator activity into a microorganism,
  b) replicating the polynucleotide in the microorganism, and
  c) propagating the microorganism obtained as in step a) and b).

A recombinant microorganism which comprises at least one (1) copy or a plurality of copies of a polynucleotide according to the invention which codes for an OxyR transcription regulator which comprises at position 89 or a comparable position of the amino acid sequence of the encoded polypeptide, one of the proteinogenic amino acids except L-alanine, with preference for exchange for L-valine, is obtained in this way.

The invention further accordingly relates to hosts or host cells, preferably microorganisms, particularly preferably coryneform bacteria and bacteria of the genus *Escherichia*, which comprise the polynucleotides according to the invention. The invention likewise relates to microorganisms which have been produced using the isolated polynucleotides. Microorganisms or bacteria of this type are also referred to as recombinant microorganisms or recombinant bacteria. The invention likewise relates to vectors which comprise the polynucleotides according to the invention. Finally, the invention likewise relates to hosts which comprise these vectors.

The isolated polynucleotides according to the invention can likewise be used to achieve overexpression of the polypeptides encoded by them.

Overexpression means in general an increase in the intracellular concentration or activity of a ribonucleic acid, of a protein or of an enzyme. In the case of the present invention, oxyR alleles or polynucleotides which code for OxyR transcription regulators which comprise at position 89 of the amino acid sequence of the encoded polypeptide one of the proteinogenic amino acids except L-alanine, with preference for exchange for L-valine, are overexpressed.

It is known that N-terminal amino acids, especially the N-terminal methionine, can be eliminated from the polypeptide formed, by the host's own enzymes—called aminopeptidases.

The said increase in the concentration or activity of a gene product can be achieved for example by increasing the copy number of the appropriate polynucleotides by at least one copy.

A widely used method for increasing the copy number consists of incorporating the appropriate gene or allele into a vector, preferably a plasmid, which is replicated by a coryneform bacterium. Suitable plasmid vectors are for example pZ1 (Menkel et al., Applied and Environmental Microbiology (1989) 64: 549-554) or the pSELF vectors described by Tauch et al. (Journal of Biotechnology 99, 79-(2002)). A review article on the topic of plasmids in *Corynebacterium glutamicum* is to be found in Tauch et al. (Journal of Biotechnology 104, 27-40 (2003)).

Another widely used method for achieving overexpression is the method of chromosomal gene amplification. In this method, at least one additional copy of the gene or allele of interest is introduced into the chromosome of a coryneform bacterium.

In one embodiment, as described for example in Reinscheid et al. (Applied and Environmental Microbiology 60, 126-132 (1994)) for the hom-thrB operon, a plasmid which is non-replicative in *C. glutamicum* and which comprises the gene of interest is transferred into a coryneform bacterium. The strain resulting after homologous recombination by means of a crossover event comprises at least two copies of the relevant gene or allele.

In another embodiment, which is described in WO 03/040373 and US-2003-0219881-A1, one or more copy(ies) of the gene of interest is introduced by means of at least two recombination events into a desired site in the chromosome of *C. glutamicum*. In this way, for example, a copy of a lysC allele which codes for an L-lysine-insensitive aspartate kinase was incorporated into the gluB gene of *C. glutamicum*.

In a further embodiment, which is described in WO 03/014330 and US-2004-0043458-A1, at least one further copy of the gene of interest is incorporated, preferably in tandem arrangement to the previously present gene or allele, at the natural site by means of at least two recombination events. In this way, for example, a tandem duplication of a lysC$^{FBR}$ allele was achieved at the natural lysC gene site.

Finally, it is possible to increase the copy number with the aid of transposons and IS elements (see: U.S. Pat. No. 5,804, 414, U.S. Pat. No. 5,591,577).

A further method for achieving an overexpression consists of linking the appropriate gene or allele in a functional manner (operably linked) to a promoter or to an expression cassette. Suitable promoters for *Corynebacterium glutamicum* are described for example in the review article by Patek et al. (Journal of Biotechnology 104(1-3), 311-323 (2003). It is possible in the same way to use the variants of the dapA promoter described by Vasicova et al. (Journal of Bacteriology 181, 6188-6191 (1999)), for example the promoter A25. A further possibility is to use the gap promoter of *Corynebacterium glutamicum* (EP 06007373). Finally, the well-known promoters T3, T7, SP6, M13, lac, tac and trc described by Amann et al. (Gene 69(2), 301-315 (1988)) and Amann and Brosius (Gene 40(2-3), 183-190 (1985)) can be used. A promoter of this type can be inserted for example upstream of the oxyR allele, typically at a distance of approximately 1-500 nucleotides from the start codon, of a recombinant coryneform bacterium which comprises another proteinogenic amine acid instead of the amino acid L-alanine which is naturally present at position 89. A promoter of this type can by its nature likewise be inserted upstream of the coding region of the oxyR allele of a mutant according to the invention. It is furthermore possible to link an isolated polynucleotide according to the invention which codes for a variant according to the invention of the OxyR transcription regulator to a promoter and to incorporate the resulting expression unit into an extra chromosomally replicating plasmid or into the chromosome of a coryneform bacterium.

A further possibility is to mutate the promoter region and regulatory region or the ribosome binding site which is located upstream of the structural gene. Expression is likewise improved by measures to prolong the lifespan of the mRNA. The enzymic activity is likewise enhanced in addition by preventing breakdown of the enzyme protein. A further possible alternative is overexpression of the relevant gene or allele through alteration of the composition of the media and management of the culture.

The activity or concentration of the appropriate protein is generally increased by the overexpression measures by at least 10%, 25%, 50%, 75%, 100%, 150%, 200%, 300%, 400% or 500%, maximally up to 1000% or 2000%, relative to the activity or concentration of the protein in the starting microorganism or parent strain. A starting microorganism or parent strain means a microorganism on which the measures of the invention are carried out.

The concentration of the protein can be determined by 1- and 2-dimensional protein gel fractionation and subsequent optical identification of the protein concentration using appropriate evaluation software in the gel. A useful method for preparing the protein gel in the case of coryneform bacteria and for identifying the proteins is the procedure described by Hermann et al. (Electrophoresis, 22:1712-23 (2001)). The protein concentration can likewise be determined by Western blot hybridization with an antibody specific for the protein to be detected (Sambrook et al., Molecular cloning: a laboratory manual. 2nd Ed. Cold Spring Harbor Laboratory Press, Cold Spring Harbor, N.Y., 1989) and subsequent optical evaluation with appropriate software to determine the concentration (Lohaus and Meyer (1998) Biospektrum 5:32-39; Lottspeich, Angewandte Chemie 38: 2630-2647 (1999)).

The invention accordingly relates to methods for overexpressing the OxyR transcription regulator according to the invention. One method according to the invention for overexpression consists inter alia of increasing the copy number of a polynucleotide according to the invention which codes for an OxyR transcription regulator variant in which one of the proteinogenic amino acids except L-alanine is present at position 89 or the corresponding position of the encoded amino acid sequence by at least one (1) or by a plurality of copies. A further method according to the invention consists of functionally linking a promoter to the polynucleotide.

The invention further relates to microorganisms which have an increased concentration or activity of the OxyR transcription regulator variants according to the invention in the interior of their cells.

It may additionally be advantageous for increased production of L-amino acids to overexpress various genes in the mutants or recombinant strains according to the invention. The use of endogenous genes is generally preferred.

"Endogenous genes" or "endogenous nucleotide sequences" mean the genes or nucleotide sequences, or alleles, present in the population of a species.

Thus, to produce L-lysine, it is possible to overexpress one or more of the genes selected from the group of a dapA gene coding for a dihydrodipicolinate synthase (DapA, EC No. 4.2.1.52), such as, for example, the dapA gene described in EP 0 197 335 of the wild type of *Corynebacterium glutamicum*, a lysA gene coding for a diaminopimelate decarboxylase (LysA, EC No. 4.1.1.20), such as, for example, the lysA gene described in U.S. Pat. No. 6,090,597 of *Corynebacterium glutamicum* ATCC13869, a zwf gene coding for a glucose-6-phosphate dehydrogenase (Zwf, EC No. 1.1.1.49), such as, for example, the zwf gene described in JP-A-09224661 and EP-A-1108790 of the wild type of *Corynebacterium glutamicum*, the zwf alleles of *Corynebacterium glutamicum* which are described in US-2003-0175911-A1 and which code for a protein having glucose-6-phosphate dehydrogenase activity, in which for example the L-alanine at position 243 of the amino acid sequence is replaced by L-threonine, or in which the L-aspartic acid at position 245 is replaced by L-serine, a pyc gene coding for a pyruvate carboxylase (Pyc, EC No. 6.4.1.1), such as, for example, the pyc gene described in DE-A-198 31 609 and EP 1108790 of the wild type of *Corynebacterium glutamicum*, the for the pyc allele of *Corynebacterium glutamicum* which is described in EP 1 108 790 and which codes for a protein having pyruvate carboxylase activity in which L-proline at position 458 of the amino acid sequence is replaced by L-serine, the pyc alleles of *Corynebacterium glutamicum* which are described in WO 02/31158 and in particular EP1325135B1 and which code for proteins having pyruvate carboxylase activity which harbour one or more of the amino acid exchanges selected from the group of L-valine at position 1 replaced by L-methionine, L-glutamic acid at position 153 replaced by L-asparatic acid, L-alanine at position 182 replaced by L-serine, L-alanine at position 206 replaced by L-serine, L-histidine at position 227 replaced by L-arginine, L-alanine at position 455 replaced by glycine and L-aspartic acid at position 1120 replaced by L-glutamic acid, a lysC gene coding for an aspartate kinase (LysC, EC No. 2.7.2.4), such as, for example, the lysC gene described as SEQ ID NO:281 in EP-A-1108790 (see also access number AX120085 and 120365) and the lysC gene described as SEQ ID NO:25 in WO 01/00843 (see access number AX063743) of the wild type of *Corynebacterium glutamicum*, a $lysC^{FBR}$ allele coding for a feedback-resistant aspartate kinase variant, in particular corresponding to Table 1, a lysE gene coding for a lysine export protein (LysE), such as, for example, the lysE gene described in DE-A-195 48 222 of the wild-type *Corynebacterium glutamicum*, the aat gene coding for an aspartate aminotransferase (Aat, EC No. 2.6.1.1) (the aat gene of *Corynebacterium glutamicum* ATCC13032 is described for example in Kalinowski et al. (Journal of Biotechnology 104 (1-3), 5-25 (2003); see also access number NC_006958). It is referred to therein as aspB gene. In U.S. Pat. No. 6,004,773, a gene coding for an aspartate aminotransferase is referred to as aspC. Marienhagen et al. (Journal of Bacteriology 187 (22), 7693-7646 (2005)) referred to the aat gene as aspT gene, the zwa1 gene coding for the Zwa1 protein of the wild type of *Corynebacterium glutamicum* (U.S. Pat. No. 6,632,644).

It may further be advantageous for the production of L-lysine, besides the use of the alleles according to the invention of the oxyR gene simultaneously, where appropriate with simultaneous overexpression of at least one of the genes selected from the aforementioned group of genes, to attenuate or switch off one or more of the endogenous genes selected from the group of a pgi gene coding for glucose-6-phosphate isomerase (Pgi, EC No. 5.3.1.9), such as, for example, the pgi gene described in U.S. Pat. No. 6,586,214 and U.S. Pat. No. 6,465,238 of *Corynebacterium glutamicum*, a hom gene coding for homoserine dehydrogenase (Hom, EC No. 1.1.1.3), such as, for example, the hom gene described in EP-A-0131171 of *Corynebacterium glutamicum*, a thrB gene coding for homoserine kinase (ThrB, EC No. 2.7.1.39), such as, for example, the thrB gene described by Peoples et al. (Molecular Microbiology 2 (1988): 63-72) of *Corynebacterium glutamicum* and a pfkB gene coding for phosphofructokinase (PfkB, EC No. 2.7.1.56), such as, for example, the pfkB gene described in WO 01/00844 (sequence No. 57) of *Corynebacterium glutamicum*, an mdh gene coding for malate dehydrogenase (Mdh, EC No. 1.1.1.37) as described for example in WO 02/02778, an mqo gene coding for malate-quinone oxidoreductase (Mqo, EC No. 1.1.99.16), as described for example in U.S. Pat. No. 7,094,106 and PCT/EP2005/057216.

The term "attenuation" describes in this connection the reduction or switching off of the intracellular activity of one or more enzymes (proteins) in a microorganism which are encoded by the appropriate DNA, by for example using a weak promoter or using a gene or allele which codes for a corresponding enyme with a low activity, or inactivates the corresponding gene or enzyme (protein) and, where appropriate, combining these measures.

The attenuation measures generally reduce the activity or concentration of the corresponding protein to 0 to 75%, 0 to 50%, 0 to 25%, 0 to 10% or 0 to 5% of the activity or concentration of the wild-type protein, or of the activity or concentration of the protein in the starting microorganism.

Mutations suitable for generating an attenuation are transitions, transversions, insertions and deletions of at least one (1) base pair or nucleotide. Depending on the effect of the amino acid exchange caused by the mutation on the enzymic activity, reference is made to missense mutations or nonsense mutations. The missense mutation leads to exchange of a given amino acid in a protein for another one, the amino acid exchange being in particular a non-conservative one. This impairs the ability to function or activity of the protein and reduces it to a value of from 0 to 75%, 0 to 50%, 0 to 25%, 0 to 10% or 0 to 5%. The nonsense mutation leads to a stop codon in the coding region of the gene and thus to premature termination of translation. Insertions or deletions of at least one base pair in a gene lead to frame shift mutations which lead to incorrect amino acids being incorporated or the translation being terminated prematurely. If the mutation results in a stop codon in the coding region, this likewise leads to premature termination of transation. The said measures are preferably carried out in the 5'-terminal part of the coding region which codes for the N terminus of the polypeptide. If the total length of a polypeptide (measured as number of chemically linked L-amino acids) is referred to as 100%, the part of the amino acid sequence belonging to the N terminus of the polypeptide—in the context of the present invention—comprises 80% of the L-amino acids following the start amino acid L-formylmethionine.

Further instructions for generating such mutations belong to the state of the art and can be found in known textbooks of genetics and molecular biology such as, for example, the textbook by Knippers ("Molekulare Genetik", 6th edition, Georg Thieme Verlag, Stuttgart, Germany, 1995), that of Winnacker ("Gene and Klone", VCH Verlagsgesellschaft, Weinheim, Germany, 1990) or that of Hagemann ("Allgemeine Genetik", Gustav Fischer Verlag, Stuttgart, 1986). Further measures are described in the prior art.

One method for targeted reduction of gene expression consists of placing the gene to be attenuated under the control of a promoter which can be induced by addition of metered amounts of IPTG (isopropyl β-D-thiogalactopyranoside), such as, for example, the trc promoter or the tac promoter. Suitable for this purpose are vectors such as, for example, the *Escherichia coli* expressions vector pXK99E (WO0226787; deposited in accordance with the Budapest Treaty on 31 Jul. 2001 in DHSalpha/pXK99E as DSM14440 at the Deutsche Sammlung für Mikroorganismen and Zellkulturen (DSMZ, Brunswick, Germany)) or pVWEx2 (Wendisch, Ph. D. thesis, Berichte des Forschungszentrums Jülich, Jül-3397, ISSN 0994-2952, Jülich, Germany (1997)), which make IPTG-dependent expression of the cloned gene possible in *Corynebacterium glutamicum*.

This method has been employed for example in the Patent WO0226787 for the regulated expression of the deaD gene by integration of the vector pXK99EdeaD into the genome of *Corynebacterium glutamicum* and by Simic et al. (Applied and Environmental Microbiology 68: 3321-3327 (2002)) for the regulated expression of the glyA gene by integration of the vector pK18mobglyA' into *Corynebacterium glutamicum*.

A further method for specifically reducing gene expression is the antisense technique, where short oligodeoxynucleotides or vectors are brought into the target cells to synthesize longer antisense RNA. The antisense RNA is able to bind there to complementary segments of specific mRNAs and reduce their stability, or block translatability. One example thereof is to be found by the skilled person in Srivastava et al. (Applied Environmental Microbiology 2000 October; 66 (10): 4366-4371).

The isolated coryneform bacteria obtained by the measures of the invention show a secretion or production of the desired amino acid in a fermentation process which is increased by comparison with the starting strain or parent strain employed.

Isolated bacteria mean the isolated and generated mutants and recombinant bacteria, especially coryneform bacteria, according to the invention which comprise an oxyR allele which codes for an OxyR transcription regulator which comprises the described amino acid exchange at position 89 of the amino acid sequence.

The output of the isolated bacteria or of the fermentation process using the same in relation to one or more of the parameters selected from the group of the product concentration (product per volume), the product yield (product formed per carbon source consumed) and the product formation (product formed per volume and time) or else other process parameters and combinations thereof is improved by at least 0.5%, at least 1%, at least 1.5% or at least 2% relative to the starting strain or parent strain or to the fermentation process using the same.

The isolated coryneform bacteria according to the invention can be cultured continuously—as described for example in PCT/EP2004/008882—or discontinuously in a batch process (batch cultivation) or in fed or repeated fed batch processes for the purpose of producing L-amino acids. A summary of a general nature about known cultivation methods is available in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Brunswick/Wiesbaden, 1994)).

The culture medium or fermentation medium to be used must satisfy in a suitable manner the demands of the respective strains. Descriptions of culture media of various microorganisms are present in the handbook "Manual of Methods for General Bacteriology" of the American Society for Bacteriology (Washington D.C., USA, 1981). The terms culture medium, fermentation medium and nutrient medium or medium are mutually exchangeable.

Carbon sources which can be used are sugars and carbohydrates such as, for example, glucose, sucrose, lactose, fructose, maltose, molasses, sucrose-containing solutions from sugarbeet or sugarcane production, starch, starch hydrolysate and cellulose, oils and fats such as, for example, soya oil, sunflower oil, peanut oil and coconut fat, fatty acids such as, for example, palmitic acid, stearic acid and linoleic acid, alcohols such as, for example, glycerol, methanol and ethanol and organic acids such as, for example, acetic acid. These substances can be used singly or as mixture.

Nitrogen sources which can be used are organic nitrogen-containing compounds such as peptone, yeast extract, meat extract, malt extract, corn steep liquor, soybean flour and urea or inorganic compounds such as ammonium sulphate, ammonium chloride, ammonium phosphate, ammonium carbonate and ammonium nitrate. The nitrogen sources can be used singly or as mixture.

Phosphorus sources which can be used are phosphoric acid, potassium dihydrogen phosphate or dipotassium hydrogen phosphate or the corresponding sodium-containing salts.

The culture medium must additionally comprise salts for example in the form of chlorides or sulphates of metals such as, for example, sodium, potassium, magnesium, calcium and iron, such as, for example, magnesium sulphate or iron sulphate, which are necessary for growth. Finally, essential growth factors such as amino acids, for example homoserine and vitamins, for example thiamine, biotin or pantothenic acid, can be employed in addition to the abovementioned substances. It is moreover possible to add to the culture medium suitable precursors of the respective amino acid.

The said starting materials can be added to the culture in the form of a single batch or be fed during the culturing in a suitable manner.

To control the pH of the culture, basic compounds such as sodium hydroxide, potassium hydroxide, ammonia or aqueous ammonia or acidic compounds such as phosphoric acid or sulphuric acid are employed in a suitable manner. The pH is generally adjusted to a value of from 6.0 to 9.0, preferably 6.5 to 8. To control foaming, it is possible to employ antifoams such as, for example, fatty acid polyglycol esters. To maintain the stability of plasmids, it is possible to add to the medium suitable selectively acting substances such as, for example, antibiotics. In order to maintain aerobic conditions, oxygen or oxygen-containing gas mixtures such as, for example, air are introduced into the culture. It is likewise possible to use liquids enriched with hydrogen peroxide. The fermentation is carried out where appropriate with excess pressure, for example with a pressure of from 0.03 to 0.2 MPa. The temperature of the culture is normally 20° C. to 45° C. and preferably 25° C. to 40° C. In batch processes, the culturing is continued until a maximum of the desired amino acid has formed. This aim is normally reached within 10 hours to 160 hours. In continuous processes, longer culturing times are possible.

Suitable fermentation media are described inter alia in U.S. Pat. No. 6,221,636, in U.S. Pat. No. 5,840,551, in U.S. Pat. No. 5,770,409, in U.S. Pat. No. 5,605,818, in U.S. Pat. No. 5,275,940, in U.S. Pat. No. 4,275,157 and in U.S. Pat. No. 4,224,409.

Methods for determining L-amino acids are known in the state of the art. The analysis can take place for example as described by Spackman et al. (Analytical Chemistry, 30, (1958), 1190) by anion exchange chromatography with subsequent ninhydrin derivatization, or it can take place by reversed phase HPLC as described by Lindroth et al. (Analytical Chemistry (1979) 51: 1167-1174).

The invention accordingly relates to a process for producing an L-amino acid in which
a) an isolated coryneform bacterium is fermented in a suitable medium, where the bacterium comprises a gene coding for a polypeptide having OxyR transcription regulator activity, where the L-alanine at position 89 in the amino acid sequences of the polypeptide, or the corresponding position, is replaced by another proteinogenic amino acid, preferably L-valine, and
b) the L-amino acid is accumulated in the fermentation broth or in the cells of the isolated coryneform bacterium.

This is generally followed by collecting the L-amino acid which has accumulated in the nutrient medium or in the fermentation broth and/or in the cells of the bacteria in order to obtain a solid or liquid product.

A fermentation broth means a fermentation medium in which a microorganism has been cultured for a certain time and at a certain temperature. The fermentation medium, or the media employed during the fermentation, comprise(s) all the substances and components ensuring growth of the microorganism and formation of the desired amino acid.

When the fermentation is complete, the resulting fermentation broth accordingly comprises a) the biomass of the microorganism which has been produced as a result of the growth of the cells of the microorganism, b) the desired amino acid formed during the fermentation, c) the organic by-products formed during the fermentation, and d) the constituents of the fermentation medium/media employed or of the starting materials such as, for example, vitamins such as biotin, amino acids such as homoserine or salts such as magnesium sulphate, which have not been consumed by the fermentation.

The organic by-products include substances which are produced by the microorganisms employed in the fermentation where appropriate in addition to the respective desired L-amino acid and are secreted where appropriate. These include L-amino acids which account for less than 30%, 20% or 10% compared with the desired amino acid. These further include organic acids which have one to three carboxyl groups, such as, for example, acetic acid, lactic acid, citric acid, malic acid or fumaric acid. Also included finally are sugars such as, for example, trehalose.

Typical fermentation broths suitable for industrial purposes typically have an amino acid content of 30 g/kg to 200 g/kg or 40 g/kg to 175 g/kg or 50 g/kg to 150 g/kg. The biomass content (as dry biomass) is generally 20 to 50 g/kg.

In the case of the amino acid L-lysine, substantially four different product forms are known in the state of the art.

One group of L-lysine-containing products includes concentrated aqueous alkaline solutions of purified L-lysine (EP-B-0534865). A further group as described for example in U.S. Pat. No. 6,340,486 and U.S. Pat. No. 6,465,025 includes aqueous acidic biomass-containing concentrates of L-lysine-containing fermentation broths. The best-known group of solid products includes powder or crystalline forms of purified or pure L-lysine which is typically in the form of a salt such as, for example, L-lysine monohydrochloride. A further group of solid product forms is described for example in EP-B-0533039. Besides L-lysine, the product form described therein comprises most of the starting materials which were used during the fermentative production and were not consumed and, where appropriate, the biomass of the microorganism employed with a content of >0%-100%.

In the case of the amino acids L-valine, L-isoleucine, L-proline, L-tryptophan and L-homoserine, the product forms known in the prior art are substantially those containing the relevant amino acids in purified or pure form (≥95% by weight or ≥98% by weight).

Corresponding to the different product forms, a wide variety of processes are known with which the L-amino acid is collected, isolated or purified from the fermentation broth in order to produce the L-amino acid-containing product or the purified L-amino acid.

Solid pure L-amino acids are produced substantially by using methods of ion exchange chromatography, where appropriate with use of activated carbon, and methods of crystallization. In the case of lysine, the corresponding base or a corresponding salt such as, for example, the monohydrochloride (Lys-HCl) or lysine sulphate ($Lys_2$-$H_2SO_4$) is obtained in this way.

In the case of lysine, EP-B-0534865 describes a process for producing aqueous, basic L-lysine-containing solutions from fermentation broths. In the process described therein, the biomass is removed from the fermentation broth and discarded. A base such as, for example, sodium, potassium or ammonium hydroxide is used to adjust a pH of between 9 to 11. The mineral constituents (inorganic salts) are removed from the broth after concentration and cooling by crystallization and either used as fertilizers or discarded.

In processes for producing lysine using the bacteria according to the invention, processes resulting in products which comprise components of the fermentation broth are also employed. These are used in particular as animal feed additives.

Depending on requirements, the biomass can be removed wholly or partly from the fermentation broth by separation methods such as, for example, centrifugation, filtration, decantation or a combination thereof, or be left completely therein. Where appropriate, the biomass or the biomass-containing fermentation broth is inactivated during a suitable process step, for example by thermal treatment (heating) or by addition of acid.

The chemical constituents of the biomass are inter alia the cell envelope, for example the peptidoglycan and the arabinogalactan, the protein or polypeptide, for example the OxyR transcription regulator polypeptide, lipids and phospholipids and nucleic acids (DNA and RNA), for example polynucleotides comprising the mutation according to the invention. As a result of the measures of inactivation and/or of the further process steps (for example acidification, spray drying, granulation etc.), nucleic acids are typically present as fragments with a length of inter alia ≥40-60 bp, >60-80 bp, >80-100 bp, >100-200 bp, >200-300 bp, >300-400 bp, >400-500 bp, >500-750 bp, >750-1000 bp, >1000-1250 bp, >1250-1500 bp, >1500-1750 bp, >1750-2000 bp, >2000-2500 bp, >2500-3000 bp, >3000-4000 bp, >4000-5000 bp.

In one procedure, the biomass is removed completely or almost completely so that no (0%) or not more than 30%, not more than 20%, not more than 10%, not more than 5%, not more than 1% or not more than 0.1% biomass remains in the product produced. In a further procedure, the biomass is not removed, or is removed only in small proportions, so that all (100%) or more than 70%, 80%, 90%, 95%, 99% or 99.9% biomass remains in the product produced. In one process according to the invention, accordingly, the biomass is removed in proportions to ≥0% to ≥100%.

Finally, the fermentation broth obtained after the fermentation can be adjusted, before or after the complete or partial removal of the biomass, to an acidic pH with an inorganic acid such as, for example, hydrochloric acid, sulphuric acid or phosphoric acid or organic acid such as, for example, propionic acid (GB 1,439,728 or EP 1 331 220). It is likewise possible to acidify the fermentation broth with the complete content of biomass (U.S. Pat. No. 6,340,486 or U.S. Pat. No. 6,465,025). Finally, the broth can also be stabilized by adding sodium bisulphite ($NaHSO_3$, GB 1,439,728) or another salt, for example ammonium, alkali metal or alkaline earth metal salt of sulphurous acid.

During the removal of the biomass, organic or inorganic solids present where appropriate in the fermentation broth are partially or completely removed. The organic by-products dissolved in the fermentation broth and the dissolved unconsumed components of the fermentation medium (starting materials) remain at least partly (>0%), preferably to the extent of at least 25%, particularly preferably to the extent of at least 50% and very particularly preferably to the extent of at least 75% in the product. Where appropriate, they also remain completely (100%) or almost completely, meaning >95% or >98%, in the product. In this sense, the term "based on fermentation broth" means that the product comprises at least part of the components of the fermentation broth.

Subsequently, water is removed or thickened or concentrated from the broth by known methods such as, for example, with the aid of a rotary evaporator, thin-film evaporator, falling film evaporator, by reverse osmosis or by nanofiltration. This concentrated fermentation broth can then be worked up to free-flowing products, in particular to a fine-particle powder or preferably coarse granules, by methods of freeze drying, of spray drying, of spray granulation or by other processes as described for example in the circulating fluidized bed according to PCT/EP2004/006655. A desired product is isolated where appropriate from the resulting granules by screening or dust removal.

It is likewise possible to dry the fermentation broth directly, i.e. without previous concentration by spray drying or spray granulation.

"Free-flowing" means powders which flow unimpeded out of a series of glass orifice vessels with orifices of different sizes at least out of the vessel with a 5 mm (millimeters) orifice (Klein: Seifen, Öle, Fette, Wachse 94, 12 (1968)).

"Fine-particle" means a powder predominantly (>50%) of a particle size of diameter from 20 to 200 μm.

"Coarse" means a product predominantly (>50%) of a particle size of diameter from 200 to 2000 μm.

The particle size determination can be carried out by methods of laser diffraction spectrometry. Corresponding methods are described in the textbook on "Teilchengrößenmessung in der Laborpraxis" by R. H. Müller and R. Schuhmann, Wissenschaftliche Verlagsgesellschaft Stuttgart (1996) or in the textbook "Introduction to Particle Technology" by M. Rhodes, published by Wiley & Sons (1998).

The free-flowing, fine-particle powder can in turn be converted by suitable compaction or granulation processes into a coarse, very free-flowing, storable and substantially dust-free product.

The term "dust-free" means that the product comprises only small proportions (<5%) of particle sizes below 100 μm in diameter.

"Storable" in the sense of this invention means a product which can be stored for at least one (1) year or longer, preferably at least 1.5 years or longer, particularly preferably two (2) years or longer, in a dry and cool environment without any substantial loss (<5%) of the respective amino acid occurring.

The invention accordingly further relates to a process for producing an L-amino acid, preferably L-lysine or L-tryptophan, containing product, preferably animal feed additive, from fermentation broths, characterized by the steps a) culturing and fermentation of an L-amino acid-secreting coryneform bacterium which comprises at least one oxyR allele which codes for a polypeptide having OxyR transcription regulator activity, which includes an amino acid sequence in which at position 89 or the comparable position one of the proteinogenic amino acids except L-alanine, preferably L-valine, is present, in a fermentation medium, b) removal of the biomass formed during the fermentation in an amount of from 0 to 100% by weight, and c) drying of the fermentation broth obtained as in a) and/or b) in order to obtain the product in the desired powder or granular form, where an acid selected from the group of sulphuric acid, phosphoric acid or hydrochloric acid is added where appropriate before step b) or c). Step a) or b) is preferably followed by removal of water from the L-amino acid-containing fermentation broth (concentration).

The invention further relates to a process for producing a lysine sulphate-containing product which is described in principle in DE 102006016158, and in which the fermentation broth obtained using the microorganisms according to the invention, from which the biomass has been removed completely or partly where appropriate, is further processed by carrying out a process which includes at least the following steps:

a) the pH is reduced by adding sulphuric acid to 4.0 to 5.2, in particular 4.9 to 5.1, and a molar sulphate/L-lysine ratio of from 0.85 to 1.2, preferably 0.9 to 1.0, particularly preferably >0.9 to <0.95, is adjusted in the broth, where appropriate by adding a further or a plurality of sulphate-containing compound(s) and b) the mixture obtained in this way is concentrated by removal of water, and granulated where appropriate, where one or both of the following measures is/are carried out where appropriate before step a):

c) measurement of the molar sulphate/L-lysine ratio to ascertain the required amount of sulphate-containing compound(s)

d) addition of a sulphate-containing compound selected from the group of ammonium sulphate, ammonium bisulphate and sulphuric acid in appropriate ratios.

Where appropriate, also before step b), a salt of sulphurous acid, preferably alkali metal bisulfite, particularly preferably sodium bisulfite, is added in a concentration of 0.01 to 0.5 by weight, preferably 0.1 to 0.3% by weight, particularly preferably 0.1 to 0.2% by weight, based on the fermentation broth.

Preferred sulphate-containing compounds which should be mentioned in the context of the abovementioned process steps are in particular ammonium sulphate and/or ammonium bisulphate or corresponding mixtures of ammonia and sulphuric acid and sulphuric acid itself.

The molar sulphate/L-lysine ratio V is calculated by the formula: $V=2\times[SO_4^{2-}]/[\text{L-lysine}]$. This formula takes account of the fact that the $SO_4^{2-}$ anion has two charges. A ratio of V=1 means that the stoichiometric composition $Lys_2(SO_4)$ is present, whereas the finding with a ratio of V=0.9 is a 10% sulphate deficit and with a ratio of V=1.1 is a 10% sulphate excess.

It is advantageous to employ during the granulation or compaction the usual organic or inorganic auxiliaries or carriers such as starch, gelatin, cellulose derivatives or similar substances, as normally used in the processing of food products or feeds as binders, gelling agents or thickeners, or further substances such as, for example, silicas, silicates (EP0743016A) or stearates.

It is further advantageous to provide the surface of the resulting granules with oils as described in WO 04/054381. Oils which can be used are mineral oils, vegetable oils or mixtures of vegetable oils. Examples of such oils are soya oil, olive oil, soya oil/lecithin mixtures. In the same way, silicone oils, polyethylene glycols or hydroxyethylcellulose are also suitable. Treatment of the surfaces with the said oils achieves an increased abrasion resistance of the product and a reduction in the dust content. The oil content in the product is 0.02 to 2.0% by weight, preferably 0.02 to 1.0% by weight, and very particularly preferably 0.2 to 1.0% by weight based on the total amount of the feed additive.

Preferred products have a proportion of ≥97% by weight of a particle size of from 100 to 1800 μm or a proportion of ≥95% by weight of a particle size of from 300 to 1800 μm diameter. The proportion of dust, i.e. particles with a particle size <100 μm, is preferably >0 to 1% by weight, particularly preferably not exceeding 0.5% by weight.

However, alternatively, the product may also be absorbed on an organic or inorganic carrier known and customary in the processing of feeds, such as, for example, silicas, silicates, meals, brans, flours, starches, sugars or others, and/or be mixed and stabilized with customary thickeners and binders. Examples of use and processes therefor are described in the literature (Die Mühle+Mischfuttertechnik 132 (1995) 49, page 817).

Finally, the product can also be brought by coating processes with film-formers such as, for example, metal carbonates, silicas, silicates, alginates, stearates, starches, gums and cellulose ethers as described in DE-C-4100920 to a state in which is stable to digestion by animal stomachs, especially the stomach of ruminants.

To adjust a desired amino acid concentration in the product it is possible, depending on requirements, to add the appropriate amino acid during the process in the form of a concentrate or, if appropriate, of a substantially pure substance or its salt in liquid or solid form. These can be added singly or as mixtures to the resulting or concentrated fermentation broth, or else during the drying or granulation process.

The invention further relates to a process for producing a solid lysine-containing product as described in principle in US 20050220933, and which includes the working up of the fermentation broth obtained using the microorganisms according to the invention, in the following steps:

a) filtration of the fermentation broth, preferably with a membrane filter, to result in a biomass-containing sludge and a filtrate,
b) concentration of the filtrate, preferably so as to result in a solids content of from 48 to 52% by weight,
c) granulation of the concentrate obtained in step b), preferably at a temperature of from 50° C. to 62° C., and
d) coating of the granules obtained in c) with one or more of the coating agent(s).

The coating agents used for the coating in step d) are preferably selected from the group consisting of
d1) the biomass obtained in step a),
d2) an L-lysine-containing compound, preferably selected from the group of L-lysine hydrochloride or L-lysine sulphate,
d3) a substantially L-lysine-free substance with an L-lysine content of <1% by weight, preferably <0.5% by weight, preferably selected from the group of starch, carageenan, agar, silicas, silicates, meals, brans and flours, and
d4) a water-repellant substance, preferably selected from the group of oils, polyethylene glycols and liquid paraffins.

In the case of lysine, the ratio of the ions during the production of lysine-containing products is preferably adjusted so that the equivalent ion ratio corresponding to the following formula

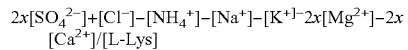

$$2x[SO_4^{2-}]+[Cl^-]-[NH_4^+]-[Na^+]-[K^+]-2x[Mg^{2+}]-2x[Ca^{2+}]/[L\text{-}Lys]$$

results in 0.68 to 0.95, preferably 0.68 to 0.90, as described by Kushiki et al. in US 20030152633 (the molar concentrations are to be given in the "[ ]").

In the case of lysine, the solid product produced in this way has, based on the fermentation broth, a lysine content (as lysine base) of 10% by weight to 70% by weight or 20% by weight to 70% by weight, preferably 30% by weight to 70% by weight and very particularly preferably of 40% by weight to 70% by weight, based on the dry matter of the product. Maximum contents of lysine base of 71% by weight, 72% by weight, 73% by weight are likewise possible.

In the case of an electrically neutral amino acid such as L-tryptophan, the solid product produced in this way has, based on the fermentation broth, an amino acid content of at least 5% by weight, 10% by weight, 20% by weight, 30% by weight and at most 50% by weight, 60% by weight, 70% by weight, 80% by weight, 90% by weight or up to 95% by weight.

The water content of the solid product is up to 5% by weight, preferably up to 4% by weight, and particularly preferably less than 3% by weight.

The invention therefore relates to an L-lysine-containing feed additive based on fermentation broth, which exhibits the following features
a) a lysine content (as base) of at least 10% by weight up to a maximum of 73% by weight,
b) a water content not exceeding 5% by weight, and
c) a biomass content corresponding to at least 0.1% of the biomass present in the fermentation broth, where the biomass, inactivated where appropriate, is formed by coryneform bacteria according to the invention.

The invention therefore also relates to an L-tryptophan-containing feed additive based on fermentation broth, which exhibits the following features
a) a tryptophan content of at least 5% by weight up to a maximum of 95% by weight,
b) a water content not exceeding 5% by weight, and
c) a biomass content corresponding to at least 0.1% of the biomass present in the fermentation broth, where the biomass, inactivated where appropriate, is formed by coryneform bacteria according to the invention.

The strain MH20-22B was deposited on 28 Oct. 2004 at the Deutsche Sammlung für Mikroorganismen and Zellkulturen (DSMZ, Brunswick, Germany) as DSM 16835.

The *Corynebacterium glutamicum* mutant DM1914 according to the invention which comprises L-valine at position 89 of the amino acid sequence of the OxyR polypeptide was deposited on 15 May 2006 at the Deutsche Sammlung für Mikroorganismen und Zellkulturen (DSMZ, Brunswick, Germany) as DSM 18259. The present invention is explained in more detail below by means of exemplary embodiments.

EXAMPLE 1

Mutagenesis of the L-Lysine-Producing Strain DM1797

The *Corynebacterium glutamicum* strain DM1797 was employed as starting strain for the mutagenesis with N-methyl-N'-nitro-N-nitrosoguanidine (MNNG). The strain DM1797 is an aminoethylcysteine-resistant mutant of *Corynebacterium glutamicum* ATCC13032 and is deposited under the designation DSM16833 at the Deutsche Sammlung für Mikroorganismen und Zellkulturen (DSMZ, Brunswick, Germany).

The strain DM1797 was cultured in 10 ml of LB broth (Merck, Darmstadt, Germany) which were present in a 100 ml Erlenmeyer flask at 33° C. and 200 rpm on an orbital shaker of the Certomat BS-1 type (B. Braun Biotech International, Melsungen, Germany) for 24 hours. The culture was then centrifuged, the sediment was resuspended in 10 ml of 0.9% NaCl solution, the resulting suspension was again centrifuged, and the resulting sediment was taken up in 10 ml of 0.9% NaCl solution. 5 ml of this cell suspension were treated with 400 µg/ml MNNG at 30° C. and 200 rpm on a shaker (see above) for 15 minutes. The mutagenesis mixture was then centrifuged and the sediment was taken up in 10 ml of 2% Na thiosulphate in 0.9% NaCl buffer (pH=6.0). The cell suspension was then diluted in the ratio 1:1000, 1:10 000 and 1:100 000 with 0.9% NaCl solution, and aliquots were plated on brain-heart agar (Merck, Darmstadt, Germany). Approximately 2500 mutants were isolated in this way.

EXAMPLE 2

Output Test on the Mutants of the Strain DM1797

The mutants obtained in Example 1 were cultured in a nutrient medium suitable for producing lysine and the lysine content in the culture supernatant was determined.

For this purpose, the clones were initially grown on brain-heart agar plates (Merck, Darmstadt, Germany) at 33° C. for 24 hours. A preculture was inoculated (10 ml of medium in 100 ml Erlenmeyer flask) starting from each of these agar plate cultures. The medium used for the preculture was the MM medium. The preculture was incubated at 33° C. and 240 rpm on a shaker for 24 hours. A main culture was inoculated from this preculture in such a way that the initial OD (660 nm) of the main culture was 0.1 OD. The MM medium was likewise used for the main culture.

| MM medium | |
|---|---|
| CSL | 5 g/l |
| MOPS | 20 g/l |
| Glucose (autoclaved separately) | 50 g/l |
| Salts: | |
| (NH$_4$)$_2$SO$_4$) | 25 g/l |
| KH$_2$PO$_4$ | 0.1 g/l |
| MgSO$_4$ * 7H$_2$O | 1.0 g/l |
| CaCl$_2$ * 2H$_2$O | 10 mg/l |

| MM medium | |
|---|---|
| FeSO$_4$ * 7H$_2$O | 10 mg/l |
| MnSO$_4$ * H$_2$O | 5.0 mg/l |
| Biotin (sterilized by filtration) | 0.3 mg/l |
| Thiamine * HCl (sterilized by filtration) | 0.2 mg/l |
| CaCO$_3$ | 25 g/l |

CSL (corn steep liquor), MOPS (morpholinopropanesulphonic acid) and the salt solution were adjusted to pH 7 with aqueous ammonia and autoclaved. The sterile substrate and vitamin solutions, and the dry autoclaved CaCO$_3$ were then added.

The culturing took place in volumes of 10 ml which were present in 100 ml Erlenmeyer flasks with baffles. The temperature was 33° C., the number of revolutions was 250 rpm and the humidity was 80%.

After 24 hours, the optical density (OD) at a measurement wavelength of 660 nm was determined using a Biomek 1000 (Beckmann Instruments GmbH, Munich, Germany). The amount of lysine formed was determined using an amino acid analyser from Eppendorf-BioTronik (Hamburg, Germany) by ion exchange chromatography and post-column derivatization with ninhydrin detection. A mutant distinguished by increased formation of lysine was called DM1914.

TABLE 1

| Strain | OD(660) | Lysine HCl (g/l) |
|---|---|---|
| DM1797 | 9.2 | 2.23 |
| DM1914 | 9.2 | 2.40 |

EXAMPLE 3

Sequencing of the oxyR Allele of the Mutant DM1914

Chromosomal DNA was isolated from the clone DM1914 by the method of Eikmanns et al. (Microbiology 140: 1817-1828 (1994)). The polymerase chain reaction was used to amplify a DNA segment which harbours the oxyR gene or allele. On the basis of the known sequence of the oxyR gene for *C. glutamicum* (sequence No. 2114 from EP1108790), the following primer oligonucleotides were selected for the PCR:

```
oxyR_XL_A1 (SEQ ID NO: 9):
5' gcgaattcgg gcatttacca tcatggtg 3' oxyR_XL_A2 (SEQ ID NO: 10):
5' gcgaattccg ctaatgcagt aggcattc 3'
```

The depicted primers were synthesized by MWG Biotech (Ebersberg, Germany) and the PCR reaction was carried out by the standard PCR method of Innis et al. (PCR Protocols. A Guide to Methods and Applications, 1990, Academic Press). The primers make it possible to amplify a DNA segment which is about 1.6 kb in length and which harbours the oxyR gene or allele. In addition, the primers contain the sequence for a cleavage site of the restriction endonuclease EcoRI, which is marked by underlining in the nucleotide sequence depicted above.

The amplified DNA fragment which has a length of about 1.6 kb and which harbours the oxyR allele of the strain DM1914 was identified by electrophoresis in a 0.8% agarose gel, isolated from the gel and purified by conventional methods (QIAquick Gel Extraction Kit, Qiagen, Hilden).

The nucleotide sequence of the amplified DNA fragment or PCR product was ascertained by sequencing by Agowa (Berlin, Germany). The sequence of the PCR product is depicted in SEQ ID NO: 15. The sequence of the coding region is additionally depicted in SEQ ID NO: 5. The amino acid sequence of the relevant OxyR transcription regulator protein which was obtained with the aid of the Patentin program is depicted in SEQ ID NO: 6.

The base thymine is located at position 266 of the nucleotide sequence of the coding region of the oxyR allele of the strain DM1914 (SEQ ID NO: 5). The base cytosine is located at the corresponding position of the wild-type gene (SEQ ID NO: 1).

The amino acid valine is located at position 89 of the amino acid sequence of the OxyR transcription regulator protein of strain DM1914 (SEQ ID NO: 6). The amino acid alanine is located at the corresponding position of the wild-type protein (SEQ ID NO: 2).

The oxyR allele which comprises the base thymine at position 266 of the coding region, and accordingly codes for an OxyR transcription regulator protein which comprises the amino acid valine at position 89 of the amino acid sequence, is referred to hereinafter as oxyR_A89V allele. In the designation "oxyR_A89V" A stands for L-alanine, V for L-valine and 89 indicates the position of the amino acid exchange (see SEQ ID NO: 2 and 6).

The *Corynebacterium glutamicum* mutant DM1914 which comprises L-valine at position 89 of the amino acid sequence of the OxyR polypeptide was deposited on 15 May 2006 at the Deutsche Sammlung für Mikroorganismen and Zellkulturen (DSMZ, Brunswick, Germany) as DSM 18259.

EXAMPLE 4

Exchange of the oxyR Wild-Type Gene of Strain DM1797 for the oxyR_A89V Allele 4.1 Construction of the Exchange Vector pK18mobsacB_oxyR_A89V The DNA fragment which has a length of about 1.6 kb, which harbours the oxyR_A89V allele and which was prepared by PCR and described in Example 3 was incorporated by exchange mutagenesis with the aid of the sacB system described in Schafer et al. (Gene, 14, 69-73 (1994)) into the chromosome of the *C. glutamicum* strain DM1797 described in Example 1. This system makes it possible to produce and select allele exchanges accomplished by homologous recombination.

For this purpose the oxyR_A89V fragment about 1.6 kb in size was cleaved with the restriction endonuclease EcoRI, identified by electrophoresis in a 0.8% agarose gel and then isolated from the gel and purified by conventional methods (QIAquick Gel Extraction Kit, Qiagen, Hilden).

The mobilizable cloning vecotr pK18mobsacB was digested with the restriction enzyme EcoRI, and the ends were dephosphorylated with alkaline phosphatase (Alkaline Phosphatase, Boehringer Mannheim, Germany). The vector prepared in this way was mixed with the approx. 1.6 kb oxyR_A89V fragment, and the mixture was treated with T4-DNA ligase (Amersham-Pharmacia, Freiburg, Germany).

The *E. coli* strain S17-1 (Simon et al., Bio/Technology 1: 784-791, 1993) was then transformed with the ligation mixture (Hanahan, In. DNA Cloning. A Practical Approach. Vol. 1, ILR-Press, Cold Spring Harbor, N.Y., 1989). Selection of the plasmid-harbouring cells took place by plating out the transformation mixture on LB agar (Sambrook et al., Molecular Cloning: A Laboratory Manual. 2nd Ed., Cold Spring Harbor, N.Y., 1989) which was supplemented by 25 mg/l kanamycin.

Plasmid DNA was isolated from a transformant with the aid of the QIAprep Spin Miniprep Kit from Qiagen and examined by restriction cleavage with the enzyme XbaI and subsequent agarose gel electrophoresis. The plasmid is called pK18mobsacB_oxyR_A89V and is depicted in FIG. 1.

4.2 Allele Exchange

The vector pK18mobsacB_oxyR_A89V mentioned in Example 4.1 was transferred by a protocol of Schafer et al. (Journal of Microbiology 172: 1663-1666 (1990)) into the *C. glutamicum* strain DM1797 by conjugation. The vector is not capable of independent replication in DM416 and remains in the cell only if it is integrated into the chromosome as the result of a recombination event. Selection of transconjugants, i.e. of clones with integrated pK18mobsacB_oxyR_A89V took place by plating out the conjugation mixture on LB agar (Sambrook et al., Molecular Cloning: A Laboratory Manual. 2nd Ed. Cold Spring Harbor, N.Y., 1989) which was supplemented with 15 mg/l kanamycin and 50 mg/l nalidixic acid. Kanamycin-resistant transconjugants were streaked onto LB agar plates with 25 mg/l kanamycin and incubated at 33° C. for 24 hours. Mutants in which the plasmid had been excised as the result of a second recombination event were selected by culturing the clones nonselectively in LB liquid medium for 30 hours, followed by streaking on LB agar with sucrose and incubating for 16 hours.

The plasmid pK18mobsacB_oxyR_A89V comprises, just like the initial plasmid pK18mobsacB, besides the kanamycin-resistance gene a copy of the sacB gene which codes for the laevan sucrase from *Bacillus subtilis*. The sucrose-inducible expression leads to the formation of laevan sucrase which catalyses the synthesis of the product laevan which is toxic for *C. glutamicum*. Thus, the only clones to grow on LB agar with sucrose are those in which the integrated pK18mobsacB_oxyR_A89V has excised as a result of a second recombination event. Depending on the position of the second recombination event in relation to the site of mutation, the allele exchange or incorporation of the mutation takes place on excision, or the original copy remains in the host's chromosome.

Approximately 40 to 50 colonies were tested for the phenotype "growth in the presence of sucrose" and "no growth in the presence of kanamycin". For 4 colonies which exhibited the phenotype "growth in the presence of sucrose" and "no growth in the presence of kanamycin", a region of the oxyR gene covering the A89V mutation and starting from the sequencing primer ox1-2 (corresponds to nucleotide sequence position 79-98 of the coding region of the oxyR gene from SEQ ID NO: 1) was sequenced by Agowa (Berlin, Germany) in order to demonstrate that the mutation of the oxyR_A89V allele is present in the chromosome. The primer ox1-2 used was synthesized by Agowa for this purpose:

```
ox1-2:
5' act gct gcc acc aag ctg tc 3'
```

A clone which contains the base thymine at position 266 of the coding region of the oxyR gene, and thus has the oxyR_A89V allele, was identified in this way. This clone is called the DM1797oxyR_A89V strain.

EXAMPLE 6

Comparison of the Output of the DM1797oxyR_A89V Strain with That of the Starting Strain DM1797

The output test on the *C. glutamicum* strain DM1797oxyR_A89V obtained in Example 5 was carried out as described in Example 2. The result of the test is depicted in Table 2.

TABLE 2

| Strain | OD (660 nm) | Lysine HCl g/l |
|---|---|---|
| DM1797 | 9.2 | 2.17 |
| DM1797oxyR_A89V | 9.2 | 2.38 |

BRIEF DESCRIPTION OF THE FIGURE

FIG. 1: Map of the plasmid pK18mobsacB_oxyR_A89V.

The abbreviations and designations used have the following meaning. The stated base pair numbers are approximations obtained within the scope of the reproducibility of measurements.

Kan: kanamycin-resistance gene
EcoRI: cleavage site of the restriction enzyme EcoRI
XbaI: cleavage site of the restriction enzyme XbaI
oxyR: oxyR_A89V allele sacB: sacB gene
RP4-mob: mob region with the origin of replication for transfer (oriT)
oriV: origin of replication V

---

What is claimed is:

1. A process for producing an L-amino acid, which comprises
   a) fermenting an isolated coryneform bacterium in a suitable medium, where the bacterium comprises at least one copy of a polynucleotide that encodes a polypeptide having OxyR transcription regulator activity, wherein the polypeptide comprises
      1) an amino acid sequence of SEQ ID NO:2, with one of the proteinogenic amino acids except L-alanine being present at position 89, and with L-valine being present at position 244,
      2) an amino acid sequence which is at least 97% identical to the amino acid sequence of SEQ ID NO:6, with L-valine being present at position 244,
      3) an amino acid sequence selected from the group consisting of i) amino acid sequence of SEQ ID NO:6, and ii) amino acid sequence of SEQ ID NO:6 including one or more conservative amino acid exchange(s),
      4) an amino acid sequence of SEQ ID NO:2, with L-valine being present at position 89, and with L-valine being present at position 244, or
      5) a combination thereof, and
   b) accumulating the L-amino acid in the fermentation broth or in the cells of the bacterium.

2. The process according to claim 1, which further comprises isolating or collecting the L-amino acid.

3. The process according to claim 2, which further comprises purifying the L-amino acid.

4. The process according to claim 1, wherein the L-amino acid is isolated or collected together with constituents of the fermentation broth and/or of the biomass (>0 to 100%).

5. The process according to claim 1, which further comprises
   c) removing the biomass formed in an amount of 0 to 100% from the fermentation broth obtained in step b) of claim 1, and
   d) producing a substantially dry and shaped product, by a method selected from the group of granulation, compaction, spray drying and extrusion, from the fermentation broth obtained in step c).

6. The process according to claim 5, wherein an acid selected from the group of sulphuric acid, hydrochloric acid and phosphoric acid is added to the fermentation broth before or after step c.

7. The process according to claim 5, wherein water is removed from the broth obtained before or after in step c).

8. The process according to claim 5, wherein the shaped product obtained in or during step d) is sprayed with an oil.

9. The process according to claim 1, wherein the following steps are carried out
   c) filtering the fermentation broth, preferably with a membrane filter, to result in a biomass-containing sludge and a filtrate,
   d) concentrating the filtrate, preferably so as to result in a solids content of from 48 to 52% by weight,
   e) granulating the concentrate obtained in step d), preferably at a temperature of from 50° C. to 62° C., and
   f) coating the granules obtained in d) with one or more of the coating agent(s).

10. An L-Lysine-containing feed additive made from the fermentation broth of claim 1, which exhibits the following features
    a) a lysine content (as base) of at least 10% by weight up to a maximum of 73% by weight,
    b) a water content not exceeding 5% by weight, and
    c) a biomass content corresponding to at least 0.1% of the biomass present in the fermentation broth, where the biomass, inactivated where appropriate comprises the isolated coryneform bacterium of claim 1.

11. An L-Tryptophan-containing feed additive made from the fermentation broth of claim 1, which exhibits the following features
    a) a tryptophan content of at least 5% by weight,
    b) a water content not exceeding 5% by weight, and
    c) a biomass content corresponding to at least 0.1% of the biomass present in the fermentation broth, where the biomass, inactivated where appropriate comprises the isolated coryneform bacterium of claim 1.

12. The method according to claim 1, wherein the coryneform bacterium is selected from the group consisting of *Corynebacterium efficiens, Corynebacterium glutamicum, Corynebacterium thermoaminogenes* and *Corynebacterium aminogenes*.

13. The method according to claim 12, wherein the bacterium is *Corynebacterium glutamicum*.

14. The method according to claim 1, wherein the L-amino acid is L-lysine, L-valine, L-isoleucine, L-tryptophan or L-homoserine.

15. The method according to claim 1, wherein the polynucleotides comprises
   i) a nucleotide sequence which is identical to the nucleotide sequence of a polynucleotide obtained by a polymerase chain reaction (PCR) using DNA obtained from a coryneform bacterium and using a primer pair consisting of a first primer including at least 15 consecutive nucleotides selected from the nucleotide sequence between position 1 and 750 of SEQ ID NO:3 or SEQ ID NO:7, and a second primer including at least 15 consecutive nucleotides selected form the complementary nucleotide sequence between position 2484 and 1731 of SEQ ID NO:3 or SEQ ID NO:7;
   ii) a nucleotide sequence which at least 97% identical to the nucleotide sequence of SEQ ID NO:5, with thymine being present at position 731;
   iii) a nucleotide sequence of SEQ ID NO:5 or SEQ ID NO:7, with the cytosine at position 731 of SEQ ID NO:5 or the cytosine at position 1481 of SEQ ID NO: 7 being replaced by thymine; or
   iv) a combination thereof.

16. The method according to claim 1, wherein the coryneform bacterium was obtained by
   a) treating a coryneform bacterium which has the ability to secrete amino acids with a mutagenic agent,
   b) isolating and propagating the mutant generated in a),
   c) preparing nucleic acid from the mutant obtained in b),
   d) preparing a nucleic acid molecule using the polymerase chain reaction, of the nucleic acid from c), and of a primer pair consisting of a first primer including at least 15 consecutive nucleotides selected from the nucleotide sequence between position 1 and 1014 of SEQ ID NO:3 or SEQ ID NO:7 and a second primer including at least 15 consecutive nucleotides selected from the complementary nucleotide sequence between position 2484 and 1018 of SEQ ID NO:3 or 7,
   e) determining the nucleotide sequence of the nucleic acid molecule obtained in d), and determining the encoded amino acid sequence,
   f) comparing the amino acid sequence determined in e) with SEQ ID NO:6, with L-valine being present at position 244, and
   g) identifying a mutant which comprises a polynucleotide which encodes a polypeptide which comprises at position 89 or a comparable position one of the proteinogenic amino acids except L-alanine, and L-valine at position 244.

17. The method according to claim 16, wherein step b) further comprises selecting a mutant which has the ability to secrete into a medium or accumulate in the interior of cells at least 0.5% more L-amino acid than the coryneform bacterium employed in step a) of claim 16.

* * * * *